US006867250B1

(12) United States Patent
Gupta et al.

(10) Patent No.: US 6,867,250 B1
(45) Date of Patent: Mar. 15, 2005

(54) NON-YELLOWING ORTHO-DIALKYL ARYL SUBSTITUTED TRIAZINE ULTRAVIOLET LIGHT ABSORBERS

(75) Inventors: Ram B. Gupta, Stamford, CT (US); Hargurpreet Singh, Ansonia, CT (US); Russell C. Cappadona, Norwalk, CT (US); Mark Paterna, Norwalk, CT (US); Al Wagner, Stratford, CT (US)

(73) Assignee: Cytec Technology Corp., Wilmington, DE (US)

( * ) Notice: Subject to any disclaimer, the term of this patent is extended or adjusted under 35 U.S.C. 154(b) by 389 days.

(21) Appl. No.: 09/698,368

(22) Filed: Oct. 30, 2000

(51) Int. Cl.$^7$ ................................................. C08K 5/34
(52) U.S. Cl. ..................... 524/100; 544/180; 544/214; 544/215; 544/216
(58) Field of Search .................. 544/180, 214, 544/215, 216, 242, 3; 524/100

(56) References Cited

U.S. PATENT DOCUMENTS

| | | |
|---|---|---|
| 3,043,709 A | 7/1962 | Amborski |
| 3,118,837 A | 1/1964 | Briggs |
| 3,242,175 A | 3/1966 | Duennenberger et al. |
| 3,244,708 A | 4/1966 | Duennenberger et al. |
| 3,309,220 A | 3/1967 | Osteen |
| 3,423,360 A | 1/1969 | Huber et al. |
| 3,487,505 A | 1/1970 | Chisholm et al. |
| 3,557,265 A | 1/1971 | Chisholm et al. |
| 3,843,371 A | 10/1974 | Piller et al. |
| 3,896,125 A | 7/1975 | Helmo et al. ............ 260/249.5 |
| 4,161,592 A | 7/1979 | Evans et al. ................ 544/198 |
| 4,314,933 A | 2/1982 | Berner ................ 260/45.75 N |
| 4,325,863 A | 4/1982 | Hinsken et al. ............. 624/111 |
| 4,331,586 A | 5/1982 | Hardy ......................... 525/186 |
| 4,338,244 A | 7/1982 | Hinsken et al. ............. 524/109 |
| 4,344,876 A | 8/1982 | Berner ......................... 524/91 |
| 4,353,965 A | 10/1982 | Olson et al. ................ 428/412 |
| 4,426,471 A | 1/1984 | Berner ......................... 524/91 |
| 4,426,472 A | 1/1984 | Berner ......................... 524/99 |
| 4,481,664 A | 11/1984 | Linger et al. ................. 382/8 |
| 4,518,686 A | 5/1985 | Sasaki et al. ............... 430/512 |
| 4,540,623 A | 9/1985 | Im et al. ..................... 428/220 |
| 4,619,956 A | 10/1986 | Susi ............................ 524/87 |
| 4,668,588 A | 5/1987 | Kishima ...................... 428/412 |
| 4,740,542 A | 4/1988 | Susi ............................ 524/87 |
| 4,775,707 A | 10/1988 | Slongo et al. ................ 524/91 |
| 4,826,978 A | 5/1989 | Migdal et al. ............. 544/216 |
| 4,853,471 A | 8/1989 | Rody et al. ................. 548/261 |
| 4,921,966 A | 5/1990 | Stegmann et al. .......... 548/260 |
| 4,937,026 A | 6/1990 | Goossens et al. ........... 264/129 |
| 4,948,666 A | 8/1990 | Paul et al. .................. 428/334 |
| 4,960,863 A | 10/1990 | Rosenquist ................. 528/480 |
| 4,962,142 A | 10/1990 | Migdal et al. .............. 524/100 |
| 4,973,701 A | 11/1990 | Winter et al. .............. 548/260 |
| 4,973,702 A | 11/1990 | Rody et al. ................. 548/261 |
| 4,992,322 A | 2/1991 | Curry et al. ................ 428/215 |
| 5,004,770 A | 4/1991 | Cortolano et al. ............ 524/99 |
| 5,006,577 A | 4/1991 | Behrens et al. ............... 524/95 |
| 5,030,731 A | 7/1991 | Slongo et al. .............. 548/260 |
| 5,064,883 A | 11/1991 | Behrens et al. ............... 524/95 |
| 5,071,981 A | 12/1991 | Son et al. .................... 544/198 |
| 5,106,891 A | 4/1992 | Valet .......................... 524/91 |
| 5,106,972 A | 4/1992 | Burdeska et al. ............ 544/219 |
| 5,112,890 A | 5/1992 | Behrens et al. ............... 524/95 |
| 5,124,378 A | 6/1992 | Behrens et al. ............... 524/95 |
| 5,175,312 A | 12/1992 | Dubs et al. .................. 549/307 |
| 5,189,084 A | 2/1993 | Birbaum et al. ............ 524/100 |
| 5,198,498 A | 3/1993 | Valet et al. ................. 525/125 |
| 5,204,473 A | 4/1993 | Winter et al. .............. 546/188 |
| 5,216,052 A | 6/1993 | Nesvadba et al. ........... 524/108 |
| 5,252,643 A | 10/1993 | Nesvadba .................... 524/111 |
| 5,288,788 A | 2/1994 | Shieh et al. ................. 524/495 |
| 5,298,067 A | 3/1994 | Valet et al. ................. 106/506 |
| 5,322,868 A | 6/1994 | Valet et al. .................. 524/89 |
| 5,354,794 A | 10/1994 | Stevenson et al. .......... 524/100 |
| 5,356,995 A | 10/1994 | Valet et al. ................. 525/100 |
| 5,369,140 A | 11/1994 | Valet et al. .................. 522/75 |
| 5,376,710 A | 12/1994 | Slongo et al. ................ 524/87 |
| 5,420,204 A | 5/1995 | Valet et al. ................. 525/125 |
| 5,438,138 A | 8/1995 | Henneberger et al. ...... 544/217 |
| 5,445,872 A | 8/1995 | Suhadolnik et al. ......... 428/215 |
| 5,459,222 A | 10/1995 | Rodgers et al. .............. 528/73 |
| 5,461,151 A | 10/1995 | Waterman ................... 544/216 |
| 5,476,937 A | 12/1995 | Stevenson et al. .......... 544/216 |
| 5,478,935 A | 12/1995 | Reinehr et al. ............. 544/180 |
| 5,563,224 A | 10/1996 | Szita et al. ................. 525/480 |
| 5,585,422 A | 12/1996 | Falk et al. .................. 524/100 |
| 5,597,854 A | 1/1997 | Birbaum et al. ............ 524/100 |
| 5,637,706 A | 6/1997 | Stevenson et al. .......... 544/216 |
| 5,726,309 A | 3/1998 | Stevenson et al. .......... 544/216 |

FOREIGN PATENT DOCUMENTS

| | | |
|---|---|---|
| DE | 3922496 | 1/1991 |
| DE | 4316611 A | 11/1993 |

(List continued on next page.)

OTHER PUBLICATIONS

Brunetti, H.; Luethi, C. E. *Helv. Chimica, Acta*, 55, (1972) 1566–1595.

(List continued on next page.)

*Primary Examiner*—Cephia D. Toomer
(74) *Attorney, Agent, or Firm*—James A. Jubinsky; Fran Wasserman; Claire M. Schultz

(57) ABSTRACT

The invention relates generally to pyrimidines and triazines ultraviolet light absorbers containing a phenolic aromatic group(s) and a non-phenolic aromatic group(s) and the use thereof to protect against degradation by environmental forces, inclusive of ultraviolet light, actinic radiation, oxidation, moisture, atmospheric pollutants, and combinations thereof. The new class of pyrimidines and triazines includes two (one) non-phenolic aromatic groups with hydrocarbyl groups that are ortho to each other and one (two) resorcinol or substituted resorcinol group attached to a triazine or pyrimidine ring. The pyrimidines and triazines may be included in a polymeric structure. A method for stabilizing a material by incorporating the novel pyrimidines and triazines is also disclosed.

63 Claims, No Drawings

FOREIGN PATENT DOCUMENTS

| | | |
|---|---|---|
| DE | 4316622 A | 11/1993 |
| DE | 4316876 | 11/1993 |
| EP | 309400 | 3/1989 |
| EP | 309401 | 3/1989 |
| EP | 309402 | 3/1989 |
| EP | 434608 | 6/1991 |
| EP | 444323 | 9/1991 |
| EP | 520938 | 12/1992 |
| EP | 531258 | 3/1993 |
| EP | 577559 | 1/1994 |
| EP | 589839 | 3/1994 |
| EP | 591102 | 4/1994 |
| EP | 648756 | 4/1995 |
| EP | 649841 | 4/1995 |
| EP | 704437 | 3/1996 |
| EP | 779280 A1 | 6/1997 |
| GB | 2269819 A | 2/1994 |
| GB | 2290745 AO | 1/1996 |
| GB | 2293823 | 4/1996 |
| JP | 9-59263 | 4/1997 |
| WO | WO 94/04515 | 3/1994 |
| WO | WO 96/28431 | 9/1996 |
| WO | WO 99/67224 | 12/1999 |
| WO | WO 00/14077 | 3/2000 |
| WO | WO 00/29392 | 5/2000 |

OTHER PUBLICATIONS

Tanimoto, S.; Yamagata, M., *Senryo to Yakahin*, 40, (1995) 339ff.

Ullmann's Encyclopedia of Industrial Chemistry, $5^{th}$ Edition, vol. A18, pp. 368–426 VCH Verlagsgesellschaft, Weinheim 1991 pp. 368–426, 429–471, 491–500.

Calbo, Leonard J., ed., Handbook of Coatings Additives, New York: Marcel Dekker (1987).

Diffey, B. L.; Robson, J., *J. Soc. Cosmet, Chem.*, 40, (1989) 127–133.

NON-YELLOWING ORTHO-DIALKYL ARYL SUBSTITUTED TRIAZINE ULTRAVIOLET LIGHT ABSORBERS

FIELD OF THE INVENTION

The invention relates generally to novel pyrimidines and triazines ultraviolet light absorbers containing a phenolic aromatic group(s) and anon-phenolic aromatic group(s), wherein the non-phenolic aromatic group(s) are substituted with hydrocarbyl groups that are ortho to each other, and their use as protectants against degradation by environmental forces, including ultraviolet light, actinic radiation, oxygen, moisture, atmospheric pollutants, and combinations thereof.

BACKGROUND OF THE INVENTION

Exposure to sunlight and other sources of ultraviolet radiation is known to cause degradation of a variety of materials, especially polymeric materials. For example, polymeric materials such as plastics often discolor and may become brittle as a result of exposure to ultraviolet light. Accordingly, a large body of art has been developed directed towards materials such as ultraviolet light absorbers and stabilizers that are capable of inhibiting such degradation.

A class of materials known to be ultraviolet light absorbers are o-hydroxyphenyltriazines, in which at least one substituent on the 1, 3, or 5 carbon of the triazine ring is a phenyl group with a hydroxyl group ortho to the point of attachment to the triazine ring. In general this class of materials is well known in the art.

For example, U.S. Pat. No. 3,843,371 discloses hydroxyphenyltriazines for use in photographic materials.

U.S. Pat. No. 3,896,125 discloses hydroxyphenyl triazines light stabilizers for organic polymeric substrates.

The use of hydroxyphenyltriazines alone or in combination with other light stabilizers such as hydroxyphenylbenzotriazoles, benzophenones, oxanilides, cyanoacrylates, salicylates, and hindered amine light stabilizers (HALS), for the stabilization of polymers is also well known. For example, U.S. Pat. Nos. 4,853,471, 4,921,966, 4,973,701, and 4,973,702 disclose such combinations.

Typically, the aforementioned aryl ring with the hydroxyl group ortho to the point of attachment to the triazine ring is based on resorcinol and, consequently, this aryl ring also contains a second substituent (either a hydroxyl group or a derivative thereof) para to the point of attachment to the triazine ring. For example, U.S. Pat. Nos. 3,118,837 and 3,244,708 disclose p-alkoxy-o-hydroxyphenyl triazines with improved UV protection.

This para-substituent can be "non-reactive," as in the case of an alkyloxy group, or "reactive" as in the case of a hydroxyalkyloxy (active hydrogen reactive site) or (meth) acryloyl (ethylenic unsaturation reactive site) group. For the purposes of the present invention, the former are referred to as "non-bondable" triazines and the latter are referred to as "bondable" triazines.

Low volatility is an important characteristic of stabilizers used in any applications where high, temperatures are encountered. High temperatures are used in the processing of thermoplastics and in the curing of thermoset resins and coatings. High temperatures are also often present in the end-use applications of the stabilized material. Low volatility will prevent loss of the stabilizer during processing, curing, and high temperature end-uses. Besides reducing losses of stabilizer during processing or curing, low volatility will minimize processing problems such as die lip build-up and plate-out.

Many polymer additives (such as ultraviolet light stabilizers) migrate out of the polymer substrate to be protected, or are adsorbed (chemically or physically) by one or more systems components (such as pigments), thereby diminishing their effectiveness. Such migration and adsorption problems are examples of the general problems of lack of solubility and compatibility found for many commercial polymer additives.

Bondable triazines are well known in the art. For example, U.S. Pat. Nos. 3,423,360, 4,962,142, and 5,189,084 disclose various bondable triazines and the incorporation of these compounds into polymers by chemical bonding. Bondable stabilizers have a potential advantage in that, depending on the bondable functionality and the particular polymer system to be stabilized, they can be chemically incorporated into a polymer structure via reaction of the bondable functionality either during polymer formation (such as in the case of polymerizing monomers or a crosslinking polymer system) or subsequently with a preformed polymer having appropriate reactive functionality. Accordingly, due to such bonding, migration of these UV absorbers between layers of multi-layer coatings and into polymer substrates is greatly reduced.

SUMMARY OF THE INVENTION

The invention is directed to novel compounds that are pyrimidine and triazine ultraviolet light absorbers. In one embodiment the compounds of the invention have formula (II)

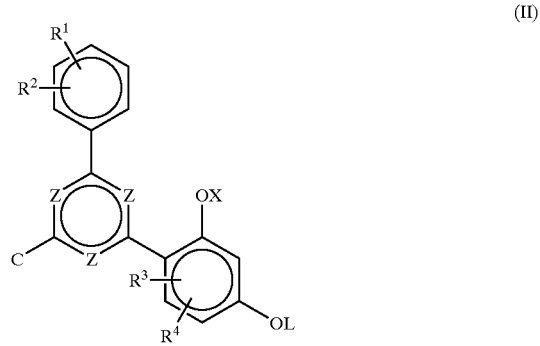

(II)

wherein each Z is independently nitrogen or methine, and at least two Z are nitrogen, to form a triazine or pyrimidine ring;

X is independently selected from hydrogen and a blocking group;

C is either

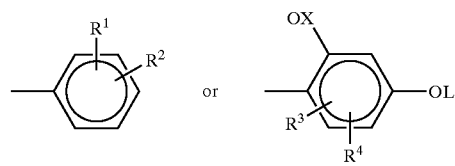

each of L is independently a
hydrogen, hydrocarbyl, —SO$_2$(hydrocarbyl), —SO$_3$ (hydrocarbyl), —SO$_2$(functional hydrocarbyl), —SO$_3$ (functional hydrocarbyl), —COO(hydrocarbyl), —COO(functional hydrocarbyl), —CO(hydrocarbyl), —CO(functional hydrocarbyl), —OCO(hydrocarbyl), —OCO(functional hydrocarbyl), —CONH$_2$, —CONH(hydrocarbyl), —CONH(functional hydrocarbyl), —CON (hydrocarbyl)(hydrocarbyl), —CON (functional hydrocarbyl)(hydrocarbyl), —CON (functional hydrocarbyl)(functional hydrocarbyl), or a hydrocarbyl group substituted by any of the above groups;

each of $R^1$ and $R^4$ are independently a hydrogen, hydrocarbyl, halogen, hydroxyl, cyano, O(hydrocarbyl), —O(functional hydrocarbyl), —N(hydrocarbyl)(hydrocarbyl), —N(hydrocarbyl)(functional hydrocarbyl), —N(functional hydrocarbyl)(functional hydrocarbyl), —S(hydrocarbyl), —S(functional hydrocarbyl), —SO$_2$(hydrocarbyl), —SO$_3$(hydrocarbyl), —SO$_2$(functional hydrocarbyl), —SO$_3$(functional hydrocarbyl), COO(hydrocarbyl), COO(functional hydrocarbyl), CO(hydrocarbyl), —CO(functional hydrocarbyl), —OCO(hydrocarbyl), —OCO(functional hydrocarbyl), —CONH$_2$, —CONH(hydrocarbyl), —CONH(functional hydrocarbyl), —CON (hydrocarbyl)(hydrocarbyl), —CON (functional hydrocarbyl)(hydrocarbyl), —CON (functional hydrocarbyl)(functional hydrocarbyl), or a hydrocarbyl group substituted by any of the above groups; and each $R^1$ and $R^2$ is identical or different and is independently a hydrocarbyl group of between 1 and 20 carbons, wherein $R^1$ and $R^2$ are attached to an aromatic benzene ring so that they are ortho to each other.

In one embodiment of the compound of formula (II), L is selected from the group consisting of:

hydrogen;

an alkyl of 1 to 24 carbon atoms optionally substituted by one or more hydroxyl, alkoxy, carboxy, carboalkoxy, amino, amido, carbamato, or epoxy groups, and which may contain one or more carbonyl groups, oxygen atoms or nitrogen atoms in the chain;

an alkenyl of 2 to 24 carbon atoms optionally substituted by hydroxyl, alkoxy, carboxy, carboalkoxy, amino, amido, carbamato, or epoxy groups and which may contain one or more carbonyl groups, oxygen atoms or nitrogen atoms in the chain or attached to the chain;

a cycloalkyl of 5 to 24 carbon atoms optionally substituted by hydroxyl, carboxyl, or amino groups and optionally containing carbonyl, oxygen, or nitrogen in the ring; an aralkyl of 7 to 24 carbon atoms optionally substituted by one or more hydroxyl, alkoxy, chloro, cyano, carboxy, carboalkoxy, amino, amido, carbamato, or epoxy groups and may contain one or more carbonyl groups, oxygen atoms or nitrogen atoms in the ring;

a polyoxyalkylene radical of the formula XII

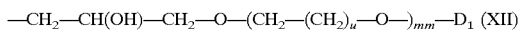

wherein $D_1$ is hydrogen,

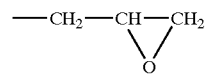

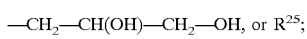

a polyoxyalkylene radical of the formula XIII

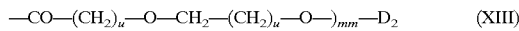 (XIII)

wherein $D_2$ is —(CH$_2$)$_u$—CO—R$^{22}$ or R$^{25}$;

a polyoxyalkylene radical of the formula XIV

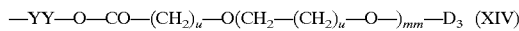 (XIV)

wherein $D_3$ is —(CH$_2$)$_u$—CO—R$^{22}$ or R$^{25}$;

a polyoxyalkylene radical of the formula XV

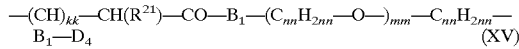 (XV)

wherein $D_4$ is hydrogen of R$^{25}$;

a polyoxyalkylene radical of the formula XVI

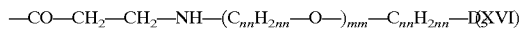 (XVI)

wherein D, is —NH$_2$, —NH—(CH$_2$)$_2$—COO—R$^{23}$ or —O—R$^{25}$;

a polyoxyalkylene radical of the formula XVII

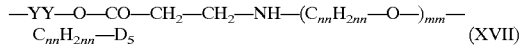 (XVII)

wherein $D_5$ is as defined under formula (XVI);

a polyoxyalkylene radical of the formula XVIII

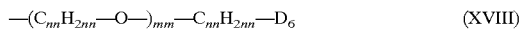 (XVIII)

wherein $D_6$ is —NH—CO—R$^{24}$, —OR$^{25}$, OH or H;

a polyoxyalkylene radical of the formula XIX

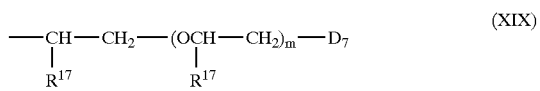 (XIX)

wherein $D_7$ is —OR$^{25}$, —NHCOR$^{24}$ or —OCH$_2$CH$_2$OR$^{25}$;

$R^{21}$ is hydrogen or C$_1$–C$_{16}$ alkyl;

$R^{17}$ is C$_2$–C$_{10}$ alkylene, phenylene, naphthylene, diphenylene, or C$_2$–C$_6$ alkenylene, methylenediphenylene, or C$_4$–C$_{15}$ alkylphenylene;

$R^{21}$ is hydrogen or C$_1$–C$_{16}$ alkyl;

$R^{22}$ is halogen or —O—R';

$R^{23}$ is hydrogen, C$_1$–C$_6$ alkyl, C$_3$–C$_6$ alkenyl, aryl, or aryl-C$_1$–C$_4$-alkyl;

$R^{24}$ is hydrogen, C$_1$–C$_{12}$ alkyl or aryl;

$R^{25}$ is C$_1$–C$_{16}$ alkyl, C$_5$–C$_{12}$ cycloalkyl, C$_3$–C$_6$ alkenyl, C$_1$–C$_{12}$ alkylaryl or aryl-C$_1$–C$_4$ alkyl;

YY is unsubstituted or substituted C$_2$–C$_{20}$ alkyl;

$B_1$, is HN or O;

kk is zero or an integer from 1–16;

mm is an integer from 2 to 60;

nn is an integer from 2 to 6;

u is an integer from 1 to 4.

In another embodiment of the compound of formula (II), L is an alkyl chain of between 1 and 20 carbons optionally interrupted by one or more oxygen atoms, having one or more of the hydrogens in the alkyl chain substituted for by a hydroxyl group, or terminating with a carbonyl functionality of general structure —CO—M, wherein M is a OR$^x$, NR$^x$R$^y$ wherein R$^x$ and R$^y$ are independently hydrogen or an alkyl group of between 1 and 8 carbons that optionally have one or more of the hydrogens substituted for by a hydroxyl group.

In the compound of formula (II) R$^3$ and R$^4$ may be independently selected from hydrogen, and an alkyl of 1 to 8 carbons atoms wherein one or more of the hydrogens in the alkyl chain may optionally be substituted with an the nitrogen of an amine.

In the compound of formula (II) R$^1$ and R$^2$ may be individually a C$_1$ to C$_{10}$ straight chain alkyl, branched alkyl, or cycloalkyl and R$^1$ and R$^2$ may be attached to the aromatic benzene ring at the 3 and 4 position relative to the point of attachment of the triazine ring or they may be attached to the aromatic benzene ring at the 2 and 3 position relative to the point of attachment of the triazine ring.

In the compound of formula (II) each Z may be a nitrogen.

In one embodiment of the compound of formula II each Z is a nitrogen and C is

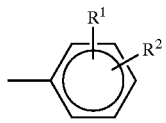

In this embodiment when C is

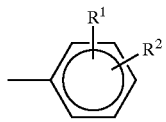

each R$^1$ and R$^2$ may be methyl groups.

In another embodiment of the compound of formula (II) each Z is nitrogen; X is hydrogen; C is

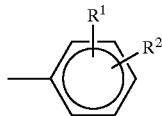

each R$_1$ and R$_2$ is individually a C$_1$ to C$_{10}$ straight chain alkyl, branched alkyl, or cycloalkyl; L is alkyl chain of between 1 and 20 carbons, wherein the alkyl chain is optionally interrupted by one or more oxygen atoms, has one or more of hydrogens in the alkyl chain substituted for by a hydroxyl group, or terminates with a carbonyl functionality of general structure —CO—M, wherein M is a OR$^x$, NR$^x$R$^y$ wherein R$^x$ and R$^y$ are independently hydrogen or an alkyl group of between 1 and 8 carbons that optionally has one or more of the hydrogens substituted for by a hydroxyl group; and R$^3$ and R$^4$ are each hydrogen.

In another embodiment the compound of the invention has the formula (III):

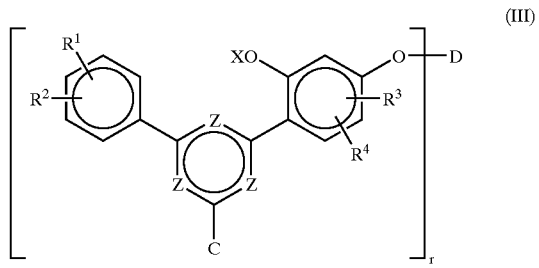

wherein each Z is independently nitrogen or methine, and at least two Z are nitrogen, to produce a triazine or pyrimidine ring;

X is independently selected from hydrogen and a blocking group;

C is either

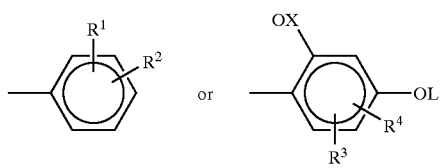

r is an integer between 2 and 4;

each of L is independently a
hydrogen, hydrocarbyl, —SO$_2$(hydrocarbyl), —SO$_3$ (hydrocarbyl), —SO$_2$(functional hydrocarbyl), —SO$_3$ (functional hydrocarbyl), —COO(hydrocarbyl), —COO(functional hydrocarbyl), CO(hydrocarbyl), —CO(functional hydrocarbyl), —OCO(hydrocarbyl), —OCO(functional hydrocarbyl), —CONH$_2$, —CONH (hydrocarbyl), —CONH(functional hydrocarbyl), —CON (hydrocarbyl)(hydrocarbyl), —CON (functional hydrocarbyl)(hydrocarbyl), —CON (functional hydrocarbyl)(functional hydrocarbyl), or a hydrocarbyl group substituted by any of the above groups;

each of R$^3$ and R$^4$ are independently a
hydrogen, hydrocarbyl, halogen, hydroxyl, cyano, —O(hydrocarbyl), —O(functional hydrocarbyl), —N(hydrocarbyl)(hydrocarbyl), —N(hydrocarbyl) (functional hydrocarbyl), —N(functional hydrocarbyl) (functional hydrocarbyl), —S(hydrocarbyl), —S(functional hydrocarbyl), —SO$_2$(hydrocarbyl), —SO$_3$(hydrocarbyl), —SO$_2$(functional hydrocarbyl), —SO$_3$(functional hydrocarbyl), —COO(hydrocarbyl), —COO(functional hydrocarbyl), —CO(hydrocarbyl), —CO(functional hydrocarbyl), —OCO(hydrocarbyl), —OCO(functional hydrocarbyl), —CONH$_2$, —CONH (hydrocarbyl), —CONH(functional hydrocarbyl), —CON (hydrocarbyl)(hydrocarbyl), —CON (functional hydrocarbyl)(hydrocarbyl), —CON (functional hydrocarbyl)(functional hydrocarbyl), or a hydrocarbyl group substituted by any of the above groups;

each R$^1$ and R$^2$ is identical or different and is independently a hydrocarbyl group of between 1 and 20 carbons, wherein R$^1$ and R$^2$ are attached to an aromatic benzene ring so that they are ortho to each other;

D, when r is 2, is selected from the group consisting of C$_1$–C$_{16}$ alkylene, C$_4$–C$_{12}$ alkenylene, xylylene, C$_4$–C$_{20}$ alkylene which is interrupted by one or more oxygen atoms, hydroxy-substituted $C_{3-0}$ alkyl which is interrupted by one or more oxygen atoms, —$CH_2CH(OH)CH_2O$—$R^{15}$—$OCH_2CH(OH)CH_2$—, —CO—$R^{16}$—CO—, —CO—NH—$R^{17}$—NH—CO—, —$(CH_2)_s$—COO—$R^{18}$—OCO—$(CH_2)_s$— a polyoxyalkylene bridge member of the formula XX

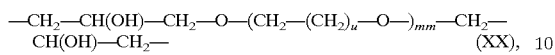

a polyoxyalkylene bridge member of the formula XXI

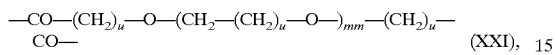

a polyoxyalkylene bridge member of the formula XXII

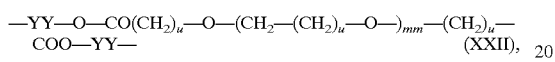

a polyoxyalkylene bridge member of the formula XXIII

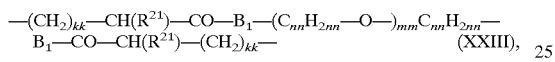

a polyoxyalkylene bridge member of the formula XXIV

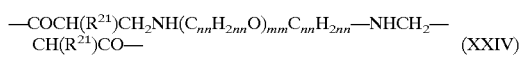

a polyoxyalkylene bridge member of the formula XXV

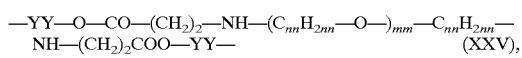

a polyoxyalkylene bridge member of the formula XXVI

and a polyoxyalkylene bridge member of the formula XXVII

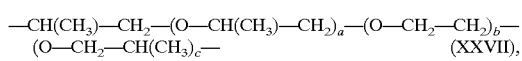

wherein a+c=2.5 and b=8.5 to 40.5 or a+c=2 to 33 and b=0, $R^{15}$ is $C_2$–$C_{10}$ alkylene, $C_2$–$C_{10}$ oxaalkylene or $C_2$–$C_{10}$ dithiaalkylene, phenylene, naphthylene, diphenylene, or $C_2$–$C_6$ alkenylene, or phenylene-XX-phenylene wherein XX is —O—, —S—, —$SO_2$—, —$H_2$—, or <$(CH_3)_2$—;

$R^{16}$ is $C_2$–$C_{10}$ alkylene, $C_2$–$C_{10}$ oxaalkylene or $C_2$–$C_{10}$ dithiaalkylene, phenylene, naphthylene, diphenylene, or $C_2$–$C_6$ alkenylene provided that when r is 3 the alkenylene has at least 3 carbons;

$R^{17}$ is $C_2$–$C_{10}$ alkylene, phenylene, naphthylene, diphenylene, or $C_2$–$C_6$ alkenylene, methylenediphenylene, or $C_4$–$C_{15}$ alkylphenylene; and $R^{18}$ is $C_2$–$C_{10}$ alkylene, or $C_4$–$C_{20}$ alkylene interrupted by one or more oxygen atoms;

$R^{21}$ is hydrogen or $C_1$–$C_{16}$ alkyl;

YY is unsubstituted or substituted $C_2$–$C_{20}$ alkyl;

$B_1$ is NH or O;

kk is zero or an integer from 1–16;

mm is an integer from 2 to 60;

nn is an integer from 2 to 6;

s is 1–6;

u is an integer from 1 to 4;

when r is 3, D is

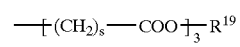

and when r is 4, D is

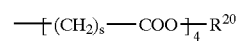

wherein $R^{19}$ is $C_3$–$C_{10}$ alkanetriyl and $R^{20}$ is $C_4$–$C_{10}$ alkanetetryl.

In one embodiment of the compound of formula (III), r is 2 and D is an alkyl chain of between 1 and 10 carbons or —CO—P—CO—, wherein P is an alkyl chain of between 1 and 10 carbons or a benzene ring wherein the carbonyl groups are meta or para to each other. In this embodiment $R^3$ and $R^4$ may be independently selected from hydrogen, and an alkyl of 1 to 8 carbons atoms wherein one or more of the hydrogens in the alkyl chain may optionally be substituted with the nitrogen of an amine, $R^1$ and $R^2$ may also be individually a $C_1$ to $C_{10}$ straight chain alkyl, branched alkyl, or cycloalkyl and $R^1$ and $R^2$ can be attached to the aromatic benzene ring at the 3 and 4 position relative to the point of attachment of the triazine ring or may be attached to the aromatic benzene ring at the 2 and 3 position relative to the point of attachment of the triazine ring. Each Z may be a nitrogen and C may be

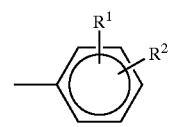

When C is

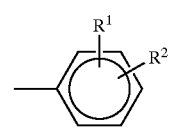

each $R^1$ and $R^2$ may be methyl groups.

In another embodiment of the compound of formula (III) each Z is nitrogen; X is hydrogen; C is

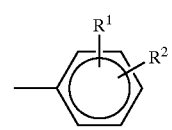

ach $R_1$ and $R_2$ is individually a $C_1$ to $C_{10}$ straight chain alkyl, branched alkyl, or cycloalkyl; and $R^3$ and $R^4$ are each hydrogen.

In another embodiment the compound of the invention has the formula (IV):

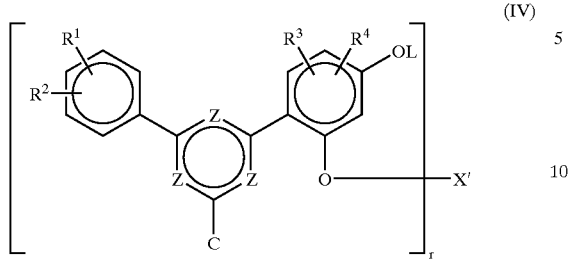
(IV)

wherein each Z is independently nitrogen or methine, and at least two Z are nitrogen, to produce a triazine or pyrimidine ring;
C is either

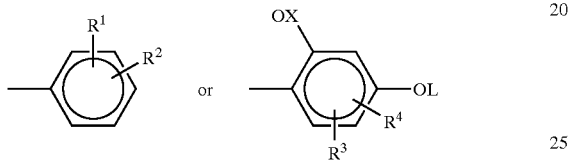

wherein X is selected from hydrogen and a blocking group;
r is an integer between 2 and 4;
each of L is independently a
hydrogen, hydrocarbyl, —SO$_2$(hydrocarbyl), —SO$_3$(hydrocarbyl), —SO$_2$(functional hydrocarbyl), —SO$_3$(functional hydrocarbyl), —COO(hydrocarbyl), COO(functional hydrocarbyl), —CO(hydrocarbyl), —CO(functional hydrocarbyl), —OCO(hydrocarbyl), —OCO(functional hydrocarbyl), —CONH$_2$, —CONH(hydrocarbyl), —CONH(functional hydrocarbyl), —CON(hydrocarbyl)(hydrocarbyl), —CON(functional hydrocarbyl)(hydrocarbyl), —CON(functional hydrocarbyl)(functional hydrocarbyl), or a hydrocarbyl group substituted by any of the above groups;
each of $R^3$ and $R^4$ are independently a
hydrogen, hydrocarbyl, halogen, hydroxyl, cyano, —O(hydrocarbyl), —O(functional hydrocarbyl), —N(hydrocarbyl)(hydrocarbyl), —N(hydrocarbyl)(functional hydrocarbyl), —N(functional hydrocarbyl)(functional hydrocarbyl), —S(hydrocarbyl), —S(functional hydrocarbyl), —SO$_2$(hydrocarbyl), —SO$_3$(hydrocarbyl), —SO$_2$(functional hydrocarbyl), —SO$_3$(functional hydrocarbyl), —COO(hydrocarbyl), —COO(functional hydrocarbyl), —CO(hydrocarbyl), —CO(functional hydrocarbyl), —OCO(hydrocarbyl), —OCO(functional hydrocarbyl), —CONH$_2$, —CONH(hydrocarbyl), —CONH(functional hydrocarbyl), —CON(hydrocarbyl)(hydrocarbyl), —CON(functional hydrocarbyl)(hydrocarbyl), —CON(functional hydrocarbyl)(functional hydrocarbyl), or a hydrocarbyl group substituted by any of the above groups;
each $R^1$ and $R^2$ is identical or different and is independently a hydrocarbyl group of between 1 and 20 carbons, wherein $R^1$ and $R^2$ are attached to an aromatic benzene ring so that they are ortho to each other;
X' when r is 2, is selected from the group consisting of $C_1$–$C_{16}$ alkylene, $C_4$–$C_{12}$ alkenylene, xylylene, $C_4$–$C_{20}$ alkylene which is interrupted by one or more oxygen atoms, hydroxy-substituted $C_3$–$C_{20}$ alkyl which is interrupted by one or more oxygen atoms, —CH$_2$CH(OH)CH$_2$O—R$^{15}$—OCH$_2$CH(OH)CH$_2$—, —CO—R$^{16}$—CO—, —CO—NH—R$^{17}$—H—C—, —(CH$_2$)$_s$—COO—R$^{18}$—OCO—(CH$_2$)$_s$—
a polyoxyalkylene bridge member of the formula XX

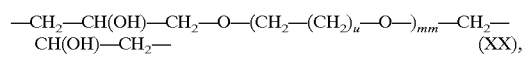
(XX), a polyoxyalkylene bridge member of the formula XXI

(XXI), a polyoxyalkylene bridge member of the formula XXII

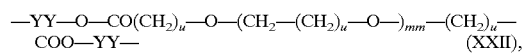
(XXII), a polyoxyalkylene bridge member of the formula XXIII

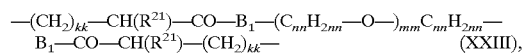
(XXIII), a polyoxyalkylene bridge member of the formula XXIV

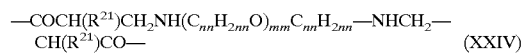
(XXIV)

a polyoxyalkylene bridge member of the formula XXV

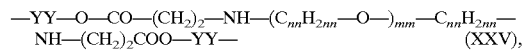
(XXV), a polyoxyalkylene bridge member of the formula XXVI

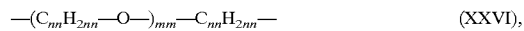
(XXVI), and a polyoxyalkylene bridge member of the formula XXVII

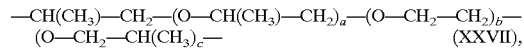
(XXVII), wherein a+c=2.5 and b=8.5 to 40.5 or a+c=2 to 33 and b=0,
$R^{15}$ is $C_2$–$C_{10}$ alkylene, $C_2$–$C_{10}$ oxaalkylene or $C_2$–$C_{10}$ dithiaalkylene, phenylene, naphthylene, diphenylene, or $C_2$–$C_6$ alkenylene, or phenylene-XX-phenylene wherein XX is O, —S—, —SO$_2$—, —H$_2$—, or C(CH$_3$)$_2$—;
R)$^6$ is $C_2$–$C_{10}$ alkylene, $C_2$–$C_{10}$ oxaalkylene or $C_2$–$C_{10}$ dithiaalkylene, phenylene, naphthylene, diphenylene, or $C_2$–$C_6$ alkenylene provided that when r is 3 the alkenylene has at least 3 carbons;
$R^{17}$ is $C_2$–$C_{10}$ alkylene, phenylene, naphthylene, diphenylene, or $C_2$–$C_6$ alkenylene, methylenediphenylene, or $C_4$–$C_{15}$ alkylphenylene; and
$R^{18}$ is $C_2$–$C_{10}$ alkylene, or $C_4$–$C_{20}$ alkylene interrupted by one or more oxygen atoms;
$R^{21}$ is hydrogen or $C_1$–$C_{16}$ alkyl;
YY is unsubstituted or substituted $C_2$–$C_{20}$ alkyl;
$B_1$ is NH or O;
kk is zero or an integer from 1–16;
mm is an integer from 2 to 60;

nn is an integer from 2 to 6;
s is 1–6;
u is an integer from 1 to 4;
when r is 3, X' is

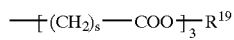

and when r is 4, X' is

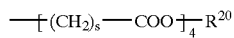

wherein $R^{19}$ is $C_3$–$C_{10}$ alkanetriyl and $R^{20}$ is $C_4$–$C_{10}$ alkanetetryl.

In one embodiment of the compound of formula (IV) r is 2 and X' is an alkyl chain of between 1 and 10 carbons or —CO—P—CO—, wherein P is an alkyl chain of between 1 and 10 carbons or a benzene ring wherein the carbonyl groups are meta or para to each other. In this embodiment $R^3$ and $R^4$ may be independently selected from hydrogen, and an alkyl of 1 to 8 carbons atoms wherein one or more of the hydrogens in the alkyl chain may optionally be substituted with an the nitrogen of an amine. In this embodiment L may be an alkyl chain of between 1 and 20 carbons, wherein the alkyl chain is optionally interrupted by one or more oxygen atoms, has one or more of the hydrogens in the alkyl chain substituted for by a hydroxyl group, or terminates with a carbonyl functionality of general structure —CO—M, wherein M is a $OR^x$ or $NR^xR^y$, wherein $R^x$ and $R^y$ are independently hydrogen or an alkyl group of between 1 and 8 carbons that optionally may have one or more of the hydrogens substituted for by a hydroxyl group. In this embodiment $R^1$ and $R^2$ may be individually a $C_1$ to $C_{10}$ straight chain alkyl, branched alkyl or cycloalkyl and $R^1$ and $R^2$ may be attached to the aromatic benzene ring at the 3 and 4 position relative to the point of attachment of the triazine ring or attached to the aromatic benzene ring at the 2 and 3 position relative to the point of attachment of the triazine ring. In this embodiment each Z may be a nitrogen and C may be

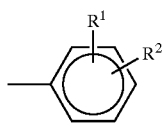

When C is

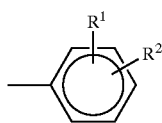

each $R^1$ and $R^2$ may be methyl groups.

In another embodiment of the compound of formula (IV) each Z is nitrogen; X is hydrogen; C is

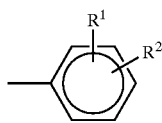

each $R_1$ and $R_2$ is individually a $C_1$ to $C_{10}$ straight chain alkyl, branched alkyl, or cycloalkyl; and $R^3$ and $R^4$ are each hydrogen.

In yet another embodiment, the compound of the invention has the formula (V)

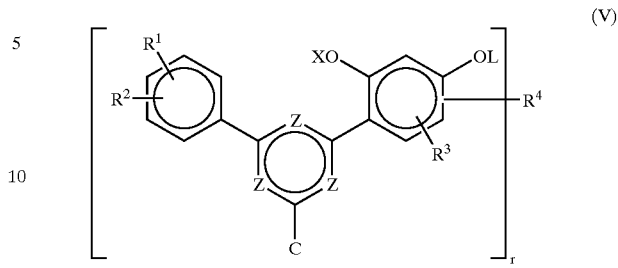

wherein each Z is independently nitrogen or methine, and at least two Z are nitrogen, to form a triazine or pyrimidine ring;

X is independently selected from hydrogen and a blocking group;

C is

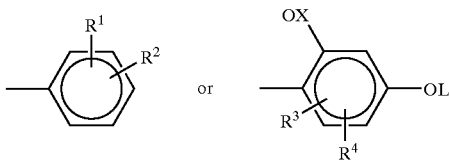

r is 2;

L is independently a
hydrogen, hydrocarbyl, —SO$_2$(hydrocarbyl), —SO$_3$(hydrocarbyl), —SO$_2$(functional hydrocarbyl), —SO$_3$(functional hydrocarbyl), —COO(hydrocarbyl), COO (functional hydrocarbyl), —CO(hydrocarbyl), —CO (functional hydrocarbyl), —OCO(hydrocarbyl), —OCO(functional hydrocarbyl), —CONH$_2$, —CONH (hydrocarbyl), —CONH(functional hydrocarbyl), —CON (hydrocarbyl)(hydrocarbyl), —CON (functional hydrocarbyl)(hydrocarbyl), —CON (functional hydrocarbyl)(functional hydrocarbyl), or a hydrocarbyl group substituted by any of the above groups;

$R^3$ is independently a
hydrogen, hydrocarbyl, halogen, hydroxyl, cyano, —O(hydrocarbyl), —O(functional hydrocarbyl), —N(hydrocarbyl)(hydrocarbyl), —N(hydrocarbyl) (functional hydrocarbyl), —N(functional hydrocarbyl) (functional hydrocarbyl), —S(hydrocarbyl), —S(functional hydrocarbyl), —SO$_2$(hydrocarbyl), —SO$_3$(hydrocarbyl), —SO$_2$(functional hydrocarbyl), —SO$_3$(functional hydrocarbyl), —COO(hydrocarbyl), COO(functional hydrocarbyl), CO(hydrocarbyl), —CO(functional hydrocarbyl), —OCO(hydrocarbyl), —OCO(functional hydrocarbyl), —CONH$_2$, —CONH (hydrocarbyl), —CONH(functional hydrocarbyl), —CON (hydrocarbyl)(hydrocarbyl), —CON (functional hydrocarbyl)(hydrocarbyl), —CON (functional hydrocarbyl)(functional hydrocarbyl), or a hydrocarbyl group substituted by any of the above groups;

each $R^1$ and $R^2$ is identical or different and is independently a hydrocarbyl group of between 1 and 20 carbons, wherein $R^1$ and $R^2$ are attached to an aromatic benzene ring so that they are ortho to each other; and $R^4$ is selected from the group consisting of straight chain alkyl of 1 to 12 carbon atoms, branched chain alkyl of 1 to 12 carbon atoms, cycloalkyl of 5 to 12 carbon atoms, alkyl substituted by cyclohexyl, alkyl interrupted by cyclohexyl, alkyl substituted by phenylene, alkyl interrupted by phenylene, benzylidene, —S—, —S—S—, —S—E—S—, —SO—, —SO$_2$—, —SO—E—SO—, —SO$_2$—E—SO$_2$—, —CH, —NH—E—NH—CH$_2$—, and

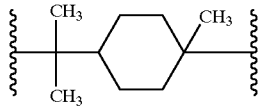

wherein E is selected from the group consisting of alkyl of 2 to 12 carbon atoms, cycloalkyl of 5 to 12 carbon atoms, alkyl interrupted by cyclohexyl of 8 to 12 carbon atoms and, alkyl terminated by cyclohexyl of 8 to 12 carbon atoms.

In the compound of formula (V) R$^4$ may be —CH$_2$— and R$^3$ may be hydrogen, or an alkyl of 1 to 8 carbons atoms wherein one or more of the hydrogens in the alkyl chain may optionally be substituted with an the nitrogen of an amine. In this embodiment L may be an alkyl chain of between 1 and 20 carbons, wherein the alkyl chain is optionally interrupted by one or more oxygen atoms, has one or more of the hydrogens in the alkyl chain substituted for by a hydroxyl group, or terminates with a carbonyl functionality of general structure —CO—M, wherein M is a OR$^x$ or NR$^x$R$^y$, wherein R$^x$ and R$^y$ are independently hydrogen or an alkyl group of between 1 and 8 carbons that optionally may have one or more of the hydrogens substituted for by a hydroxyl group. In this embodiment R$^1$ and R$^2$ may be individually a C$_1$ to C$_{10}$ straight chain alkyl, branched alkyl, or cycloalkyl and R$^1$ and R$^2$ may be attached to the aromatic benzene ring at the 3 and 4 position relative to the point of attachment of the triazine ring or attached to the aromatic benzene ring at the 2 and 3 position relative to the point of attachment of the triazine ring. Each Z may be a nitrogen.

In another embodiment of the compound of formula (V) each Z is nitrogen; X is hydrogen; C is

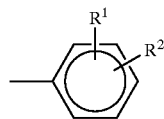

each R$_1$ and R$_2$ is individually a C$_1$ to C$_{10}$ straight chain alkyl, branched alkyl, or cycloalkyl; and R$^3$ is a hydrogen.

The invention also relates to polymeric articles comprising at least one polymeric material and a sufficient amount of a stabilizing composition to inhibit at least one of photo or thermal degradation. The stabilizer composition comprises one or more compounds of structure (II)–(V), wherein compound (II) has the structure:

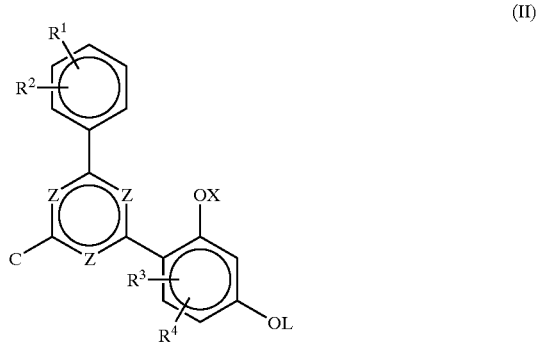

wherein each Z is independently nitrogen or methine, and at least two Z are nitrogen, to form a triazine or pyrimidine ring;

X is independently selected from hydrogen and a blocking group;

C is

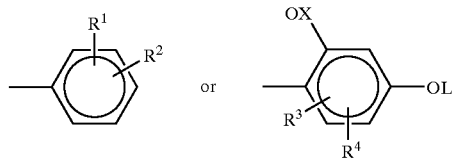

L is an alkyl chain of between 1 and 20 carbons, wherein the alkyl chain is optionally interrupted by one or more oxygen atoms, has one or more of hydrogens in the alkyl chain substituted for by a hydroxyl group, or terminates with a carbonyl functionality of general structure —CO—M, wherein M is a OR$^x$, NR$^x$R$^y$ and R$^x$ and R$^y$ are independently hydrogen or an alkyl group of between 1 and 8 carbons that optionally may have one or more of the hydrogens substituted for by a hydroxyl group;

R$^3$ and R$^4$ is independently selected from hydrogen, and an alkyl of 1 to 8 carbons atoms wherein one or more of the hydrogens in the alkyl chain may optionally be substituted with an the nitrogen of an amine; and each R$^1$ and R$^2$ is individually a C$_1$ to C$_{10}$ straight chain alkyl, branched alkyl, or cycloalkyl and R$^1$ and R$^2$ are attached to an aromatic benzene ring so that they are ortho to each other; compound (III) has the structure:

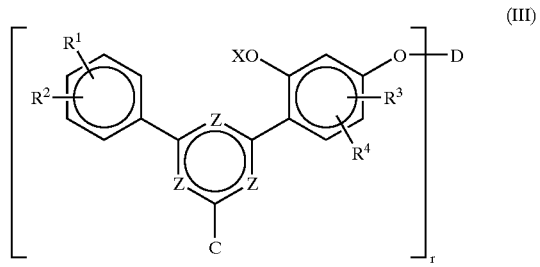

wherein each Z is independently nitrogen or methine, and at least two Z are nitrogen, to form a triazine or pyrimidine ring;

X is independently selected from hydrogen and a blocking group;

C is

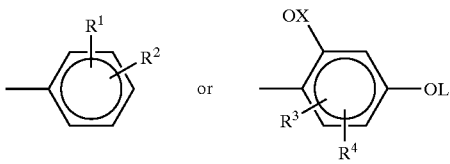

r is 2 and D is an alkyl chain of between 1 and 10 carbons or —CO—P—CO—, wherein P is an alkyl chain of between 1 and 10 carbons or a benzene ring wherein the carbonyl groups are meta or para to each other;

$R^3$ and $R^4$ is independently selected from hydrogen, and an alkyl of 1 to 8 carbons atoms wherein one or more of the hydrogens in the alkyl chain may optionally be substituted with an the nitrogen of an amine; and $R^1$ and $R^2$ is individually a $C_1$ to $C_{10}$ straight chain alkyl, branched alkyl, or cycloalkyl and $R^1$ and $R^2$ are attached to an aromatic benzene ring so that they are ortho to each other;

compound (IV) has the structure:

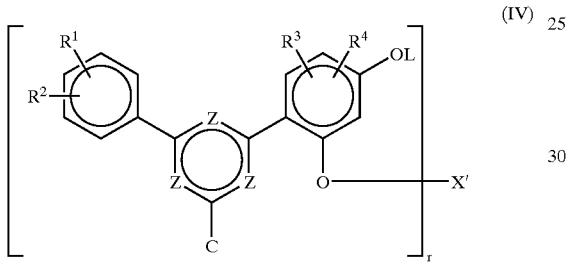

(IV)

wherein each Z is independently nitrogen or methine, and at least two Z are nitrogen, to form a triazine or pyrimidine ring;

C is

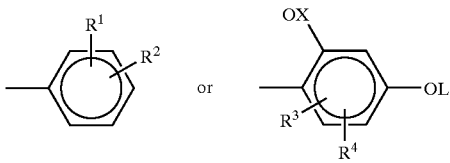

wherein r is 2 and X' is an alkyl chain of between 1 and 10 carbons or —CO—P—CO—, wherein P is an alkyl chain of between 1 and 10 carbons or a benzene ring wherein the carbonyl groups are meta or para to each other;

$R^3$ and $R^4$ is independently selected from hydrogen, and an alkyl of 1 to 8 carbons atoms wherein one or more of the hydrogens in the alkyl chain may optionally be substituted with an the nitrogen of an amine;

L is alkyl chain of between 1 and 20 carbons, wherein the alkyl chain is optionally interrupted by one or more oxygen atoms, has one or more of the hydrogens in the alkyl chain substituted for by a hydroxyl group, or terminates with a carbonyl functionality of general structure —CO—M, wherein M is a $OR^x$, $NR^xR^y$ and $R^x$ and $R^y$ are independently hydrogen or an alkyl group of between 1 and 8 carbons that optionally may have one or more of the hydrogens substituted for by a hydroxyl group;

$R^1$ and $R^2$ is individually a $C_1$ to $C_{10}$ straight chain alkyl, branched alkyl, or cycloalkyl and $R^1$ and $R^2$ are attached to an aromatic benzene ring so that they are ortho to each other;

and compound (V) has the structure:

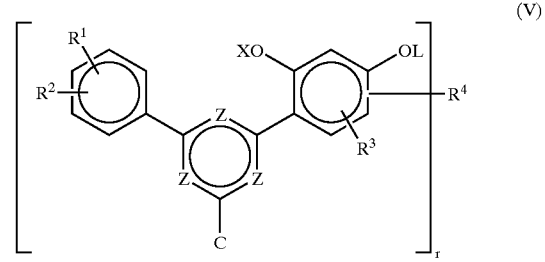

(V)

wherein each Z is independently nitrogen or methine, and at least two Z are nitrogen, to form a triazine or pyrimidine ring;

X is independently selected from hydrogen and a blocking group;

C is

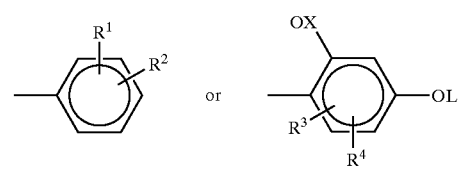

r is 2;

$R^4$ is —CH$_2$—;

$R^3$ is selected from hydrogen, and an alkyl of 1 to 8 carbons atoms wherein one or more of the hydrogens in the alkyl chain may optionally be substituted with an the nitrogen of an amine;

L is alkyl chain of between 1 and 20 carbons, wherein the alkyl chain is optionally interrupted by one or more oxygen atoms, has one or more of the hydrogens in the alkyl chain substituted for by a hydroxyl group, or terminates with a carbonyl functionality of general structure —CO—M, wherein M is a $OR^x$, $NR^xR^y$ and $R^x$ and $R^y$ are independently hydrogen or an alkyl group of between 1 and 8 carbons that optionally may have one or more of the hydrogens substituted for by a hydroxyl group; and $R^1$ and $R^2$ is individually a $C_1$ to $C_{10}$ straight chain alkyl, branched alkyl, or cycloalkyl and $R^1$ and $R^2$ are attached to an aromatic benzene ring so that they are ortho to each other.

The amount of stabilizer composition in the polymeric article may be is from about 0.01 to about 20 percent by weight of the polymeric material. The polymeric material may be selected from the group consisting of polyolefins; polyesters; polyethers; polyketones; polyamides; natural and synthetic rubbers; polyurethanes; polystyrenes; high-impact polystyrenes; polyacrylates; polymethacrylates; polyacetals; polyacrylonitriles; polybutadienes; polystyrenes; ABS; SAN (styrene acrylonitrile); ASA (acrylate styrene acrylonitrile); cellulosic acetate butyrate; cellulosic polymers; polyimides; polyamideimides; polyetherimides; polyphenylsulfides; PPO; polysulfones; polyethersulfones; polyvinylchlorides; polycarbonates; polyketones; aliphatic polyketones; thermoplastic TPO's; aminoresin crosslinked polyacrylates and polyesters; polyisocyanate crosslinked polyesters and polyacrylates; phenolformaldehyde, urea/formaldehyde, and melamine/formaldehyde resins; drying and non-drying alkyd resins; alkyd resins; polyester resins; acrylate resins cross-linked with melamine resins, urea resins, isocyanates, isocyanurates, carbamates, and epoxy resins; cross-linked epoxy resins derived from aliphatic, cycloaliphatic, heterocyclic and aromatic glycidyl compounds which are cross-linked with anhydrides or amines; polysiloxanes; Michael addition polymers of amines or blocked amines with activated unsaturated and methylene compounds, ketimines with activated unsaturated and methylene compounds, polyketimines in combination with unsaturated acrylic polyacetoacetate resins, and polyketimines in combination with unsaturated acrylic resins; radiation curable compositions; epoxymelamine resins; organic dyes; cosmetic products; cellulose-based paper formulations; photographic film paper; ink; and blends thereof.

The one or more compounds of formula (II) to (V) may be chemical bonded to the polymer.

The stabilizer composition may further comprise one or more hindered amine light stabilizers or one or more additional UV light absorbers selected from the group consisting of a benzotriazole, a triazine, a benzophenone, and mixtures thereof. The stabilizer composition may further comprises at least one additional additive, selected from the group consisting of: antioxidants, ultraviolet light absorbers, ultraviolet light stabilizers, metal deactivators, phosphites, phosphonites, hydroxylamines, nitrones, thiosynergists, peroxide scavengers, polyamide stabilizers, nucleating agents, fillers, reinforcing agents, plasticizers, lubricants, emulsifiers, pigments, rheological additives, flameproofing agents, antistatic agents, blowing agents, benzofuranones and indolinones.

The invention also relates to multilayer polymeric article comprising a polymeric article having at least one surface and a thin film of polymer composition applied to the at least one surface wherein the thin film comprises at least one compound of formula (II)–(V) wherein the compounds of formula (II)–(V) have the same structure as the compounds added to the polymeric articles. The thin film may be applied to each surface of the polymeric article. The amount of the compound in the thin film may be from about 0.1 to 20 percent by weight of the thin film. The thin film may be from about 5 to 500 µm in thickness.

The invention also relates to a coating comprising at least one compound of formula (II)–(V) to inhibit at least one of photo or thermal degradation, wherein the compounds of formula (II)–(V) have the same structure as the compounds added to the polymeric articles. The amount of the one or more compounds is from about 0.01 to 20 percent by weight of the coating.

The invention also relates to a concentrate comprising a polymeric resin and from about 2.5 to about 25 percent of at least one compound of formula (II)–(V), wherein the compounds of formula (II)–(V) have the same structure as the compounds added to the polymeric articles.

The invention also relates to a cosmetic composition comprising a sufficient amount of at least one compound of formula (II)–(V), wherein the compounds of formula (II)–(V) have the same structure as the compounds added to the polymeric articles.

The invention further relates to a method of stabilizing a material that is subject to at least one of photo or thermal degradation by incorporating into or onto the material an amount of one or more stabilizer compositions effective to stabilize the material against at least one of photo or thermal degradation, wherein the stabilizer composition comprises one or more compounds of structure (II)–(V), wherein the compounds of formula (II)–(V) have the same structure as the compounds added to the polymeric articles.

The stabilizer composition may be incorporated into the material in an amount of from about 0.01 to about 20 percent by weight of the material to be stabilized. The material to be stabilized may be polymeric. The polymeric material may be selected from the group consisting of polyolefins; polyesters; polyethers; polyketones; polyamides; natural and synthetic rubbers; polyurethanes; polystyrenes; high-impact polystyrenes; polyacrylates; polymethacrylates; polyacetals; polyacrylonitriles; polybutadienes; polystyrenes; ABS; SAN (styrene acrylonitrile); ASA (acrylate styrene acrylonitrile); cellulosic acetate butyrate; cellulosic polymers; polyimides; polyamideimides; polyetherimides; polyphenylsulfides; PPO; polysulfones; polyethersulfones; polyvinylchlorides; polycarbonates; polyketones; aliphatic polyketones; thermoplastic TPO's; aminoresin crosslinked polyacrylates and polyesters; polyisocyanate crosslinked polyesters and polyacrylates; phenol/formaldehyde, urea/formaldehyde, and melamine/formaldehyde resins; drying and non-drying alkyd resins; alkyd resins; polyester resins; acrylate resins cross-linked with melamine resins, urea resins, isocyanates, isocyanurates, carbamates, and epoxy resins; cross-linked epoxy resins derived from aliphatic, cycloaliphatic, heterocyclic and aromatic glycidyl compounds which are cross-linked with anhydrides or amines; polysiloxanes; Michael addition polymers of amines or blocked amines with activated unsaturated and methylene compounds, ketimines with activated unsaturated and methylene compounds, polyketimines in combination with unsaturated acrylic polyacetoacetate resins, and polyketimines in combination with unsaturated acrylic resins; radiation curable compositions; epoxymelamine resins; organic dyes; cosmetic products; cellulose-based paper formulations; photographic film paper; ink; and blends thereof. The one or more compounds may be incorporated into the polymer by chemical bonding during and/or subsequent to the preparation of the polymer.

In one embodiment of the method, the material to be stabilized has one or more surfaces and the stabilizer composition is applied to the one or more surfaces of the material. The stabilizer composition may be part of a coating and the method may involve applying the coating to the at least one surface of the material. The material may be metallic, wood, ceramic, polymeric, or a fiber material.

The method may further comprise the step of chemically bonding the one or more compounds to the material and forming the material into a fiber. The material may be silk, leather, wool, polyamide, polyurethane, cellulose-containing fibers, and blends thereof.

The material to be stabilized may also be a photographic material or a cosmetic composition.

The invention also relates to a compound of formula (XXXII)

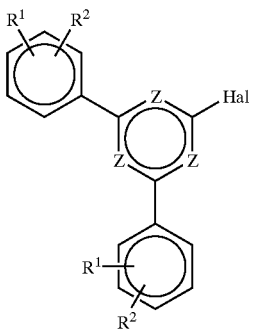

(XXXII)

wherein each Z is independently nitrogen or methine, and at least two Z are nitrogen, to form a triazine or pyrimidine ring;

each $R^1$ and $R^2$ is identical or different and is independently a hydrocarbyl group of between 1 and 20 carbons, wherein $R^1$ and $R^2$ are attached to an aromatic benzene ring so that they are ortho to each other, and Hal is a halogen.

DETAILED DESCRIPTION OF THE PREFERRED EMBODIMENTS

The invention provides a new class of triazine and pyrimidine ultraviolet light absorbers containing a phenolic aromatic group(s) and non-phenolic aromatic group(s), wherein the non-phenolic aromatic groups are substituted with at least two hydrocarbyl groups that are ortho to each other. The triazine and pyrimidine ultraviolet light absorbers of the invention can be monomeric or oligomeric.

The triazine and pyrimidine ultraviolet light absorbers of the invention, with ortho di-hydrocarbyl substituted aromatic rings, have the advantage of being highly soluble in and compatible with many polymers and coatings while being stable to environmental degradation that has led previous UV stabilizers to turn yellow and degrade with respect to performance as UV stabilizers. Without wishing to be bound by theory it is believed that the improved solubility and compatibility of the triazines and pyrimidines of the invention is due to the presence of hydrocarbyl groups on the non-phenolic aromatic rings. It is, however, well known that triazines and pyrimidines that have hydrocarbyl groups on the non-phenolic aromatic rings are more prone to yellowing than triazines and pyrimidines without hydrocarbyl groups. The yellowing of triazines and pyrimidines having hydrocarbyl groups on the non-phenolic aromatic rings is attributed to oxidation of the hydrocarbyl groups. Thus, many triazines and pyrimidines avoid having hydrocarbyl groups on the non-phenolic aromatic rings even though thay have superior solubility and compatibility with many polymers. Surprisingly, however, it was found that triazines and pyrimidines having-hydrocarbyl groups on the non-phenolic aromatic rings-that are ortho to each other are less prone to thermal yellowing and yellowing on exposure to UV light compared to triazines and pyrimidines having hydrocarbyl groups on the aromatic rings that are not ortho to each other. Even more surprising is the discovery that, the performance of the triazines and pyrimidines of the invention at inhibiting thermal degradation and UV degradation is similar or superior to triazines or pyrimidines without hydrocarbyl groups on the aromatic rings.

The triazine and pyrimidine ultraviolet light absorbers have the following general structure (1):

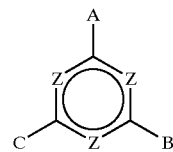

(I)

wherein Z can be a nitrogen or a methine and at least two Z are nitrogen, to form a pyrimidine or triazine ring; A is an aromatic benzene ring substituted with two hydrocarbyl groups that are ortho to each other; B is a resorcinol radical bound by a cyclic carbon atom directly to the pyrimidine or triazine ring; and C can be either A or B. Preferably C is A. Preferably each Z is a nitrogen.

More specifically, the new triazine and pyrimidine ultraviolet light absorbers having di-ortho alkyl substituted aromatic rings have the formula (II):

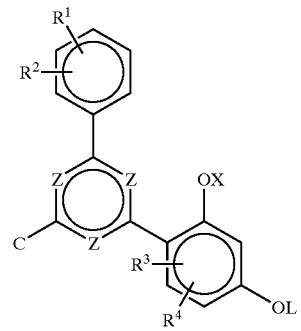

(II)

wherein each Z is independently nitrogen or methine, and at least two Z are nitrogen;

X is independently selected from hydrogen and a blocking group;

C is either

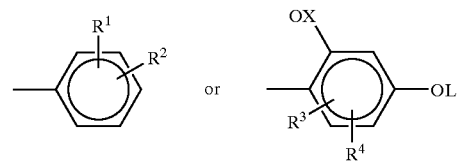

each of L is independently a hydrogen, hydrocarbyl, —SO$_2$(hydrocarbyl), —SO$_3$(hydrocarbyl), —SO$_2$(functional hydrocarbyl), —SO$_3$(functional hydrocarbyl), —COO(hydrocarbyl), COO(functional hydrocarbyl), CO(hydrocarbyl), CO(functional hydrocarbyl), —OCO(hydrocarbyl), —OCO(functional hydrocarbyl), —CONH$_2$, —CONH(hydrocarbyl), —CONH(functional hydrocarbyl), —CON(hydrocarbyl)(hydrocarbyl), —CON(functional hydrocarbyl)(hydrocarbyl), —CON(functional hydrocarbyl)(functional hydrocarbyl), or a hydrocarbyl group substituted by any of the above groups;

each of $R^3$ and $R^4$ are independently a hydrogen, hydrocarbyl, halogen, hydroxyl, cyano, —O(hydrocarbyl), —O(functional hydrocarbyl), —N(hydrocarbyl)(hydrocarbyl), —N(hydrocarbyl)

(functional hydrocarbyl), —N(functional hydrocarbyl)(functional hydrocarbyl), —S(hydrocarbyl), —S(functional hydrocarbyl), —SO$_2$(hydrocarbyl), —SO$_3$(hydrocarbyl), —SO$_2$(functional hydrocarbyl), —SO$_3$(functional hydrocarbyl), COO(hydrocarbyl), —COO(functional hydrocarbyl), —CO(hydrocarbyl), —CO(functional hydrocarbyl), —OCO(hydrocarbyl), —OCO(functional hydrocarbyl), —CONH$_2$, —CONH(hydrocarbyl), —CONH(functional hydrocarbyl), —CON(hydrocarbyl)(hydrocarbyl), —CON(functional hydrocarbyl)(hydrocarbyl), —CON(functional hydrocarbyl)(functional hydrocarbyl), or a hydrocarbyl group substituted by any of the above groups.

Preferably, L is selected from the group consisting of hydrogen, $C_1$–$C_{24}$ alkyl or mixtures thereof; $C_1$–$C_{24}$ branched alkyl or mixtures thereof; $C_3$–$C_6$ alkenyl; —COR$^{12}$; —COOR$^{12}$; —CONHR$^{12}$; —SO$_2$R$^{13}$; $C_1$–$C_{18}$ alkyl which is substituted with one or more of the groups:

hydroxy, $C_1$–$C_{18}$ alkoxy, $C_3$–$C_{18}$ alkenoxy, halogen, phenoxy, $C_1$–$C_{18}$ alkyl-substituted phenoxy, $C_1$–$C_8$ alkoxy-substituted phenoxy, halogen-substituted phenoxy, —COOH, —COOR$^9$, CONH$_2$, —CONHR$^9$, —CON(R$^9$)(R$^{10}$), —NH$_2$, —NHR$^9$, —N(R$^9$)R$^{10}$), —NHCOR$^{11}$, N(R$^9$)COR$^{11}$, —NHCOOR$^{11}$, —N(R$^9$)COOR$^{11}$, —CN, —OCOR$^{11}$, —OC(O)NHR$^9$, —OC(O)N(R$^9$)(R$^{10}$), $C_2$–$C_{50}$ alkyl which is interrupted by one or more oxygen atoms or carbonyl groups and optionally substituted by one or more substituents selected from the group consisting of hydroxy, $C_1$–$C_{12}$ alkoxy, and glycidyloxy; glycidyl; and cyclohexyl optionally substituted with hydroxyl or —OCOR$^{11}$.

R$^9$ and R$^{10}$ independently of one another are $C_1$–$C_{12}$ alkyl, $C_3$–$C_{12}$ alkoxyalkyl, $C_4$–$C_{16}$ dialkylaminoalkyl, or $C_5$–$C_{12}$ cycloalkyl, or R$^9$ and R$^{10}$ taken together are $C_3$–$C_9$ alkylene or $C_3$–$C_9$ oxoalkylene or $C_3$–$C_9$ azaalkylene.

R$^{11}$ is $C_1$–$C_{18}$ alkyl, $C_2$–$C_{18}$ alkenyl, or phenyl.

R$^{12}$ is $C_1$–$C_{18}$ alkyl, $C_2$–$C_{18}$ alkenyl, phenyl, $C_1$–$C_{12}$ alkoxy, phenoxy, $C_1$–$C_{12}$ alkylamino, phenylamino, tolylamino or naphthylamino, and R$^{13}$ is $C_1$–$C_{12}$ alkyl, phenyl, naphthyl or $C_7$–$C_{14}$ alkylphenyl.

Some of these groups as well as others are described in U.S. Pat. No. 5,106,891, U.S. Pat. No. 5,189,084, U.S. Pat. No. 5,356,995, U.S. Pat. No. 5,637,706, U.S. Pat. No. 5,726,309, EP 434,608, EP 704,437, WO 96/28431, and GB 2,293,823 which are incorporated herein by reference for all purposes as if fully set forth.

In another embodiment, L in formula (II) is selected from the group consisting of hydrogen; an alkyl of 1 to 24 carbon atoms optionally substituted by one or more hydroxyl, alkoxy, carboxy, carboalkoxy, amino, amido, carbamato, or epoxy groups, and which may contain one or more carbonyl groups, oxygen atoms or nitrogen atoms in the chain; an alkenyl of 2 to 24 carbon atoms optionally substituted by hydroxyl, alkoxy, carboxy, carboalkoxy, amino, amido, carbamato, or epoxy groups and which may contain one or more carbonyl groups, oxygen atoms or nitrogen atoms in the chain or attached to the chain; a cycloalkyl of 5 to 24 carbon atoms optionally substituted by hydroxyl, carboxyl, or amino groups and optionally containing carbonyl, oxygen, or nitrogen in the ring; an aralkyl of 7 to 24 carbon atoms optionally substituted by one or more hydroxyl, alkoxy, chloro, cyano, carboxy, carboalkoxy, amino, amido, carbamato, or epoxy groups and may contain one or more carbonyl groups, oxygen atoms or nitrogen atoms in the ring;

a polyoxyalkylene radical of the formula XII

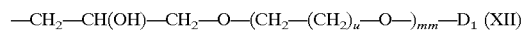

wherein D$_1$ is hydrogen,

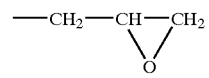

—CH$_2$—CH(OH)—CH$_2$—OH, or R$^{25}$;

a polyoxyalkylene radical of the formula XIII

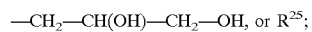

wherein D$_2$ is —(CH$_2$)$_u$—CO—R$^{22}$ or R$^{25}$;

a polyoxyalkylene radical of the formula XIV

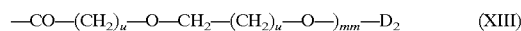

wherein D$_3$ is —(CH$_2$)$_u$—CO—R$^{22}$ or R$^{21}$;

a polyoxyalkylene radical of the formula XV

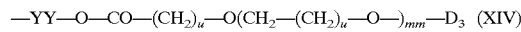

wherein D$_4$ is hydrogen of R$^{25}$;

a polyoxyalkylene radical of the formula XVI

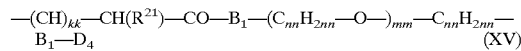

wherein D, is —NH$_2$, —NH—(CH$_2$)$_2$—COO—R$^{23}$ or —O—R$^{25}$;

a polyoxyalkylene radical of the formula XVII

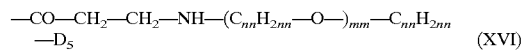

wherein D$_5$ is as defined under formula (XVI);

a polyoxyalkylene radical of the formula XVIII

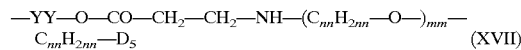

wherein D$_6$ is —NH—CO—R$^{24}$, —OR$^{25}$, OH or H; a polyoxyalkylene radical of the formula XIX

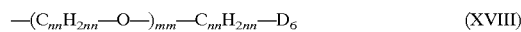

wherein D$_7$ is —OR$^{25}$, —NHCOR$^{24}$ or —OCH$_2$CH$_2$OR$^{25}$;

R$^{21}$ is hydrogen or $C_1$–$C_{16}$ alkyl;

R$^{17}$ is $C_2$–$C_{10}$ alkylene, phenylene, naphthylene, diphenylene, or $C_2$–$C_6$ alkenylene, methylenediphenylene, or $C_4$–$C_{15}$ alkylphenylene;

R$^{21}$ is hydrogen or $C_1$–$C_{16}$ alkyl;

R$^{22}$ is halogen or —O—R$^3$;

R$^{23}$ is hydrogen, $C_1$–$C_6$ alkyl, $C_3$–$C_6$ alkenyl, aryl, or aryl-$C_1$–$C_4$-alkyl;

R$^{24}$ is hydrogen, $C_1$–$C_{12}$ alkyl or aryl;

R$^{25}$ is $C_1$–$C_{16}$ alkyl, $C_5$–$C_{12}$ cycloalkyl, $C_3$–$C_6$ alkenyl, $C_1$–$C_{12}$ alkylaryl or aryl-$C_1$–$C_4$ alkyl;

YY is unsubstituted or substituted $C_2$–$C_{20}$ alkyl;

$B_1$ is HN or O;

kk is zero or an integer from 1–16;

mm is an integer from 2 to 60;

nn is an integer from 2 to 6;

u is an integer from 1 to 4;

L may also be an alkyl of 1–24 carbon atoms substituted by a hindered amine light satabilizer (HALS) of the general formula (VI). Triazines containing tetramethylpiperidine groups are described in U.S. Pat. No. 4,161,592 and U.S. Pat. No. 5,376,710 which are incorporated herein by reference for all purposes as if fully set forth.

(VI)

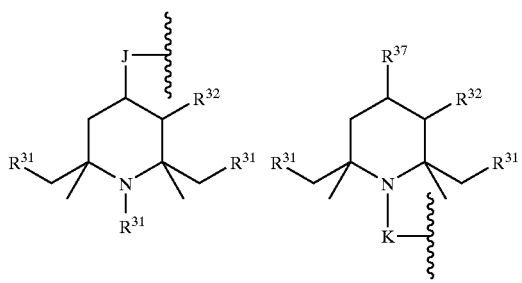

wherein

J is —O—, —$NR^{30}$—, —T—$(CH_2)_2$—$NR^{30}$— wherein T is —O— or —S—, and $R^{30}$ is $C_1$–$C_{12}$ alkyl or hydrogen;

$R^{31}$ is hydrogen or $C_1$–$C_8$ alkyl;

$R^{32}$ is hydrogen, oxygen, $C_1$–$C_{21}$ alkoxyalkyl, $C_7$–$C_8$ aralkyl, 2,3-epoxypropyl, and aliphatic acyl group with 1–4 C atoms or one of the groups —$CH_2COOR^{33}$, —$CH_2$—$CH(R^{34})$—$OR^{35}$—, —$COOR^{36}$ or —$CONHR^{36}$, wherein $R^{33}$ is $C$—$C_2$ alkyl $C_3$–$C_6$ alkenyl, phenyl, $C_7$–$C_8$ aralkyl or cyclohexyl, $R^{34}$ is a hydrogen, methyl or phenyl, $R^{35}$ is hydrogen, an aliphatic, aromatic, araliphatic or alicyclic acyl group with 1–8 C atoms, wherein the aromatic part is unsubstituted or is substituted by chlorine, $C_1C_4$ alkyl, $C_1$–$C_8$ alkoxy or by hydroxyl, and $R^{36}$ is $C_1$–$C_{12}$ alkyl, cyclohexyl, phenyl or benzyl;

$R^{37}$ is hydrogen, AH or one of the groups —O—CO—$R^{38}$ or —$NR^{36}$—CO—$R^{38}$, wherein $R^{38}$ is $C_1$–$C_{12}$ alkyl or phenyl; and K is —O—$(C_{mm}H_{2mm})$— wherein mm is 1 to 6.

In the preferred embodiment L is selected from an alkyl chain of between 1 and 20 carbons, preferably between 1 and 10 carbons. The alkyl chain may optionally be interrupted by one or more oxygen atoms or may have one or more of the hydrogens substituted for by a hydroxyl group. Optionally, the alkyl chain may also terminate with a carbonyl functionality of general structure —CO—M, wherein M is an alkoxy group (i.e., an ester) having between 1 and 8 carbons; $NR^xR^y$ (i.e., an amide), wherein $R^x$ and $R^y$ are independently hydrogen or an alkyl group of between 1 and 8 carbons that optionally may have one or more of the hydrogens substituted for by a hydroxyl group; or OH (i.e., a carboxylic acid).

These preferred L groups are readily attached to the phenolic oxygen by reacting a compound of formula II, wherein L is hydrogen with the desired alkyl halide (or other leaving group), preferably under basic conditions. Compounds wherein L is an alkyl chain that terminates with a carbonyl functionality that is an amide or ester are typically prepared by reacting a carboxylic acid having a good leaving group, for example a halide, in the alkyl group to provide a compound of formula II wherein the alkyl chain terminates in COOH and then converting the carboxylic acid to an amide or ester by any method available to those of ordinary skill in the art. Methods for converting a carboxylic acids to an amide or ester are well known to those of ordinary skill in the art.

In one embodiment $R^3$ and $R^4$ is independently selected from hydrogen, halogen, a hydrocarbyl group of 1 to 24 carbon atoms, a hydrocarbyloxy group of 1 to 24 carbon atoms, an acyl group of 2 to 24 carbon atoms, an acyloxy group of 2 to 24 carbon atoms, and —OR.

In another embodiment each $R^3$ and $R^4$ is independently selected from hydrogen, an alkyl of 1 to 24 carbon atoms optionally containing an oxygen atom in the chain; an alkyloxy of 1 to 24 carbon atoms; an alkenyl of 2 to 24 carbon atoms (which may optionally be substituted by hydroxyl, carboxyl and/or amino group(s) and/or contain carbonyl, oxygen and/or nitrogen in the chain); an alkenyloxy of 2 to 24 carbon atoms (which may optionally be substituted by hydroxyl, carboxyl and/or amino group(s) and/or contain carbonyl, oxygen and/or nitrogen in the chain); a cycloalkyl of 5 to 12 carbon atoms (which may optionally be substituted by hydroxyl, carboxyl and/or amino group(s) and/or contain carbonyl, oxygen and/or nitrogen in the ring); an acyl group of 2 to 12 carbon atoms.

In another embodiment, $R^3$ and $R^4$ are independently methylene or alkylidene substituted by a benzophenone UV absorber or a benzotriazole UV absorber. Related triazine-benzotriazole and triazine-benzophenone hybrid UV absorbers are disclosed in U.S. Pat. No. 5,585,422 which is incorporated by reference herein for all purposes as if fully set forth. In a related embodiment, $R^3$ and $R^4$ are independently methylene, alkylidene, or benzylidene substituted by a second UV absorber. Related triazine dimers (and oligomers) are disclosed in U.S. Pat. No. 5,726,309 and EP 704,437 which are incorporated by reference herein for all purposes as if fully set forth.

Preferably each $R^3$ and $R^4$ is independently selected from hydrogen, an alkyl of 1 to 8 carbons, more preferably 1 to 4 carbon atoms, wherein optionally one or more of the hydrogens in the alkyl chain are substituted for with the nitrogen of an amine. Methods for adding an alkyl group wherein one or more of the hydrogens in the alkyl chain are substituted for with the nitrogen of an amine are described in WO 99/67224, the contents of which are expressly incorporated herein.

In preferred embodiments, each X is hydrogen. When X is a blocking group it is preferred that X is $COR^a$, —$SO_2R^b$, —$SiR^cR^dR^e$, wherein $R^a$ and $R^b$, $R^c$, $R^d$, and $R^e$ are alkyl chains of up to 8 carbons, benzene, or a benzene substituted with one or more groups commonly found in organic molecules.

Each $R^1$ and $R^2$ is identical or different and is independently a hydrocarbyl group of between 1 and 20 carbons, preferably between 1 and 10 carbons, and most preferably between 1 and 5 carbons, wherein $R^1$ and $R^2$ are attached to the aromatic ring so that they are ortho to each other. The alkyl group may be a straight chain, branched-chain, or cyclic alkyl group. Preferably the alkyl group is a straight chain alkyl group, $R^1$ and $R^2$ may be attached to the aromatic ring so that they are attached to the 2 and 3 positions or the 3 and 4 positions of the aromatic benzene ring relative to the point of attachment of the triazine or pyrimidine ring.

Preferably $R^1$ and $R^2$ are attached to the 3 and 4 positions of the aromatic benzene ring relative to the point of attachment of the triazine or pyrimidine ring. In one embodiment each $R^1$ and $R^2$ is a methyl group.

Optionally, the hydrocarbyl group can have one or more of the hydrogens in the chain replaced by a substituent commonly found in organic molecules. Preferably the hydrocarbyl group is attached to the benzene ring by a saturated carbon. Optionally, one or more of the hydrogens on the aromatic benzene ring can also be replaced by a hydrocarbyl group or substituent commonly found in organic molecules. Preferably, the hydrogens are not substituted.

Preferably C is an aromatic benzene ring having two hydrocarbyl groups that are ortho to each other. When C is also an aromatic benzene ring both aromatic rings can have the two hydrocarbyl groups that are ortho to each other in the 2 and 3 positions relative to the point of attachment of the triazine or pyrimidine ring, or both rings can have the two hydrocarbyl groups that are ortho to each other in the 3 and 4 positions relative to the point of attachment of the triazine or pyrimidine ring. Alternatively, one aromatic ring can have the two hydrocarbyl groups that are ortho to each other in the 2 and 3 positions relative to the point of attachment of the triazine or pyrimidine ring and the other aromatic ring can have the two hydrocarbyl groups that are ortho to each other in the 3 and 4 positions relative to the point of attachment of the triazine or pyrimidine ring. Preferably, both rings have the two hydrocarbyl groups that are ortho to each other in the 3 and 4 positions relative to the point of attachment of the triazine or pyrimidine ring.

The pyrimidines and triazines of the present invention further comprise oligomeric species. Preferably, the oligomeric species have the formulas (Im), (IV) and (V):

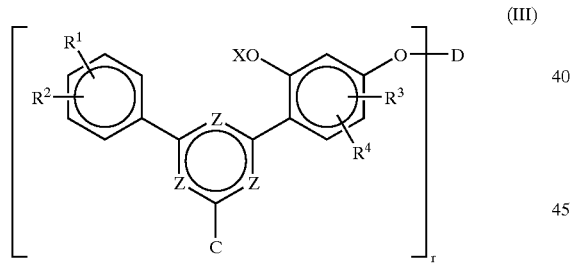

(III)

wherein

Z, C, $R^1$, $R^2$, $R^3$, $R^4$, and X, are as defined above;

r is an integer between 2 and 4;

D can be a wide variety of groups;

D, when r is 2, is selected from the group consisting of $C_1$–$C_{16}$ alkylene, $C_4$–$C_{12}$ alkenylene, xylylene, $C_4$–$C_{20}$ alkylene which is interrupted by one or more oxygen atoms, hydroxy-substituted $C_3$–$C_{20}$ alkyl which is interrupted by one or more oxygen atoms, —$CH_2CH(OH)CH_2O$—$R^{15}$—$OCH_2CH(OH)CH_2$—, —CO—$R^{16}$—CO—, —CO—NH—$R^{17}$—NH—CO—, —$(CH_2)_s$—COO—$R^{18}$—OCO—$(CH_2)_s$— a polyoxyalkylene bridge member of the formula XX

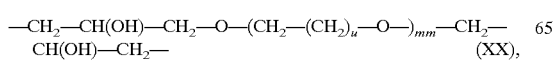

a polyoxyalkylene bridge member of the formula XXI

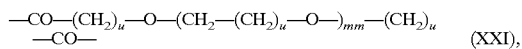

a polyoxyalkylene bridge member of the formula XXII

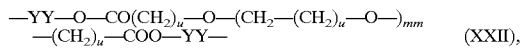

a polyoxyalkylene bridge member of the formula XXIII

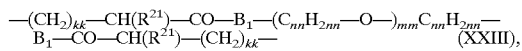

a polyoxyalkylene bridge member of the formula XXIV

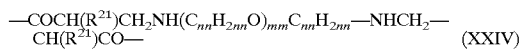

a polyoxyalkylene bridge member of the formula XXV

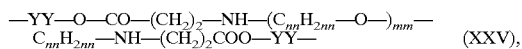

a polyoxyalkylene bridge member of the formula XXVI

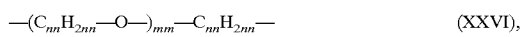

and a polyoxyalkylene bridge member of the formula XXVII

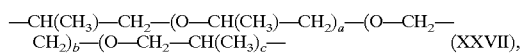

wherein a+c=2.5 and b=8.5 to 40.5 or a+c=2 to 33 and b=0, $R^{15}$ is $C_2$–$C_{10}$ alkylene, $C_2$–$C_{10}$ oxaalkylene or $C_2$–$C_{10}$ dithiaalkylene, phenylene, naphthylene, diphenylene, or $C_2$–$C_6$ alkenylene, or phenylene-XX-phenylene wherein XX is —O—, —S—, $SO_2$—, —$CH_2$—, or —$(CH_3)_2$—;

$R^{16}$ is $C_2$–$C_{10}$ alkylene, $C_2$–$C_{10}$ oxaalkylene or $C_2$–$C_{10}$ dithiaalkylene, phenylene, naphthylene, diphenylene, or $C_2$–$C_6$ alkenylene provided that when r is 3 the alkenylene has at least 3 carbons;

$R^{17}$ is $C_2$–$C_{10}$ alkylene, phenylene, naphthylene, diphenylene, or $C_2$–$C_6$ alkenylene, methylenediphenylene, or $C_4$–$C_{15}$ alkylphenylene; and $R^{18}$ is $C_2$–$C_{10}$ alkylene, or $C_4$–$C_{20}$ alkylene interrupted by one or more oxygen atoms;

$R^{21}$ is hydrogen or $C_1$–$C_{16}$ alkyl;

YY is unsubstituted or substituted $C_2$–$C_{20}$ alkyl;

$B_1$ is NH or O;

kk is zero or an integer from 1–16;

mm is an integer from 2 to 60;

nn is an integer from 2 to 6;

u is an integer from 1 to 4;

when r is 3, D is

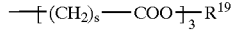

and when r is 4, D is

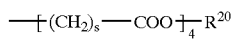

wherein $R^{19}$ is $C_3$–$C_{10}$ alkanetriyl and $R^{20}$ is $C_4$–$C_{10}$ alkanetetryl; and s is 16.

Preferably, in structure III r is 2 and D is an alkyl chain of between 1 and 10 carbons, preferably between 1 and 8 carbons, or —CO—P—CO—, wherein P is an alkyl chain of between 1 and 10 carbons, preferably between 1 and 8 carbons, or an aromatic ring, preferably a benzene ring and preferably wherein the carbonyl groups are meta or para to each other. The dimeric structure can readily be made by reacting the compound of structure III, wherein L is hydrogen, with an alkyl chain of between 1 and 10 carbons, preferably between 1 and 8 carbons, that is substituted on each end with a good leaving group, such as a halide, or with a diacid chloride of structure Cl—CO—P—CO—Cl.

Another dimeric structure is represented by structure IV.

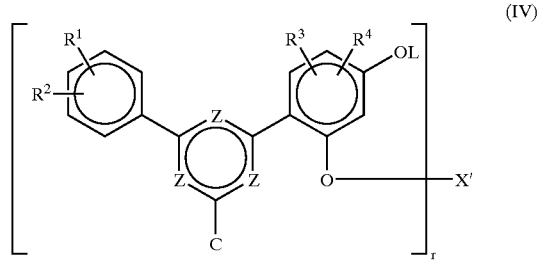

(IV)

wherein

Z, C, $R^1$, $R^2$, $R^{3,}$ $R^4$, and L, are as defined above; r is an integer between 2 and 4;

X' can be a wide variety of groups;

X', when r is 2, is selected from the group consisting of $C_1$–$C_{16}$ alkylene, $C_4$–$C_{12}$ alkenylene, xylylene, $C_4$–$C_{20}$ alkylene which is interrupted by one or more oxygen atoms, hydroxy-substituted $C_3$–$C_{20}$ alkyl which is interrupted by one or more oxygen atoms, —CH$_2$CH(OH)CH$_2$O—$R^{15}$—OCH$_2$CH(OH)CH$_2$—, —CO—$R^{16}$—CO—, —CO—NH—$R^{17}$—NH—CO—, —(CH$_2$)$_s$—COO—$R^{18}$—OCO—(CH$_2$)$_s$— a polyoxyalkylene bridge member of the formula XX

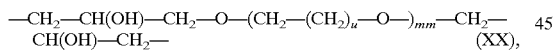

(XX), a polyoxyalkylene bridge member of the formula XXI

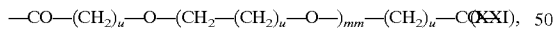

(XXI), a polyoxyalkylene bridge member of the formula XXII

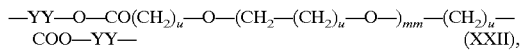

(XXII), a polyoxyalkylene bridge member of the formula XXIII

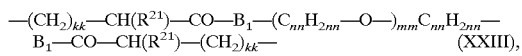

(XXIII), a polyoxyalkylene bridge member of the formula XXIV

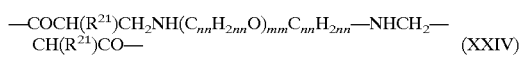

(XXIV), a polyoxyalkylene bridge member of the formula XXV

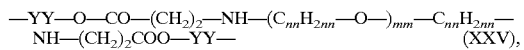

(XXV), a polyoxyalkylene bridge member of the formula XXVI

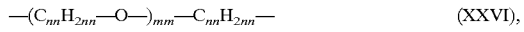

(XXVI), and a polyoxyalkylene bridge member of the formula XXVII

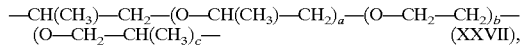

(XXVII), wherein a+c=2.5 and b=8.5 to 40.5 or a+c=2 to 33 and b=0, $R^{15}$ is $C_2$–$C_{10}$ alkylene, $C_2$–$C_{10}$ oxaalkylene or $C_2$–$C_{10}$ dithiaalkylene, phenylene, naphthylene, diphenylene, or $C_2$–$C_6$ alkenylene, or phenylene-XX-phenylene wherein XX is —O—, —S—, —SO$_2$—, —CH$_2$—, or —C(CH$_3$)$_2$—;

$R^{16}$ is $C_2$–$C_{10}$ alkylene, $C_2$–$C_{10}$ oxaalkylene or $C_2$–$C_{10}$ dithiaalkylene, phenylene, naphthylene, diphenylene, or $C_2$–$C_6$ alkenylene provided that when r is 3 the alkenylene has at least 3 carbons;

$R^{17}$ is $C_2$–$C_{10}$ alkylene, phenylene, naphthylene, diphenylene, or $C_2$–$C_6$ alkenylene, methylenediphenylene, or $C_4$–$C_{15}$ alkylphenylene; and $R^{18}$ is $C_2$–$C_{10}$ alkylene, or $C_4$–$C_{20}$ alkylene interrupted by one or more oxygen atoms;

$R^{21}$ is hydrogen or $C_1$–$C_{16}$ alkyl;

YY is unsubstituted or substituted $C_2$–$C_{20}$ alkyl;

$B_1$ is NH or O;

kk is zero or an integer from 1–16;

mm is an integer from 2 to 60;

nn is an integer from 2 to 6;

s is 1–6;

u is an integer from 1 to 4;

when r is 3, D is

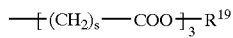

and when r is 4, D is

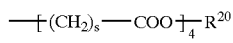

wherein $R^{19}$ is $C_3$–$C_{10}$ alkanetriyl and $R^{20}$ is $C_4$–$C_{10}$ alkanetetryl.

Preferably r is 2 and X' is an alkyl chain of between 1 and 10 carbons, preferably between 1 and 8 carbons, or —CO—P—CO—, wherein P is an alkyl chain of between 1 and 10 carbons, preferably between 1 and 8 carbons, or an aromatic ring preferably a benzene ring and preferably wherein the carbonyl groups are meta or para to each other. The dimeric structure can readily be made by reacting the compound of structure III, wherein L is not hydrogen, and may be a removable protecting group, such as, but not limited to COR$^a$, SO$_2$R$^b$, SiR$^c$R$^d$R$^e$, wherein R$^a$ and R$^b$, R$^c$, R$^d$, and R$^e$ are alkyl chains of up to 8 carbons, benzene or a substituted benzene, and X is a hydrogen, with an alkyl chain of between 1 and 10 carbons, preferably between 1 and 8 carbons, that is substituted on each end with a good leaving group, such as a halide, or with a diacid chloride of structure Cl—CO—P—CO—Cl.

Another dimeric structure is represent by structure V.

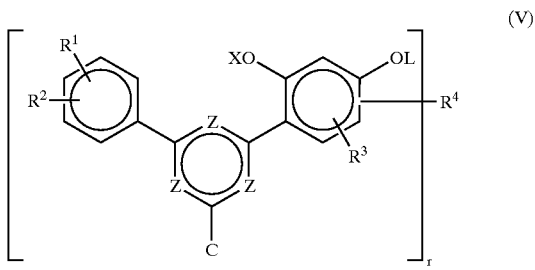

(V)

wherein Z, $R^1$, $R^2$, $R^3$, L and X, are as defined above; r is 2; C is as defined above, and $R^4$ can be a wide variety of groups;

$R^4$ is selected from the group consisting of straight chain alkyl of 1 to 12 carbon atoms, branched chain alkyl of 1 to 12 carbon atoms, cycloalkyl of 5 to 12 carbon atoms, alkyl substituted by cyclohexyl, alkyl interrupted by cyclohexyl, alkyl substituted by phenylene, alkyl interrupted by phenylene, benzylidene, —S—, —S—S—, —S—E—S—, —SO—, —SO$_2$—, —SO—E—SO—, —SO$_2$—E—SO$_2$—, —CH$_2$—NH—E—NH—CH$_2$—, and

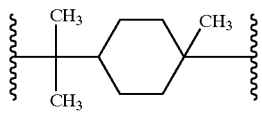

wherein E is selected from the group consisting of alkyl of 2 to 12 carbon atoms, cycloalkyl of 5 to 12 carbon atoms, alkyl interrupted by cyclohexyl of 8 to 12 carbon atoms, alkyl terminated by cyclohexyl of 8 to 12 carbon atoms.

These compounds can be prepared by any means available to one of ordinary skill in the art. Preferably, they are prepared by the method disclosed in WO 99/67227.

Preferably r is 2 and $R_4$ is —CH$_2$—. Compounds wherein r is 2 and R is —CH$_2$— can readily be made by any method available to those of ordinary skill in the art, the preferred method is the method disclosed in WO 99/67224 the contents of which are expressly incorporated herein.

The pyrimidines and triazines of the present invention further comprise a compound of formula (XXXIV):

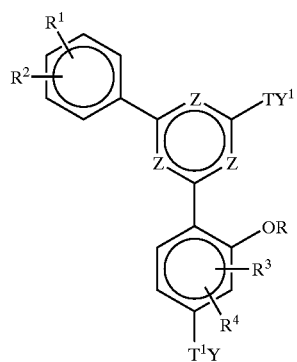

(XXXIV)

wherein

Z, X, $R^1$, $R^2$, $R^3$, and $R^4$ are as defined above;

each of T and T' is independently a direct bond, carbon, oxygen, nitrogen, sulfur, phosphorous, boron, silicon, or functional groups containing these elements;

is each of Y and Y' are independently one or more of a hydrogen, hydrocarbyl group, a functional hydrocarbyl group, halogen, hydroxyl, cyano, —O(hydrocarbyl), —O(functional hydrocarbyl), —N(hydrocarbyl)(hydrocarbyl), —N(functional hydrocarbyl)(functional hydrocarbyl), —N(hydrocarbyl)(functional hydrocarbyl), —S(hydrocarbyl), —S(functional hydrocarbyl), —SO$_2$(hydrocarbyl), —SO$_2$(hydrocarbyl), —SO$_3$(hydrocarbyl), —SO$_3$(functional hydrocarbyl), —COO(hydrocarbyl), —COO(functional hydrocarbyl), —CO(hydrocarbyl), —CO(functional hydrocarbyl, —OCO(hydrocarbyl), —OCO(functional hydrocarbyl), —N(hydrocarbyl)(hydrocarbyl), —CONH$_2$, —CONH(hyrdocarbyl), —CONH(functional hyrdocarbyl), —CON(hydrocarbyl)(hyrdocarbyl), —CON(hydrocarbyl)(functional hyrdocarbyl), —CON(functional hydrocarbyl)(functional hyrdocarbyl), —S(functional hydrocarbyl), —SO$_2$(functional hydrocarbyl), —SO$_3$(functional hydrocarbyl), —COO(functional hydrocarbyl), —CO(functional hydrocarbyl), —OCO(functional hydrocarbyl), or a hydrocarbyl group substituted by any of the above groups.

Typically, the compounds of formula (II) to (V) or (XXXIV) are added to polymeric materials to inhibit or prevent one or more of thermal or photo-degradation or to protect from the effects of ultraviolet light by screening. By screening is meant that the compounds are included in a protective composition to filter ultraviolet light. The protective composition may be, for example, a cosmetic preparation or a glass or plexiglass window. Therefore, it is preferable that one or more of $R^1$, $R^2$, $R^3$, $R^4$, L, D, or X' is chosen so as to improve the solubility of the compound of formula (II) to (V) or (XXXIV) in the polymeric material to which it is to be added. One of ordinary skill in the art can readily recognize what structures for $R^1$, $R^2$, $R^3$, $R^4$, L, D, or X' would improve solubility in a given polymeric material. For example, it is often preferable, that $R^1$, $R^2$, $R^3$, $R^4$, L, D, or X' is similar to, i.e., has the same functional groups, as the monomeric units of the polymeric material.

The substituted pyrimidines and triazines of the invention may optionally have the added benefit of being capable of being chemically bonded to appropriate polymer systems via a functionality attached to the alkylphenyl or pyrimidine or triazine groups (e.g., by a hydroxyl, ethylenic unsaturated and/or activated unsaturated group in one or more of $R^1$, $R^2$, $R^3$, $R^4$, Y, or Y').

The term "hydrocarbyl" in the context of the present invention, and in the above formulas, broadly refers to a monovalent hydrocarbon group in which the valency is derived by abstraction of a hydrogen from a carbon atom. Hydrocarbyl includes, for example, aliphatics (straight and branched chain), cycloaliphatics, aromatics and mixed character groups (e.g., aralkyl and alkaryl). Hydrocarbyl also includes such groups with internal unsaturation and activated unsaturation. More specifically, hydrocarbyl includes, but is not limited to, such groups as alkyl, cycloalkyl, aryl, aralkyl, alkaryl, alkenyl, cycloalkenyl and alkynyl, preferably having up to 24 carbon atoms. A hydrocarbyl chain or ring may optionally be interrupted by one or more carbonyl groups (which is/are included in the carbon count) and/or heteroatoms (such as at least one oxygen, sulfur, nitrogen or silicon). A hydrocarbyl group may also have one or more hydrogens replaced with a substituent commonly found in organic molecules.

The phrase "substituent commonly found in organic molecules," as used herein means non-hydrocarbyl groups that are typically found in organic molecules including, but not limited to, halides, cyano groups, amino groups, thiol groups, carboxylate groups, hydroxyl groups, sulfonate groups, nitroso groups, nitro groups, and the like.

The term "functional hydrocarbyl" in the context of the present invention, and in the above formulas, broadly refers to a hydrocarbyl possessing pendant and/or terminal reactive and/or latent reactive functionality and/or leaving groups.

The term "reactive" functionality refers to functionality that is reactive with common monomer/polymer functionalites under normal conditions well understood by those of ordinary skill in the relevant art. As non-limiting examples of a reactive functionality may be mentioned active hydrogen containing groups such as hydroxyl, amino, carboxyl, thio, amido, carbamoyl, and activated methylene; isocyanato; cyano; epoxy; ethylenically unsaturated groups such as allyl and methallyl; and activated unsaturated groups such acryloyl and methacryloyl, and maleate and maleimido (including the Diels-Alder adducts thereof with dienes such as butadiene).

The term "latent reactive" functionality within the meaning of the present invention and, as would clearly be understood by those persons of ordinary skill in the art, refers to reactive functionality which is blocked or masked to prevent premature reaction. As examples of a latent reactive functionality may be mentioned ketimines and aldimines (amines blocked, respectively, with ketones and aldehydes); amine-carboxylate salts; and blocked isocyanates such as alcohol (carbamates), oxime, and caprolactam blocked variations.

A "leaving" group within the meaning of the present invention, as would clearly be understood by those persons of ordinary skill in the relevant art, is a substituent attached to the hydrocarbyl chain or ring which during reaction is dislodged or displaced to create a valency on a carbon or hetero atom in the hydrocarbyl chain or ring, said valency being filled by a nucleophile. As examples of leaving groups may be mentioned halogen atoms such as chlorine, bromine, and iodine; protonated hydroxyl groups; quaternary ammonium salts ($NT_4^+$); sulfonium salts ($ST_3^+$); and sulfonates (—$SO_3T$); where T is, e.g., methyl or para-tolyl. Of all these classes of reactive functionality, the preferred functionality includes hydroxyl, —$COOR^5$, $CR^6$=$CH_2$, —C—$CR^6$=$CH_2$, Cl, an isocyanate group, a blocked isocyanate group and —$NHR^5$, wherein $R^5$ is selected from hydrogen and a hydrocarbyl (preferably of up to 24 carbon atoms); and $R^6$ is selected from hydrogen and an alkyl of 1 to 4 carbon atoms (preferably hydrogen and methyl).

The term "hydrocarbylene" in the context of the present invention is a divalent hydrocarbon group in which both valencies derive by abstraction of hydrogens from carbon atoms. Included within the definition of hydrocarbylene are the same groups as indicated above for hydrocarbyl and functional hydrocarbyl with, of course, the extra valency (for example, alkylene, alkenylene, arylene, alkylaryl, etc.).

The term "functional hydrocarbylene" in the context of the present invention refers to a species of hydrocarbylene possessing pendant reactive functionality, latent reactive functionality, and/or leaving groups. The term "non-functional hydrocarbylene" in the context of the present invention refers generally to a hydrocarbylene other than a functional hydrocarbylene.

The pyrimidines and triazines in accordance with the present invention also relate to latent stabilizing compounds against actinic radiation of the general formulas (II)–(V), wherein at least one of the hydroxyl groups on the aryl ring ortho to the point of attachment to the triazine or pyrimidine ring is blocked, that is, wherein at least one X is other than hydrogen. Such latent stabilizing compounds liberate the effective stabilizers by cleavage of the O—X bond, e.g., by heating or by exposure to UV radiation. Latent stabilizing compounds are desirable because they have many favorable properties, i.e., good substrate compatibility, good color properties, a high cleavage rate of the O—X bond, and a long shelf life. The use of latent stabilizing compounds is further described in U.S. Pat. Nos. 4,775,707, 5,030,731, 5,563,224 and 5,597,854, which are incorporated herein for all purposes as if fully set forth.

Latent stabilizing compounds comprising pyrimidines and triazines in accordance with the present invention can be prepared from compounds of the general formulas (I)–(V), wherein at least one X is hydrogen, by subjecting said compounds to a further reaction to form latent stabilizing compounds, as described in the immediately preceding incorporated references.

As examples of blocking groups X may be mentioned one or more of the following groups: allyl, —$COR^a$, —$SO_2R^b$, $SiR^cR^dR^e$, $PR^fR^g$ or $POR^fR^g$, $NCOHR^b$, wherein each $R^a$ is independently selected from $C_1$–$C_8$ alkyl, halogen-substituted $C_1$–$C_8$ alkyl, $C_5$–$C_2$ cycloalkyl, $C_2$–$C_8$ alkenyl, —$CH_2$—CO—$CH_3$, $C_1$–$C_{12}$ alkoxy, and phenyl or phenoxy which is unsubstituted or substituted by $C_1$–$C_2$ alkyl, $C_1$–$C_4$ alkoxy, halogen and/or benzyl;

each $R^b$ is independently selected from $C_1$–$C_{12}$ alkyl, $C_6$–$C_{10}$ aryl and $C_7$–$C_{18}$ alkylaryl;

each $R^c$, $R^d$ and $R^e$ is independently selected from $C_1$–$C_{18}$ alkyl, cyclohexyl, phenyl and $C_1$–$C_{18}$ alkoxy, each $R^f$ and $R^g$ is independently selected from $C_1$–$C_{12}$ alkoxy, $C_1$–$C_{12}$ alkyl, $C_5$–$C_{12}$ cycloalkyl, and phenyl or phenoxy which is unsubstituted or substituted by $C_1$–$C_{12}$ alkyl, $C_1$–$C_4$ alkoxy, halogen and/or benzyl; and each $R^h$ is independently selected from $C_1$–$C_8$ alkyl, $C_5$–$C_{12}$ cycloalkyl, $C_2$–$C_8$ alkenyl, —$CH_2$—CO—$CH_3$, and phenyl which is unsubstituted or substituted by $C_1$–$C_{12}$ alkyl, $C_2$–$C_8$ alkenyl, $C_1$–$C_4$ alkoxy, halogen and/or benzyl.

The reaction to give the latent stabilizing compounds of the present invention of the general formula (I) through (V), in which X is allyl, —$COR^a$, —$SO_2R^b$, —$SiR^cR^dR^e$, —$PR^fR^g$, or —$POR^fR^g$, can be carried out, for example, by reaction of the compounds of the general formula (I) through (IV), wherein at least one X is hydrogen with the corresponding halides such as allyl chloride, Cl—$COR^a$, Cl—$SO_2R^b$, Cl—$SiR^cR^dR^e$, Cl—$PR^fR^g$, or Cl—$POR^fR^g$. The reaction to give the latent stabilizing compounds of the present invention of the general formulas (II) through (IV) in which X is $CONHR^b$ can be carried out, for example, by reaction of the compounds of the general formulas (II) through (V), wherein at least one X is hydrogen with the corresponding isocyanates. Furthermore, acylated compounds can be obtained by reaction of the compounds of the general formulas (II) through (V), wherein at least one X is hydrogen with anhydrides, ketenes, or esters, such as lower alkyl esters, as is well known to one skilled in the art. The above-described reagents may be used in approximately equimolar amounts or in excess, for example, from 2 to 20 mol with respect to the hydroxyl groups desired to be made latent in the starting compound of the general formula (II) through (V).

Catalysts customarily used for acylation, sulfonylation, phosphonylation, silylation, or urethanation reactions may be used in forming the latent stabilizing substituted pyrimidines and triazines of the present invention. For example, acylation and sulfonylation reaction catalysts such as tertiary or quaternary amines including, but not limited to, triethylamine, dimethylaminopyridine, or tetrabutylammonium salts, may be used for forming these latent stabilizing compounds.

The reaction may be carried out in the presence of a solvent, such as relatively inert organics, e.g., hydrocarbons such as toluene and xylene, chlorinated hydrocarbons such as carbon tetrachloride or chloroform, or ethers such as tetrahydrofuran or dibutyl ether, with or without a solvent. Alternatively, the reagent(s) may be employed as the solvent. The reaction temperature is usually between room temperature and about 150° C., for example, up to the boiling point of the solvent when a solvent is used.

Further preferred embodiments may include any combination of the parameters mentioned above.

Methods of Preparation

The triazines and pyrimidines having di-ortho hydrocarbyl substituted aromatic rings of the invention can be prepared by a Friedel-Crafts reaction of an aromatic moiety (XXX) with a halogen substituted triazine or pyrimidine compound (XXXI) wherein each Z is independently nitrogen or methine, and at least two Z are nitrogen, as illustrated in Scheme I.

Scheme I

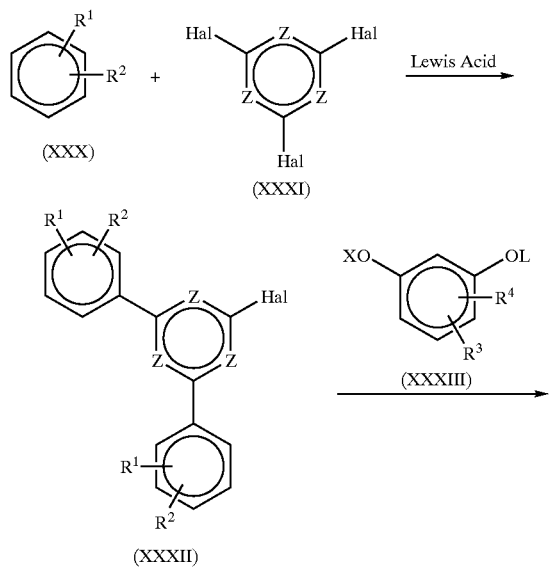

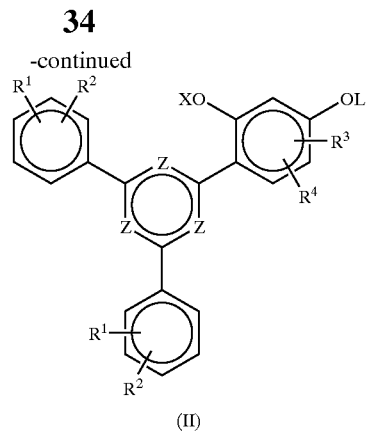

(II)

wherein the term "Lewis acid," as used herein, means any electron pair acceptor as is well known to those or ordinary skill in the art. Lewis acids include, but are not limited to, aluminum halides, alkylaluminum halides, boron halides, tin halides, titanium halides, lead halides, zinc halides, iron halides, gallium halides, arsenic halide, copper halides, cadmium halides, mercury halides, antimony halides, and the like. Preferred Lewis acids include aluminum trichloride, aluminum tribromide, trimethylaluminum, boron trifluoride, boron trichloride, zinc dichloride, titanium tetrachloride, tin dichloride, tin tetrachloride, or a mixture thereof, and Hal is bromine, chlorine, or iodine; and $R^1$ and $R^2$ are defined above and are attached to the aromatic moiety ortho to each other. Preferably, the Lewis acids used with a promotor such as disclosed in WO 00/29392, the contents of which are expressly incorporated herein by reference thereto.

In compound (XXXI) L, X, $R^3$, and $R^4$ are as defined above. Substitution of either L or X, or both for an alkyl group or hydroxy blocking group can be conducted before or after the second step. One of ordinary skill in the art with little or no experimentation can easily determine the conditions to substitute either L or X, or both.

The relative amounts of the reactants are as follows. The amount of compounds of Formula (XXXI) should be an amount sufficient to react with the aromatic compound of Formula (XXX) to produce compound of Formula (XXXII). The amount of aromatic compound of Formula (XXX) is important to ensure that a sufficient amount of aromatic compounds of Formula (XXXII) is synthesized without excessive amounts of undesired side products such as trisaryl triazine or trisaryl pyrimidine. Moreover, excess amounts of aromatic compounds can lead to undesired product distributions enriched in mono- and tris-aryl triazines, or mono- and tris-aryl pyrimidines thus, making product separation and purification difficult and resource consuming.

The amount of aromatic compounds (XXX) should be an amount sufficient to synthesize the 2-halo-4,6-bisaryl-1,3,5-triazine or 2-halo-4,6-bisarylpyrimidine. Preferably, there should be between about 1 to about 5 mol equivalents of aromatic compound of Formula (XXX) to compound of Formula (XXXI). Preferably, there should be between about 0.5 to about 2.5 mol equivalents of compound of Formula (XXXIII) to compounds of Formula (XXXII).

The amount of Lewis acid, used in the reaction should be an amount sufficient to transform the 2,4,6-trihalo-1,3,5-triazine or 2,4,6-trihalo-pyrimidine to the preferred 2-halo-4,6-bisaryl-1,3,5-triazine or 2-halo-4,6-bisarylpyrimidine, respectively. The amount of Lewis acid should be between about 0.5 to about 500 mol equivalents. Preferably, the amount of Lewis acid should be between about 0.75 to about 10 mol equivalents, and most preferably between about 1 to about 5 mol equivalents.

The reaction should run for a sufficient amount of time, at a sufficient temperature and pressure to synthesize the desired triazine or pyrimidine compound. The preferred reaction time for the synthesis of compounds of Formula (XXXII), i.e., the first step, is between about 5 minutes and about 48 hours, more preferred between about 15 minutes and about 24 hours. The preferred reaction time for the synthesis of compounds of Formula (It), i.e., the second step, is between about 10 minutes and about 24 hours, more preferably time is between about 30 minutes and about 12 hours. The reaction pressure is not critical and can be about 1 atm or higher if desired. Preferably, the reaction is carried out under an inert gas such as nitrogen or argon. One of ordinary skill in the art with little or no experimentation can readily determine the optimum temperature to obtain the desired product. Representative reaction conditions for preparing the compounds of formula (II) are provided in the examples.

The reaction may be a step-wise process or a one-step process. As used herein, the term "step-wise" means a reaction sequence wherein a series of reactions are conducted, the first reaction producing compounds of Formula (XXXII) and being carried out to between about 50% to about 100% completion prior to addition of a compound of Formula (XXXIII) to produce compounds of Formula (II). Preferably the reaction is carried out to between about 70% to about 100% completion prior to addition of compound of Formula (XXXIII), and more preferably to between about 75% to about 100% completion.

The step-wise process comprises mixing at least one Lewis acid, and compounds of Formula (XXXI) with one or more of the desired aromatic compounds of Formula (XXX), preferably until the reaction is between about 70% to about 100% completed. Thereafter, the product of Formula (XXXII) is isolated and purified. The aromatic compound of Formula (XXXIII) is then added to the purified product of Formula (XXXII) along with a Lewis acid to synthesize the compounds of Formula (II). The step-wise sequence allows for the isolation, purification, and storage of compounds of Formula (XXXII) prior to subsequent reaction with aromatic compounds of Formula (XXXIII).

Compounds of the formula (XXII) are novel intermediates that can be used to prepare the triazine or pyrimidine compounds of the invention. Thus, the present invention is also directed to the 2-halt-4,6-bisaryl-1,3,5-triazine and 2-halo-4,6-bisarylpyrimidine of structure (XXXII) wherein the aryl groups have two hydrocarbyl groups that are ortho to each other. To synthesize compounds of Formula (II) the preferred addition time of the aromatic compound of Formula (XXXIII) to the reaction mixture is between about 5 minutes to about 10 hours, more preferred addition time is between about 10 minutes to about 5 hours, and most preferred addition time is between about 15 minutes to about 2 hours.

The Lewis acid should be present in amounts sufficient to react with the number of halogens being substituted on compounds of Formula (XXXI). A range of between about 1 to about 5 mol equivalents of Lewis acid can be used. The preferred Lewis acid is aluminum chloride. A preferred amount of Lewis acid is between about 2 to about 4 mol equivalents to halo-triazine or halo-pyrimidine.

The synthesis of compounds of Formula (III), (IV), or (V) can be performed by methods commonly known in the art. One of ordinary skill in the art with little or no experimentation can determine the appropriate conditions to obtain the polymer product desired.

Other useful methods of synthesis of substituted triazines are disclosed in the following sources: U.S. Pat. Nos. 5,106,972, 5,438,138, 5,478,935, WO 96/28431, EP 649841, EP 648756, EP 577559, Brunetti, H; Luethi, C.; *Helv. Chemica Acta,* 55 (1972) pp. 1566–1595; Tanimoto, S.; Yamagata, M. *Senryo to Yakahin,* 40 (1995) pp 339ff, EP 779,280A1; and Japanese Patent Kokai Tokkyo Koho 9,059, 263. Preferably the triazines are synthesized by the method disclosed in WO 00/29392 the contents of which are incorporated herein by reference thereto.

Uses of the Pyrimidines and Triazines Having Aromatic Groups Substituted With at Two Hydrocarbyl Groups that are Ortho to Each Other As indicated earlier, the novel ortho di-hydrocarbyl phenyl substituted pyrimidines and triazines of the present invention are particularly useful as ultraviolet light absorber agents for stabilizing a wide variety of materials including, for example, various polymers (both crosslinked and thermoplastic), photographic materials, and dye solutions for textile materials, as well as in ultraviolet light screening agents (such as sunscreens). The novel triazines and pyrimidines of the present invention, having hydrocarbyl groups in the benzocyclic ring that are ortho to each other, can be incorporated into such material in anyone of a variety of conventional manners, including for example, physical mixing or blending, optionally, with chemical bonding to the material (typically to a polymer), as a component in a light stabilizing composition such as a coating or solution, or as a component in a UV screening composition such as a sunscreen composition.

In one embodiment of the present invention, the pyrimidines and triazines of the present invention can be employed to stabilize materials which are subject to degradation by ultraviolet radiation by incorporating the presently claimed compounds into polymeric materials, either chemically or physically. Non-limiting examples of polymeric materials that may be so stabilized are polyolefins; polyesters; polyethers; polyketones; polyamides; natural and synthetic rubbers; polyurethanes; polystyrenes; high-impact polystyrenes; polyacrylates; polymethacrylates; polyacetals; polyacrylonitriles; polybutadienes; polystyrenes; ABS; SAN (styrene acrylonitrile); ASA (acrylate styrene acrylonitrile); cellulosic acetate butyrate, cellulosic polymers; polyimides; polyamideimides; polyetherimides; polyphenylsulfides; PPO; polysulfones; polyethersulfones; polyvinylchlorides; polycarbonates; polyketones; aliphatic polyketones; thermoplastic TPO's; aminoresin crosslinked polyacrylates and polyesters; polyisocyanate crosslinked polyesters and polyacrylates; phenol/formaldehyde, urea/formaldehyde, and melamine/formaldehyde resins; drying and non-drying alkyd resins; alkyd resins; polyester resins; acrylate resins cross-linked with melamine resins, urea resins, isocyanates, isocyanurates, carbamates, and epoxy resins; cross-linked epoxy resins derived from aliphatic, cycloaliphatic, heterocyclic and aromatic glycidyl compounds which are cross-linked with anhydrides or amines; polysiloxanes; Michael addition polymers of amines or blocked amines with activated unsaturated and methylene compounds, ketimines with activated unsaturated and methylene compounds, polyketimines in combination with unsaturated acrylic polyacetoacetate resins, and polyketimines in combination with unsaturated acrylic resins; radiation curable compositions; epoxymelamine resins; organic dyes; cosmetic products; cellulose-based paper formulations; photographic film paper; ink; and blends thereof.

The degradable polymer may be any polymer requiring stabilization, and includes homopolymers and copolymers of various monomers. It may be an addition polymer, a condensation polymer, a graft polymer, a thermosetting polymer, a photopolymer, a polymer blend, or a thermoplastic polymer. It may be in the form of a fiber, a polymer film such as polypropylene films, a thin film such a solvent based coating, a water-based coating, a stoving lacquer, a powder coating, a gel coat, and the like, or it may be in the form of a molded article. Examples of degradable polymers which can be stabilized include, but are not limited to:

1. Homo- and copolymers of monoolefins and diolefins including but not limited to ethylene, propylene, isobutylene, butene, methylpentene, hexene, heptene, octene, isoprene, butadiene, hexadiene, dicyclopentadiene, ethylidene and cycloolefins such as cyclopentene and norbornene; for example, polyethylenes (which optionally can be crosslinked) such as high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE) and branched low density polyethylene (BLDPE).
2. Copolymers of one or more monoolefins and/or diolefins with carbon monoxide and/or with other vinyl monomers, including limited acrylic and methacrylic acid, acrylates and methacrylates, acrylamides, acrylonitriles, styrenes, vinyl acetate (such as ethylene/vinyl acetate copolymers), vinyl halides, vinylidene halides, maleic anhydride and allyl monomers such as allyl alcohol, allyl amine ally glycidyl ether and derivatives thereof.
3. Hydrocarbon resins (such as $C_5$–$C_8$) including hydrogenated modifications thereof and mixtures of polyalkylenes and starch.
4. Homo- and copolymers of styrenes such as styrene, p-methylstyrene and α-methylstyrene.
5. Copolymers of one or more styrenes with other vinyl monomers such as olefins and diolefins (e.g., ethylene, isoprene and/or butadiene), acrylic and methacrylic acid, acrylates and methacrylates, acrylamides, acrylonitriles, vinyl acetate (such as ethylene/vinyl acetate copolymers), vinyl halides, vinylidene halides, maleic anhydride and allyl compounds such as allyl alcohol, allyl amine allyl glycidyl ether and derivatives thereof.
6. Graft copolymers of styrenes on polybutadienes, polybutadiene/styrene copolymers and polybutadiene/acrylonitrile copolymers; styrene (or α-methylstyrene) and acrylonitrile (or methacrylonitrile) on polybutadiene; styrene and maleic anhydride on polybutadiene; styrene, acrylonitrile and maleic anhydride or maleimide on polybutadiene; styrene and acrylonitrile on ethylene/propylene/diene copolymers; styrene and acrylonitrile on polyalkyl acrylates or methacrylates; and styrene and acrylonitrile on acrylate/butadiene copolymers.
7. Halogen-containing polymers such as polychloroprene; chlorinated rubbers; chlorinated and brominated isobutylene/isoprene copolymers; chlorinated or sulfochlorinated polyethylene; copolymers of ethylene and chlorinated ethylene; epichlorohydrin polymers and copolymers; and polymers and copolymers of halogen-containing vinyl compounds such as vinyl chloride, vinylidene chloride, vinyl fluoride and/or vinylidene fluoride and other vinyl monomers.
8. Homo- and copolymers derived from α,β-unsaturated acids and derivatives thereof such as acrylic acid, methacrylic acid, acrylates, methacrylates, acrylamides and acrylonitriles.
9. Copolymers of the monomers mentioned in (8) with other unsaturated monomers such as olefins and diolefins (e.g., butadiene), styrenes, vinyl halides, maleic anhydride and allyl monomer such as allyl alcohol, allyl amine, allyl glycidyl ether and derivatives thereof.
10. Homo- and copolymers derived from unsaturated alcohols and amines or the acyl derivatives or acetals thereof, such as vinyl alcohol, vinyl acetate, vinyl stearate, vinyl benzoate, vinyl maleate, vinyl butyral, allyl alcohol, allyl amine, allyl glycidyl ether, allyl phthalate and allyl melamine; as well as copolymers of such monomers with other ethylenically unsaturated monomers mentioned above.

For the preceding groups 1–10 of polymers, the present invention further encompasses these polymers as prepared by metallocene catalysts.

11. Homo- and copolymers of cyclic ethers such as alkylene glycols and alkylene oxides, as well as copolymers with bisglycidyl ethers.
12. Polyacetals such as polyoxymethylene and those polyoxymethylenes which contain ethylene oxide as a comonomer; and polyoxymethylenes modified with thermoplastic polyurethanes, acrylates and/or MBS.
13. Polyphenylene oxides and sulfides.
14. Polyurethanes derived from hydroxy-functional components such aq polyhydric alcohols, polyethers, polyesters, polyacrylics and/or polybutadienes on the one hand, and aliphatic and/or aromatic isocyanates on the other, as well as precursors thereof.
15. Polyamides and copolyamides derived from diamines, dicarboxylic acids and/or aminocarboxylic acids or the corresponding lactams, such as polyamide 4, polyamide 6, polyamide 6/6, polyamide 6/10, polyamide 6/9, polyamide 6/12, polyamide 4/6, polyamide 12/12, polyamide 11 and polyamide 12; aromatic polyamides starting from m-xylene diamine and adipic acid; polyamides prepared from hexamethylene diamine and isophthalic and/or terephthalic acid and with or without an elastomer as a modifier, for example, poly-2,4,4-trimethylhexamethylene terephthalamide or poly-m-phenylene isophthalamide; block copolymers of the aforementioned polyamides with polyolefins, olefin copolymer, ionomers, chemically bonded or grafted elastomers, or polyethers such as polyethylene glycol, polypropylene glycol or polytetramethylene glycol; and polyamides condensed during processing (RIM polyamide systems).
16. Polyureas, polyimides, polyamide-imides, polyetherimides, polyesterimides, polyhydantoins and polybenzimidazoles.
17. Polyesters derived from dicarboxylic acids, diols and/or hydroxycarboxylic acids or the corresponding lactones, such as polyethylene terephthalate, polybutylene terephthalate, poly-1,4-dimethylcyclohexane terephthalate and polyhydroxybenzoates, as well as block copolyether esters derived from hydroxyl-terminated ethers; PETG; PEN; PTT; and also polyesters modified with polycarbonate or MBS.
18. Polycarbonates and polyester carbonates.
19. Polysulfones, polyether sulfones and polyether ketones.
20. Crosslinked polymers derived from aldehydes condensation resins such as phenol/formaldehyde resins, urea/formaldehyde resins and melamine/formaldehyde resins.
21. Drying and nondrying alkyd resins.
22. Unsaturated polyester resins derived from copolyesters of saturated and unsaturated dicarhoxylic acids with polyhydric alcohols and vinyl compounds as crosslinking agents and also halogen-containing modifications thereof.

23. Crosslinkable acrylic resins derived from substituted acrylates such as epoxy acrylates, hydroxy acrylates, isocyanato acrylates, urethane acrylates or polyester acrylates.
24. Alkyd resins, polyester resins and acrylate resins crosslinked with melamine resins, urea resins, isocyanates, isocyanurates, carbamates or epoxy resins.
25. Crosslinked epoxy resins derived from aliphatic, cycloaliphatic, heterocyclic and/or aromatic glycidyl compounds such as bisphenol A and bisphenol F, which are crosslinked with hardeners such as anhydrides or amines.
26. Natural polymers such as cellulose, rubber, gelatin and chemically modified homologous derivatives thereof, including cellulose acetates, cellulose propionates and cellulose butyrates, or the cellulose ethers such as methyl cellulose, as well as rosins and their derivatives.
27. Polysiloxanes.
28. Michael addition polymers of amines or blocked amines (e.g., ketimines) with activated unsaturated and/or methylene compounds such as acrylates and methacrylates, maleates and acetoacetates.
29. Mixtures or blends of any of the above, such as PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylate, POM/thermoplastic PUR, PC/thermoplastic polyurethane, POM/acrylate, POM/MBS, PPO/HIPS, PPO/PA6.6 and copolymers, PA/HDPE, PP/HDPE, PP/LDPE, LDPE/HDPE, LDPE/EVA, LDPE/EAA, PA/PP, PA/PPO, PBT/PC/ABS, PBT/PET/PC and the like.
30. Polyketimines in combination with unsaturated acrylic polyacetoacetate resins or with unsaturated acrylic resins including urethane acrylates, polyether acrylates, vinyl or acryl copolymers with pendant unsaturated groups and acrylated melamines.
31. Radiation curable compositions containing ethylenically unsaturated monomers oligomers and a polyunsaturated aliphatic oligomer.
32. Epoxymelamine resins such as light-stable epoxy resins cross-linked by an epoxy functional coetherified high solids melamine resin. Other materials which can be stabilized include, for example:
  33. Naturally occurring and synthetic organic materials which may be mixtures of compounds, including mineral oils, animal and vegetable fats, oils and waxes, or oils, fats or waxes based on synthetic esters (e.g., phthalates, adipates, phosphates or trimellitates) and also mixtures of synthetic esters with mineral oils in any ratio.
34. Aqueous emulsions of natural or synthetic rubber such as natural latex or lattices of carboxylated styrene/butadiene copolymers.
35. Organic dyes such as azo dyes (diazo, triazo and polyazo), anthraquinones, benzodifuranones, polycyclic aromatic carbonyl dyes, indigoid dyes, polymethines, styryl dyes, di- and triaryl carbonium dyes, phthatocyanines, quinophthalones, sulfur dyes, nitro and nitroso dyes, stilbene dyes, formazan dyes, quinacridones, carbazoles and perylene tetracarboxylic diimides.
36. Cosmetic products, such as skin lotions, collagen creams, sunscreen, facial make-up, etc., comprising synthetic materials such as antioxidants, preservatives, lipids, solvents, surfactants, colorants, antiperspirants, skin conditioners, moisturizers etc.; as well as natural products such as collagen, proteins, mink oil, olive oil, coconut oil, carnauba wax, beeswax, lanolin, cocoa butter, xanthan gum, aloe, etc.
37. Cellulose-based paper formulations for use, e.g., in newsprint, cardboard, posters, packaging, labels, stationery, book and magazine paper, bond typing paper, multi-purpose and office paper, computer paper, xerographic paper, laser and ink-jet printer paper, offset paper, currency paper, etc.
38. Photographic film paper.
39. Ink.

Among polymeric compounds, preference is given to the polycarbonates, polyesters, polyamides, polyacetals, polyphenylene oxides, and polyphenylene sulfides. In particular the novel triazines and pyrimidines of the invention can be used to stabilize aliphatic polyamides, polyurethanes, and polycarbonates.

The novel triazines and pyrimidines of the invention can also be used with aliphatic polyamide polymers. An "aliphatic polyamide" is a polyamide characterized by the presence of recurring carbonamide groups as an integral part of the polymer chain which are separated from one another by at least two aliphatic carbon atoms. Illustrative of these polyamides are those having recurring monomeric units represented by the general formula:

$$—NHC(O)RC(O)NHR^1— \text{ or } —NH—R—C(O)—$$

or a combination hereof in which R and $R^1$ are the same or different and are alkylene groups of at least about two carbon atoms, preferably alkylene having from about 2 to about 12 carbon atoms. Exemplary of such polyamides are polyamides formed by the reaction of diamines and diacids such as poly(tetramethylene adipamide)(nylon 4,6), poly(hexamethylene adipamide) (nylon 6,6), poly(hexamethylene azelamide) (nylon 6,9), poly(hexamethylene sebacamide) (nylon 6,10), poly(heptamethylene pimelamide) (nylon 8,8), poly(nonamethylene azelamide) (nylon 9,9), poly(decamethylene azelamide) (nylon 10,9), and the like. Also illustrative of useful aliphatic polyamides are those formed by polymerization of amino acids and derivatives thereof, as for example lactams. Illustrative of these useful polyamides are poly(4-aminobutyric acid) (nylon 4), poly(6-aminohexanoic acid) (nylon 6), poly(7-aminoheptanoic acid) (nylon 7), poly(8-aminoocatanoic acid) (nylon 8), poly(9aminononanoic acid) (nylon 9), poly(10-aminodecanoic acid) (nylon 10), poly(11-aminoundecanoic acid) (nylon 11), poly(12-aminododecanoic acid) (nylon 12), and the like. Blends of two or more aliphatic polyamides may also be employed.

Copolymers formed from any combination of the recurring units of the above referenced aliphatic polyamides can be used. By way of illustration and not limitation, such aliphatic polyamide copolymers include caprolactam/hexamethylene adipamide copolymer (nylon 6/6,6), hexamethylene adipamide/caprolactam copolymer (nylon 6, 6/6), hexamethylene adipamide/hexamethylene-azelamide copolymer (nylon 6,6/6,9), and copolymers formed from recurring units of the above referenced aliphatic polyamides with aliphatic/aromatic polyamide recurring units may also be used. Examples of such copolyamides are nylon 6/6T; nylon 6,6/6, T; nylon 6/10T; nylon 6/12T; nylon 6,10/6,T etc.

Preferred aliphatic polyamides for use in the practice of this invention are poly(caprolactam), poly(7-aminoheptanic acid), poly(tetramethylene adipamide), poly(hexamethylene adipamide), and mixtures thereof. The particularly preferred aliphatic polyamides are poly(caprolatam), poly(hexamethylene adipamide), poly(tetramethylene adipamide), and mixtures thereof.

Aliphatic polyamides useful in the practice of this invention may be obtained from commercial sources or prepared in accordance with known preparatory techniques. For example, polycaprolactam may be obtained from Honeywell Inc. of Morristown, N.J. and poly(hexamethylene adipamide) may be obtained from E.I. DuPont De Nemours and Company Inc. of Wilmington, Del.

The number average molecular weight of the aliphatic polyamide may vary widely. Usually, the aliphatic polyamide is of film forming molecular weight that is sufficiently high to form a free standing film and sufficiently low to allow melt processing of the blend into a film. Such number average molecular weights are well known to those of skill in the film art and are usually at least about 5,000 as determined by the formic acid viscosity method. In this method, a solution of 9.2 wt. concentration of aliphatic polyamide in 90% formic acid at 25° C. is used. In the preferred embodiments of the invention, the number average molecular weight of the aliphatic polyamide is from about 5,000 to about 1,000,000 and in the particularly preferred embodiments is from about 10,000 to about 100,000. Amongst the particularly preferred embodiments, most preferred are those in which the molecular weight of the aliphatic polyamide is from about 20,000 to about 40,000.

Polyurethane (PUR) elastomer products ("spandex") can be stabilized against discoloration and loss of elasticity during UV light exposure with combinations of UV absorbers according to the invention and hindered amine light stabilizers. Spandex fibers is a PUR elastomer product, which requires very specific UV absorber and hindered amine light stabilizers properties in order to achieve optimum performance. UV absorbers of the triazine class of this invention can be combined with polymeric hindered amine light stabilizers (HALS) to provide outstanding performance in achieving the desired properties for the Spandex fiber applications.

The triazine UV absorber of the invention, used alone or in combination with HALS provides the following properties in the Spandex fiber application: (1) low color contribution at typical use levels in the range of about 0.5–2.0%; (2) sufficient MW, thermal stability and low volatility for fiber processing and thermal exposure conditions; (3) high compatibility and permanence; (4) prevent discoloration and loss of elasticity during exposure to UV light energy, (5) low extraction by water and dry cleaning solvents; (6) low color development during exposure to atmospheric pollutants, $NO_x$, $SO_x$, hydrocarbons, etc.; (7) low interaction with sea water and pool chemicals; (8) low interaction and color development with typical phenolic antioxidants used for the thermal stabilization of Spandex fibers; and (9) low interaction with copper based antioxidant systems used in Nylon fibers for Nylon/Spandex fabrics.

The triazine UV absorber with or without the polymeric HALS provides outstanding stabilization with minimum negative effect on secondary performance properties, such as low color development during $NO_x$ exposure and low interaction with copper based antioxidant systems using in Nylon fibers.

As noted above, any of the triazine compounds disclosed herein can be used to impart one or more of the properties described above to Spandex fibers when added thereto in a stabilization effective amount.

Preferably, these triazine compounds are added in combination with polymeric HALS. The polymeric HALS is preferably poly[(6-morpholino-s-triazine-2,4-diyl)[2,2,6,6,-tetramethyl-4-piperidyl)imino]-hexamethylene [(2,2,6,6-tetramethyl-4-piperidyl)imino]]. Most preferably, the polymeric HALS is the methylated (M) version of the above HALS, which is sold by Cytec Industries, Inc. of West Paterson, N.J. as CYASORB®UV-3529 light stabilizer. Other polymeric HAS disclosed in U.S. Pat. No. 4,331,586 are also suitable.

Spandex fibers are made from a polyurethane (PUR) prepolymer prepared from a diisocyanate and a glycol. There are four basic processes used to convert the PUR prepolymer into the fiber product. These processes are Solution Dry Spinning, Solution Wet Spinning, Melt Extrusion, and Reaction Spinning. The above UV stabilizer alone or in combination with HALS would be suitable for use in any or all four processes.

Spandex fibers may contain a processing antioxidant system, such as a phenolic antioxidant, or a phenolic/phosphite antioxidant combination. In addition, pigments, such as $TiO_2$ are commonly used in the fiber products.

The triazine UV absorber alone or with M-HALS can be dissolved into DMF or DMAC and added to the PUR prepolymer solution prior to solution fiber spinning processes. Also, the combination can be extrusion compounded into the PUR compound used in the melt spinning process.

Preferred polycarbonates are understood to be those polymers the constitutional repeating unit of which corresponds to the formula:

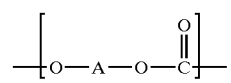

wherein A is a divalent phenolic radical. Examples of A are given inter alia in U.S. Pat. No. 4,960,863 and DE-A-3 922,496. A can be derived, for example, from hydroquinone, resorcinol, dihydroxybiphenylene, or bisphenols in the broadest sense of the term, such as bis(hydroxyphenyl) alkanes, cycloalkanes, sulfides, ethers, ketones, sulfones, sulfoxides, α,α'-bis(hydroxyphenyl)-diisopropylbenzenes, for example the compounds 2,2-bis(4-hydroxyphenyl) propane, 2,2-bis(3,5-dimethyl-4-hydroxyphenyl)-propane, 2,2-bis(3,5-dichloro-4-hydroxyphenyl)propane, 1,1-bis(4-hydroxyphenyl)cyclohexane, or from the compounds of the formula:

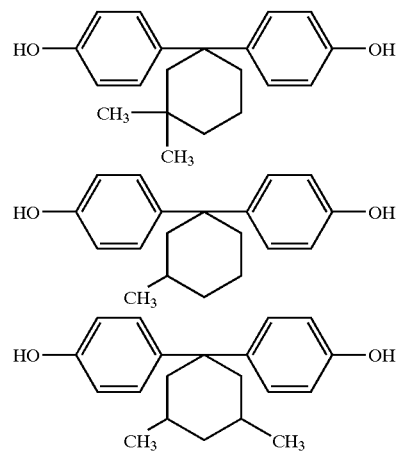

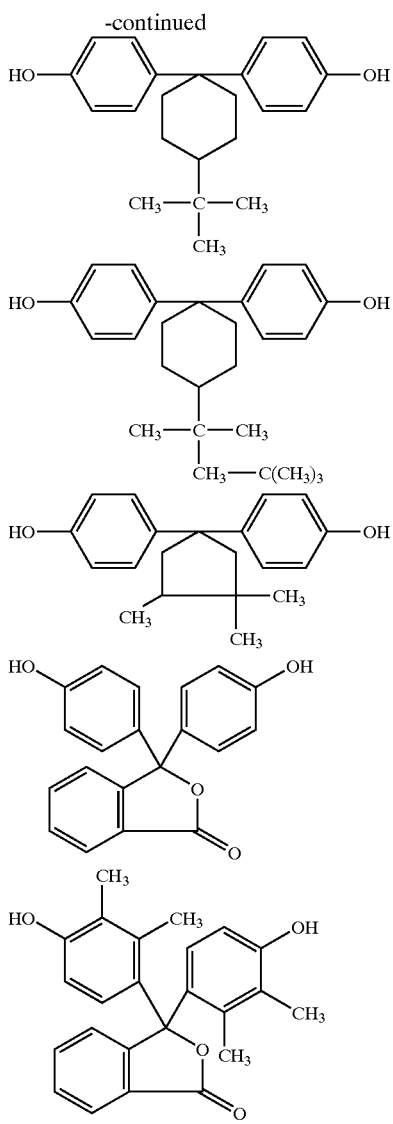

In one embodiment, the preferred resins are polycarbonates based on dihydric phenols such as 2,2-bis-(4-hydroxyphenyl)propane (bisphenol A), 2,4-bis(4-hydroxyphenyl)-2-methylbutane, 1,1-bis-(4-hydroxyphenyl)-cyclohexane, 2,2-bis-(3-chloro-4-hydroxyphenyl)propane, 4,4'-sulfonyldiphenol, and 1,1-bis-(4-hydroxyphenyl)-3,3,5-trimethylcyclohexane.

Also preferred are polycarbonate copolymers incorporating two or more phenols, branched polycarbonates wherein one or more polyfunctional aromatic compounds is reacted with the dihydric phenol(s) and carbonate precursor, and polymer blends of which polycarbonate comprises a significant portion of the blend.

U.S. Pat. No. 5,288,788 describes polycarbonates and polyester carbonates, especially aromatic polycarbonates, for example those based on 2,2-bis(4-hydroxyphenyl) propane or 1,1-bis(4-hydroxyphenyl)cyclohexane.

The novel pyrimidines and triazines of the present invention can also be employed in multilayer systems. In such systems, a polymer composition having from about 0.1 to 20 percent by weight and preferably having a relatively high content of the novel pyrimidines and triazines of the invention, for example, from about 5 to 15 percent by weight, is applied in a thin film (typically between about 5 to 500 μm and preferably from about 10 to 100 μm thick) to a shaped article made from a polymer containing little or no ultraviolet stabilizers. Such composition may be applied at the same time as the shaping of the base structure, for example by coextrusion. Alternatively, application can also be made to the ready-formed base structure, for example by lamination with a film or by coating with a solution. The outer layer or layers of the finished article have the function of a UV filter, which protects the interior of the article from UV light. The outer layer preferably contains about 0.1 to 20 percent, preferably about 1 to 15 percent and more preferably about 2 to 10 percent by weight of the outer layer composition, of at least one of the pyrimidines and triazines of the present invention.

British Patent Application No.2,290,745 describes a number of methods that have been developed to concentrate UV absorbers near or at the surface of polymeric materials. These include surface impregnation (See, e.g., U.S. Pat. Nos. 3,309,220, 3,043,709, 4,481,664 and 4,937,026) and coating a plastic article with solutions containing thermoplastic resins and UV absorbers (See, e.g., U.S. Pat. Nos. 4,668,588 and 4,353,965). Both techniques suffer from drawbacks including requiring additional processing steps (i.e. applying, drying or curing), and encounter difficulties associated with the handling of large processed articles. An additional drawback, particularly relevant to polycarbonate sheet production, is the detrimental effect such post addition treatment would have on the surface of the polymeric substrate.

As described in the U.S. Pat. No. 5,445,872, application of surface layers via coextrusion takes place in a known manner in known coextrusion equipment as taught in U.S. Pat. Nos. 3,487,505 and 3,557,265. Coextrusion is a well recognized method of producing laminated thermoplastic materials by simultaneously extruding various numbers of layers which form a single composite material. U.S. Pat. No. 4,540,623 describes coextruded materials of at least forty layers. Other methods produce as few as two or three different layers.

The novel triazines and pyrimidines of the invention may be incorporated into the thermoplastics of the surfaces layer by standard methods such as dry mixing the additives with granular resin prior to extruding. The layer including the triazines and pyrimidines of the invention may be applied to one or both sides of the thermoplastic article.

Laminated thermoplastic articles which contain additional layers such as a water resistant layer as found in U.S. Pat. No. 4,992,322 are also part of the present invention.

The core layer and the coating layer may be the same or different thermoplastic resin including polyesters, polyester carbonates, polyphenylene oxide, polyvinyl chloride, polypropylene, polypropylene, polyethylene, polyacrylates, polymethacrylates and copolymers and blends such as styrene and acrylonitrile on polybutadiene and styrene with maleic anhydride, and mixtures (polyblends) of such polymers with one another or with other polymers, for example with polyolefins, polyacrylates, polydienes or other elastomers in the form of impact strength modifiers.

The novel triazines and pyrimidines of the invention can also be chemically bonded to substrates, such as polymers, thereby greatly reducing the migration of such UV absorbers, e.g., out of the substrate or away from the substrate surface. The bonding mechanism of the triazines of the present invention involves the formation of a bond (chemical and/or co-valent) between a reactive or latent functionality attached to the triazine or pyrimidine molecule, e.g., by a pendant vinyl or hydroxyl group, and the "host" substrate, such as a polymer.

Incorporation of the triazines and pyrimidines of the invention can be brought about by copolymerization, copolyaddition, copolycondensation, by reaction with a polymer which carries suitable functional groups, or by grafting, in a manner as disclosed in U.S. Pat. Nos. 3,423,360 and 5,189,084 which are incorporated herein by reference as if fully set forth.

Bonding of the triazines and pyrimidines of the invention can occur by polymerization or copolymerization. In the case of the novel triazines of the present invention comprising pendant vinyl groups, polymerization or copolymerization with at least one vinyl monomer, e.g., (meth)acrylic acid, esters of (meth)acrylic acid such as methyl acrylate, amides of (meth)acrylic acid, hydroxyethylacrylate, olefins, vinyl chloride, styrene, butadiene, isoprene and acrylonitrile can be carried out to form homopolymers or copolymers in which the vinyl group is incorporated into the backbone of the polymer. Polymerization or copolymerization can be initiated by initiators, such as free radical, anionic and cationic types, or by actinic radiation, such as LTV, electron beam, x-rays and gamma irradiation from a $Co^{60}$ source, as is well known to those in the polymerization art. Polymerization or copolymerization can be carried out in solution, in an emulsion, in a dispersion, in the melt, or in the solid state as is well known to those in the polymerization art.

Also, bonding of the triazines and pyrimidines of the invention can be brought about by copolyaddition or copolycondensation. Such incorporation can be made by addition during the synthesis of an addition polymer or copolymer or by condensation during the synthesis of a condensation polymer or copolymer by methods known to those skilled in the art. For example, compounds of the formulas (II)–(V) containing the appropriate functional groups can be incorporated into polyesters, polyamides, polyurethanes, epoxy resins, melamine resins, alkyd resins, phenolic resins, polyurethanes, polycarbonates, polysiloxanes, polyacetals and polyanhydrides, to name but a few.

In addition, compounds of the formulas (III)–(V) can be bonded to a monomeric component which is then incorporated into a polymer or copolymer, e.g., by the free radical initiated addition or copolycondensation methods described above. Analogous methods are disclosed in, for example, U.S. Pat. No. 5,459,222 (incorporated by reference herein for all purposes as if fully set forth) for the bonding of benzotriazole and benzophenone stabilizers to diol precursors which are then incorporated by condensation polymerization into polyurethanes and polyesters to impart UV stabilizing properties to said polymers.

Alternately, the triazines and pyrimidines of the invention may also be bonded to polymers by reaction with an oligomer and/or polymer which carries suitable functional groups. For example, at least one triazine or primidine compound comprising a vinyl pendant group can be added, optionally with at least one other vinyl monomer or compound comprising a vinyl group, to unsaturated polyester resins, unsaturated polybutadiene oligomers or unsaturated rubbers and then cured by actinic radiation or by a free radical catalyst. Or, at least one triazine or pyrimidine compound comprising a terminal functional group, such as hydroxyl or amido, may be reacted with a polymer and/or oligomer such as polyesters, polyurethanes and polydiols with reactive end-groups, partially hydrolyzed polyvinylacetate, epoxy resins, polysiloxanes, and polymers comprising maleic anhydride, either in the main chain or as a side-chain, by methods analogous to those well known to those of ordinary skill in the art.

Grafting is yet another way of bonding of the triazines and pyrimidines of the invention to polymers and/or oligomers. Grafting may be carried out in solution, in the melt, or in the solid state with the initiators or actinic radiation types discussed above for polymerization when, for example, the novel triazines and pyrimidines of the invention comprising pendant vinyl groups are used. Such substituted pyrimidines and triazines may be grafted to saturated polymers, e.g., polyolefins and their copolymers such as polyethylene, polypropylene and poly(ethylene-vinyl acetate), or to polymers comprising unsaturated moieties, e.g., polybutadiene, polyisoprene, ethylene-propylene-(diene monomer) terpolymers, and polystyrene and its copolymers.

The triazines and pyrimidines of the invention may be used in widely varying amounts in such applications depending upon such things as the material to be stabilized and the particular application. However, when employed as a stabilizing additive for materials such as organic polymers, the substituted pyrimidines and triazines of the invention are typically employed in amounts from about 0.01 to about 20% by weight, preferably from about 0.1 to about 10% by weight, and most preferably from about 0.1 to about 5% by weight, based on the weight of the material to be stabilized. In screening applications such as sunscreening compositions, the triazines and pyrimidines are utilized in the same relative amounts but based on the total weight of the screening agent.

The novel stabilizers of the present invention may also be employed in a non-bondable capacity, for example, in the stabilization of thermoplastic polymers as set forth in the many of the previously incorporated references. Examples of preferred thermoplastic polymers are polyolefins and polymers comprising heteroatoms in the main chain. Preferred thermoplastic polymers are thermoplastic polymers comprising nitrogen, oxygen and/or sulphur, especially nitrogen or oxygen, in the main chain. Also of interest are compositions in which the polymer is a polyolefin, for example polyethylene or polypropylene.

Incorporation into the thermoplastic polymers can be carried out by addition of the novel triazines and pyrimidines and any further additives by methods conventional in the art. The incorporation can expediently be made before or during shaping, for example by mixing the pulverulent components or by adding the stabilizer to the melt or solution of the polymer, or by applying the dissolved or dispersed compounds to the polymer, with or without subsequent evaporation of the solvent. Elastomers can also be stabilized as lattices.

The novel mixtures can also be added to the polymers to be stabilized in the form of a masterbatch or concentrate which comprises these compounds, for example, in a concentration of from about 1 to about 50%, preferably from about 3 to about 25%, and most preferably from about 5 to about 20% by weight of a polymeric resin.

The novel mixtures can expediently be incorporated into the polymeric material by any number of methods, including those conventionally employed in the art, including by, for example: a) as an emulsion or dispersion (for example to lattices or emulsion polymers); (b) as a dry mix during mixing of additional components or polymer mixtures; (c) by direct addition to the processing equipment (for example extruders, internal mixers, etc.); or (d) as a solution or melt.

The stabilized polymer compositions obtained in this way can be converted into shaped articles, for example fibers, films, tapes, sheets, sandwich boards, containers, pipes, and other profiles, by any number of conventional methods, for example hot pressing, spinning, extrusion, roto-molding, or injection molding. Therefore, the present invention additionally relates to the use of the polymer composition according to the invention for the production of a shaped article.

Depending upon their ultimate end use, the triazines and pyrimidines of the invention may be combined with a variety of additives conventionally employed in the UV stabilizing art. Examples of such additives include but are not limited to:

a. Antioxidants (i) Alkylated monophenols such as 2,6-di-tert-butyl-4-methylphenol; 2-tert-butyl-4,6-dimethylphenol; 2,6-di-tert-butyl-4-ethylphenol; 2,6-di-tert-butyl-4-n-butylphenol; 2,6-di-tert-butyl-4-isobutylphenol; 2,6-dicyclopentyl-4-methylphenol; 2-(α-methylcyclohexyl)-4,6-dimethylphenol; 2,6-dioctadecyl-4-methylphenol; 2,4,6-tricyclohexylphenol; 2,6-di-tert-butyl-4-methoxymethylphenol; nonylphenols which are liner or branched in the side chains such as 2,6-di-nonyl-4-methylphenol; 2,4-dimethyl-6-(1-methylundec-1-yl) phenol; 2,4-dimethyl-6-(1-methylheptadec-1-yl)phenol; 2,4-dimethyl-6-(1-methyltridec$^{-1}$-yl)phenol; and mixtures thereof.

(ii) Alkylthiomethylphenols such as 2,4-dioctylthiomethyl-6-tert-butylphenol; 2,4-dioctylthiomethyl-6-methylphenol; 2,4-dioctylthiomethyl-6-ethylphenol; and 2,6-di-dodecylthiomethyl-4-nonylphenol.

(iii) Hydroquinones and alkylated hydroquinones such as 2,6-di-tert-butyl-4-methoxyphenol; 2,5-di-tert-butylhydroquinone; 2,5-di-tert-amylhydroquinone; 2,6-diphenyl-4-octadecyloxyphenol; 2,6-di-tert-butylhydroquinone; 2,5-di-tert-butyl-4-hydroxyanisole; 3,5-di-tert-butyl-4-hydroxyanisole; 3,5-di-tert-butyl-4-hydroxyphenyl stearate; and bis(3,5-di-tert-butyl-4-hydroxyphenyl)adipate.

(iv) Tocopherols such as α-tocopherol, β-tocopherol, γ-tocopherol, δ-tocopherol, and mixtures thereof (vitamin E).

(v) Hydroxylated thiodiphenyl ethers such as 2,2'-thiobis(6-tert-butyl-4-methylphenol); 2,2'-thiobis(4-octylphenol); 4,4'-thiobis(6-tert-butyl-3-methylphenol); 4,4'-thiobis(6-tert-butyl-2-methylphenol); 4,4'-thiobis(3,6-di-sec-amylphenol); and 4,4'-bis(2,6-dimethyl-4-hydroxyphenyl)disulfide.

(vi) Alkylidenebisphenols such as 2,2'-methylenebis(6-tert-butyl-4-methylphenol); 2,2'-methylenebis(6-tert-butyl-4-ethylphenol); 2,2'-methylenebis[4-methyl-6-α-methylcyclohexyl)phenol]; 2,2'-methylenebis(4-methyl-6-cyclohexylphenol); 2,2'-methylenebis(6-nonyl-4-methylphenol); 2,2'-methylenebis(4,6-di-tert-butylphenol); 2,2'-ethylidenebis(4,6-di-tert-butylphenol); 2,2'-ethylidenebis(6-tert-butyl-4-isobutylphenol); 2,2'-methylenebis[6-(α-methylbenzyl)-4-nonylphenol]; 2,2'-methylenebis[6-(α,α-dimethylbenzyl)$_4$-nonylphenol]; 4,4'-methylenebis(2,6-di-tert-butylphenol); 4,4'-methylenebis(6-tert-butyl-2-methylphenol); 1,1-bis(5-tert-butyl-4-hydroxy-2-methylphenyl)butane; 2,6-bis(3-tert-butyl-5-methyl-2-hydroxylbenzyl)-4-methylphenol; 1,1,3-tris(S-tert-butyl-4-hydroxy-2-methylphenyl)butane; 1,1-bis(5-tert-butyl-4-hydroxy-2-methylphenyl)-3-n-dodecylmercaptobutane; ethylene glycol bis[3,3-bis(3'-tert-butyl-4'-hydroxyphenyl)butyrate], bis(3-tent-butyl-4-hydroxy-5-methylphenyl)dicyclopentadiene; bis[2-(3'-tert-butyl-2'-hydroxy-5'-methylbenzyl)-6-tert-butyl-4-methylphenyl]terephthalate; 1,1-bis(3,5-dimethyl-2-hydroxyphenyl)butane; 2,2-bis(3,5-di-tert-butyl-4-hydroxyphenyl)propane; 2,2-bis(5-tert-butyl-4-hydroxy-2-methylphenyl)-4-n-dodecylmercaptobutane; and 1,1,5,5-tetra(5-tert-butyl-4-hydroxy-2-methylphenyl)pentane.

(vii) O-, - and S-benzyl compounds such as 3,5,3',5'-tetra-tert-butyl-4,4'-dihydroxydibenzyl ether; octadecyl-4-hydroxy-3,5-dimethylbenzylmercaptoacetate; tridecyl-4-hydroxy-3,5-di-tert-butylbenzylmercaptoacetate; tris(3,5-di-tert-butyl-4-hydroxybenzyl)anine; bis(4-tert-butyl-3-hydroxy-2,6-dimethylbenzyl)dithioterephthalate; bis(3,5-di-tert-butyl-4-hydroxybenzyl)sulfide; and isooctyl-3,5-di-tert-butyl-4-hydroxybenzylmercaptoacetate.

(viii) Hydroxybenzylate malonates such as dioctadecyl-2,2-bis(3,5-di-tert-butyl-2-hydroxybenzyl)malonate; dioctadecyl-2-(3-tert-butyl-4-hydroxy-5-methylbenzyl) malonate; didodecylmercaptoethyl-2,2-bis(3,5-di-tert-butyl-4-hydroxybenzyl)malonate; and bis[4-(1,1,3,3-tetramethylbutyl)phenyl]-2,2-bis(3,5-di-tert-butyl-4-hydroxybenzyl)malonate.

(ix) Aromatic hydroxybenzyl compounds such as 1,3,5-tris (3,5-di-tert-butyl-4-hydroxybenzyl)-2,4,6-trimethylbenzene; 1,4-bis(3,5-di-tert-butyl-4-hydroxybenzyl)-2,3,5,6-tetramethylbenzene; and 2,4,6-tris(3,5-di-tert-butyl-4-hydroxybenzyl)phenol.

(x) Triazine compounds such as 2,4-bis(octylmercapto-6-(3,5-di-tert-butyl-4-hydroxyanilino)-1,3,5-triazine; 2-octylmercapto-4,6-bis(3,5-di-tert-butyl-4-hydroxyanilino)-1,3,5-triazine; 2-octylmercapto-4,6-bis (3,5-di-tert-butyl-4-hydroxyphenoxy)-1,3,5-triazine; 2,4,6-tris(3,5-di-tert-butyl-4-hydroxyphenoxy)-1,3,5-triazine; 1,3,5-tris(3,5-di-tert-butyl-4-hydroxybenzyl) isocyanurate; 1,3,5-tris(4-tert-butyl-3-hydroxy-2,6-dimethylbenzyl)isocyanurate; 2,4,6-tris(3,5-di-tert-butyl-4-hydroxyphenylethyl)-1,3,5-triazine; 1,3,5-tris(3,5-di-tert-butyl-4-hydroxyphenylpropionyl)-hexahydro-1,3,5-triazine; and 1,3,5-tris(3,5-dicyclohexyl-4-hydroxybenzyl)isocyanurate.

(xi) Benzylphosphonates such as dimethyl-2,5-di-tert-butyl-4-hydroxybenzylphosphonate; diethyl-3,5-di-tert-butyl-4-hydroxybenzylphosphonate; dioctadecyl-3,5-di-tert-butyl-4-hydroxybenzylphosphonate; dioctadecyl-5-tert-butyl-4-hydroxy-3-methylbenzylphosphonate; and the calcium salt of the monoethyl ester of 3,5-di-tert-butyl-4-hydroxybenzylphosphonic acid.

(xii) Acylaminophenols such as 4-hydroxylauranilide; 4-hydroxystearanilide; and octyl N-(3,5-di-tert-butyl-4-hydroxyphenyl)carbamate.

(xiii) Esters of β-(3,5-di-tert-butyl-4-hydroxyphenyl) propionic acid with mono- or polyhydric alcohols such as methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tristhydroxyethyl)isocyanurate, N,N'-bis(hydroxyethyl) oxamide, 3-thiaundecanol, 3-thiapentadecanol, trimethylhexanediol, trimethylolpropane and 4-hydroxymethyl-1-phospha-2,6,7-trioxabicyclo[2.2.2] octane.

(xiv) Esters of β-(5-tert-butyl-4-hydroxy-3-methylphenyl) propionic acid with mono- or polyhydric alcohols such as methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl)isocyanurate, N,N'-bis(hydroxyethyl) oxamide, 3-thiaundecanol, 3-thiapentadecanol, trimethylhexanediol, trimethylolpropane and 4-hydroxymethyl-1-phospha-2,6,7-trioxabicyclo[2.2.2] octane.

(xv) Esters of β-(3,5-dicyclohexyl-4-hydroxyphenyl) propionic acid with mono- or polyhydric alcohols such as methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)-oxamide, 3-thiaundecanol, 3-thiapentadecanol, trimethylhexanediol, trimethylolpropane and 4-hydroxymethyl-1-phospha-2,6,7-trioxabicyclo[2.2.2] octane.

(xvi) Esters of 3,5-di-tert-butyl-4-hydroxyphenyl acetic acid with mono- or polyhydric alcohols such as methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

(xvii) Amides of β-(3,5-di-tert-butyl-4-hydroxyphenyl) propionic acid such as N,N'-bis(3,5-di-tert-butyl-4-hydroxyphenylpropionyl)hexamethylenediamine; N,N'-bis(3,5-di-tert-butyl-4-hydroxyphenylpropionyl) trimethylenediamine; and N,N'-bis(3,5-di-tert-butyl-4-hydroxyphenylpropionyl)hydrazine.

(xviii) Ascorbic acid (Vitamin C).

(xix) Aminic antioxidants such as N,N'-diisopropyl-p-phenylenediamine; N,N'-di-sec-butyl-p phenylenediamine; N,N'-bis(1,4-dimethylpentyl)-p-phenylenediamine; N,N-bis(1-ethyl-3-methylpentyl)-p-phenylenediamine; N,N'-bis(1-methylheptyl)-p-phenylenediamine; N,N'-dicyclohexyl-p-phenylenediamine; N,N-diphenyl-p-phenylenedi amine; N,N'-bis(2-naphthyl)-p-phenylenediamine; N-isopropyl-N'-phenyl-p-phenylenediamine; N-(1,3-dimethylbutyl)-N'-phenyl-p-phenylenediamine; N-(1-methylheptyl)-N'-phenyl-p-phenylenediamine; N-cyclohexyl-N'-phenyl-p-phenylenediamine; 4-(p-toluenesulfonamoyl) diphenylamine; N,N'-dimethyl-N,N'-di-sec-butyl-p-phenylenediamine; diphenylamine; allyldiphenylamine; 4-isopropoxydiphenylamine; -phenyl-1-naphthylamine; N-(4-tert-octylphenyl)-1-naphthylamine; N-phenyl-2-naphthylamine; octylated diphenylamine such as p,p'-di-tert-octyldiphenylamine; 4-n-butylaminophenol; 4-butyrylaminophenol; 4-nonanoylaminophenol; 4-dodecanoylaminophenol; 4-octadecanoylaminophenol; bis(4-methoxyphenyl)amine; 2,6-di-tert-butyl-4-dimethylaminomethylphenol; 2,4'-diaminophenylmethane; 4,4'-diaminodiphenylmethane; N,N,N',N'-tetramethyl-4,4'-diaminodiphenylmethane; 1,2-bis[(2-methylphenyl)amino]ethane; 1,2-bis (phenylamino)propane; (o-tolyl)biguanide; bis[4-(1',3'-dimethylbutyl)phenyl amine; tert-octylated N-phenyl-1-naphthylamine; a mixture of mono- and dialkylated tert-butyl/tert-octyldiphenylamines, a mixture of mono- and dialkylated nonyldiphenylamines; a mixture of mono- and dialkylated dodecyldiphenylamines; a mixture of mono- and dialkylated isopropyl/isohexyldiphenylamines, a mixture of mono and dialkylated tert-butyldiphenylamines; 2,3-dihydro-3,3-dimethyl-4H-1,4-benzothiazine; phenothiazine; a mixture of mono- and dialkylated tert-butyl/tert-octyl phenothiazines; a mixture of mono- and dialkylated tert-octylphenothiazines; N-allylphenothiazine; N,N,N',N'-tetraphenyl-1,4-diaminobut-2-ene; N,N-bis(2,2,6,6-tetramethylpiperid-4-yl)hexamethylenediamine; bis(2,2,6,6-tetramethylpiperid-4-yl)sebacate; 2,2,6,6-tetramethylpiperidin-4-one; and 2,2,6,6-tetramethylpiperidin-4-ol.

b. UV-absorbers and light stabilizers (i) 2-(2'-Hydroxyphenyl)benzotriazoles such as 2-(2'-hydroxy-5'-methylphenyl)benzotriazole; 2-(3',5'-di-tert-butyl-2'-hydroxyphenyl)benzotriazole; 2-(5'-tert-butyl-2'-hydroxyphenyl)benzotriazole; 2-(2'-hydroxy-5'-(1,1,3,3-tetramethylbutyl)phenyl)benzotriazole: 2-(3',5'-di-tert-butyl-2'-hydroxyphenyl)-5-chlorobenzotriazole; 2-(3'-tert-butyl-2'-hydroxy-5'-methylphenyl)-5-chloro-benzotriazole; 2-(3'-sec-butyl-5'-tert-butyl-2'-hydroxyphenyl)-benzotriazole; 2-(2'-hydroxy-4'-octoxyphenyl)benzotriazole; 2-(3',5'-di-tert-amyl-2'-hydroxphenyl)benzotriazole; 2-(3',5'-bis(α,α-dimethylbenzyl)-2'-hydroxyphenyl)-benzotriazole; a mixture of 2-(3'-tert-butyl 2'-hydroxy-5'-(2-octyloxycarbonylethyl)phenyl)-5-chloro-benzotriazole, 2-(3'-tert-butyl-2'-[2-(2-ethylhexyloxy)carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3' tert-butyl-2'-hydroxy-5-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole and 2-(3'-tert-butyl-2'-hydroxy-5'-(2-isooctyloxycarbonylethyl)phenylbenzotriazole; 2,2-methylenebis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl]benzotriazole with polyethylene glycol 300; and $[R-CH_2CH-COO(CH_2)_3]_2$ B where R=3'-tert-butyl-4'-hydroxy-5'-(2H-benzotriazol-2-ylphenyl.

(ii) 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

(iii) Esters of substituted and unsubstituted benzoic acids such as 4-tert-butyl-phenyl salicylate; phenyl salicylate; octylphenyl salicylate; dibenzoyl resorcinol; bis(4-tert-butylbenzoyl) resorcinol; benzoyl resorcinol; 2,4-di-tert-butylphenyl 3,5-di-tert-butyl-4-hydroxybenzoate; hexadecyl 3,5-di-tert-butyl-4-hydroxybenzoate; octadecyl 3,5-di-tert-butyl-4-hydroxybenzoate; and 2-methyl-4,6-di-tert-butylphenyl 3,5-di-tert-butyl-4-hydroxybenzoate.

(iv) Acrylates such as ethyl α-cyano-β,β-diphenylacrylate; isooctyl α-cyano-β,β-diphenylacrylate; methyl α-carbomethoxycinnamate; methyl α-cyano-p-methyl-p-methoxycinnamate; butyl α-cyano-β-methyl-p-methoxycinnamate; methyl α-carbomethoxy-p-methoxycinnamate; and N-(β-carbomethoxy-β-cyanovinyl)-2-methylindoline.

(v) Nickel compounds such as nickel complexes of 2,2'-thio-bis-[4-(1,1,3,3-tetramethylbutyl)phenol], including the 1:1 or 1:2 complex, with or without additional ligands such as n-butylamine, triethanolamine or N-cyclohexyldiethanolamine; nickel dibutyldithiocarbamate; nickel salts of monoalkyl esters including the methyl or ethyl ester of 4-hydroxy-3,5-di-tert-butylbenzylphosphonic acid; nickel complexes of ketoximes including 2-hydroxy-4-methylphenyl undecylketoxime; and nickel complexes of 1-phenyl-4-lauroyl-5-hydroxypyrazole, with or without additional ligands.

(vi) Sterically hindered amines as well as the N derivatives thereof (e.g., N-alkyl, N-hydroxy, N-alkoxy and N-acyl), such as bis(2,2,6,6-tetramethylpiperidin-4-yl) sebacate; bis(2,2,6,6-tetramethylpiperidin-4-yl)succinate; bis(1,2,2, 6,6-pentamethylpiperidin-4-yl)sebacate; bis(1-octyloxy- 2,2,6,6-tetramethylpiperidin-4-yl)sebacate; bis(1,2,2,6,6-pentamethylpiperidin-4-yl) n-butyl 3,5-di-tert-butyl-4-hydroxybenzylmalonate; the condensate of 1-(2-hydroxyethyl)-2,2,6,6-tetramethyl-4-hydroxypiperidine and succinic acid; the condensate of N,N'-bis(2,2,6,6-tetramethylpiperidin-4-yl)hexamethylenediamine and 4-tert-octylamino-2,6-dichloro-1,3,5-triazine; tris(2,2,6,6-tetramethylpiperidin-4-yl) nitrilotriacetate; tetrakis(2,2,6,6-tetramethylpiperidin-4-yl)-1,2,3,4-butanetetracarboxylate; 1,1'-(1,2-ethanediyl)bis(3,3,5,5-tetramethylpiperazinone); 4-benzoyl-2,2,6,6-tetramethylpiperidine; 4-stearyloxy-2,2,6,6-tetramethylpiperidine; bis(1,2,2,6,6-pentamethylpiperidyl)-2-n-butyl-2-(2-hydroxy-3,5-di-tert-butylbenzyl)malonate; 3-n-octyl-7,7,9,9-tetramethyl-1,3,8-triazaspiro[4.5]decan-2,4-dione; bis(1-octyloxy-2,2,6,6-tetramethylpiperidyl)sebacate; bis(1-octyloxy-2,2,6,6-tetramethylpiperidyl)succinate; the condensate of N,N-bis(2,2,6,6-tetramethylpiperidin-4-yl) hexamethylenediamine and 4-morpholino-2,6-dichloro-1,3,5-triazine; the condensate of 2-chloro-4,6-bis(4-n-butylamino-2,2,6,6-tetramethylpiperidyl)-1,3,5-triazine and 1,2-bis(3-aminopropylamino)ethane; the condensate of 2-chloro-4,6-bis(4-n-butylamino-1,2,2,6,6-pentamethylpiperidyl)-1,3,5-triazine and 1,2-bis-(3-aminopropylamino)ethane; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl) pyrrolidin-2,5-dione; 3-dodecyl-1-(1-ethanoyl-2,2,6,6-tetramethylpiperidin-4-yl)pyrrolidin-2,5-dione; 3-dodecyl-1-(1,2,2,6,6-pentamethylpiperidin-4-yl) pyrrolidine-2,5-dione; a mixture of 4-hexadecyloxy- and 4-stearyloxy-2,2,6,6-tetramethylpiperidine, the condensate of N,N'-bis(2,2,6,6-tetramethylpiperidin-4-yl) hexamethylenediamine and 4-cyclohexylamino-2,6-dichloro-1,3,5-triazine; the condensate of 1,2-bis(3-aminopropylamino)ethane, 2,4,6-trichloro-1,3,5-triazine and 4-butylamino-2,2,6,6-tetramethylpiperidine (CAS Reg. No. [136504-96-6]); 2-undecyl-7,7,9,9-tetramethyl-1-oxa-3,8-diaza-4-oxospiro[4.5]decane; oxo-piperanzinyl-triazines or so-called PIP-T HALS, e.g., GOODRITE® 3034, 3150 and 3159 and similar materials disclosed in U.S. Pat. No. 5,071,981; photobondable HALS such as SANDUVOR® PR-31 and PR-32 (Clariant Corp.) and similar materials disclosed in GB-A-2269819; and the reaction product of 7,7,9,9-tetramethyl-2-cycloundecyl-1-oxa-3,8-diaza-4-oxospiro[4.5]decane and epichlorohydrin. See also generally U.S. Pat. No. 4,619,956, U.S. Pat. No. 5,106,891, GB-A-2269819, EP-A-0309400, EP-A-0309401, EP-A-0309402 and EP-A-0434608.

(vii) Oxamides such as 4,4'-dioctyloxyoxanilide; 2,2'-diethoxyoxanilide; 2,2'-dioctyloxy-5,5'-di-tert-butoxanilide; 2,2'-didodecyloxy-5,5'-di-tert-butyloxanilide; 2-ethoxy-2'-ethyloxanilide; N,N'-bis(3-dimethylaminopropyl)oxamide; 2-ethoxy-5-tert-butyl-2'-ethyloxanilide and its mixture with 2-ethoxy-2'-ethyl-5,4'-di-tert-butoxanilide; and mixtures of o- and p-methoxy disubstituted oxanilides and mixtures of o- and p-ethoxy disubstituted oxanilides.

(viii) 2-(2-Hydroxyphenyl)-1,3,5-triazines disclosed in the previously incorporated references, such as 2,4,6-tris(2-hydroxy-4-octyloxyphenyl)-1,3,5-triazine; 2-(2-hydroxy-4-n-octyloxyphenyl)-4,6-bis(2,4-dimethylphenyl)-1,3,5-triazine; 2-(2-hydroxy-4-(mixed iso-octyloxyphenyl)-4,6-bis(2,4-dimethylphenyl)-1,3,5-triazine; 2-(2,4-dihydroxyphenyl)-4,6-bis(2,4-dimethylphenyl)-1,3,5-triazine; 2,4-bis(2-hydroxy-4-propyloxyphenyl)-6-(2,4-dimethylphenyl)-1,3,5-triazine; 2-(2-hydroxy-4-octyloxyphenyl)-4,6-bis(4-methylphenyl)-1,3,5-triazine; 2-(2-hydroxy-4-dodecyloxyphenyl)-4,6-bis(2,4-dimethylphenyl)-1,3,5-triazine; 2-(2-hydroxy-4-tridecyloxyphenyl)-4,6-bis(2,4-dimethylphenyl)-1,3,5-triazine; 2-[2-hydroxy-4-(2-hydroxy-3-butyloxypropyloxy)phenyl]-4,6-bis(2,4-dimethylphenyl)-1,3,5-triazine; 2-[2-hydroxy-4-(2-hydroxy-3-octyloxypropyloxy)-phenyl]-4,6-bis(2,4-dimethylphenyl)-1,3,5-triazine; 2-[4-dodecyloxy/tridecyloxy-2-hydroxypropoxy)-2-hydroxyphenyl]-4,6-bis(2,4-dimethylphenyl)-1,3,5-triazine; 2-[2-hydroxy-4-(2-hydroxy-3-dodecyloxypropoxy)phenyl]4,6-bis(2,4-dimethylphenyl)-1,3,5-triazine; 2-(2-hydroxy-4-hexyloxy)phenyl-4,6-diphenyl-1,3,5-triazine; 2-(2-hydroxy-4-methoxyphenyl)-4,6-diphenyl-1,3,5-triazine; 2,4,6-tris(2-hydroxy-4-(3-butoxy-2-hydroxypropoxy) phenyl]-1,3,5-triazine; and 2-(2-hydroxyphenyl)-4-(4-methoxyphenyl)-6-phenyl-1,3,5-triazine.

(c) Metal deactivators such as N,N'-diphenyloxamide; N-salicylal-N'-salicyloyl hydrazine; N,N'-bis(salicyloyl) hydrazine; N,N'-bis(3,5-di-tert-butyl-4-hydroxyphenylpropionyl)hydrazine; 3-salicyloylamino-1,2,4-triazole; bis(benzylidene)oxalyl dihydrazide; oxanilide; isophthaloyl dihydrazide; sebacoyl bisphenyl-hydrazide; N,N'-diacetyladipoyl dihydrazide; N,N'-bis (salicyloyl)oxalyl dihydrazide; and N,N'-bis(salicyloyl) thiopropionyl dihydrazide.

(d) Phosphites and phosphonites, such as triphenyl phosphite; diphenyl alkyl phosphites; phenyl dialkyl phosphites; tris(nonylphenyl) phosphite; trilauryl phosphite, trioctadecyl phosphite; distearyl pentaerythritol diphosphite; tris(2,4-di-tert-butylphenyl)phosphite; diisodecyl pentaerythritol diphosphite; bis(2,4,-di-tert-butylphenyl) pentaerythritol diphosphite; bis(2,6-di-tert-butyl-4-methylphenyl)pentaerythritol diphosphite; bis (isodecyloxy)pentaerythritol diphosphite; bis(2,4-di-tert-butyl-6-methylphenyl)pentaerythritol diphosphite; bis(2,4,6-tris(tert-butyl)phenyl)pentaerythritol diphosphite; tristearyl sorbitol triphosphite; tetrakis(2,4-di-tert-butylphenyl)-4,4'-biphenylene diphosphonite; 6-isooctyloxy-2,4,8,10-tetra-tert-butyl-12H-dibenzo[d,g]-1,3,2-dioxaphosphocin; 6-fluoro-2,4,8,10-tetra-tert-butyl-12-methyl-dibenzo[d,g]-1,3,2-dioxaphosphocin; bis(2,4-di-tert-butyl-o-methylphenyl)methylphosphite; and bis(2,4-di-tert-butyl-6-methylphenyl)ethylphosphite.

(e) Hydroxylamines such as N,N-dibenzylhydroxylamine; N,N-diethylhydroxylamine; N,N-dioctylhydroxylamine; N,N-dilaurylhydroxylamine; N,N-ditetradecylhydroxylamine; N,N-dihexadecylhydroxylamine; N,N-dioctadecylhydroxylamine; N-hexadecyl-N-octadecylhydroxylamine; N-heptadecyl-N-octadecylhydroxylamine; and N,N-dialkylhydroxylamine derived from hydrogenated tallow fatty amines.

(f) Nitrones such as N-benzyl-alpha-phenyl nitrone; N-ethyl-alpha-methyl nitrone; N-octyl-alpha-heptyl nitrone; N-lauryl-alpha-undecyl nitrone; N-tetradecyl-alpha-tridecyl nitrone; N-hexadecyl-alpha-pentadecyl nitrone; N-octadecyl-alpha-heptadecyl nitrone; N-hexadecyl-alpha-heptadecyl nitrone; N-octadecyl-alpha-pentadecyl nitrone; N-heptadecyl-alpha-heptadecyl nitrone; N-octadecyl-alpha-hexadecyl nitrone; and nitrones derived from N,N-dialkylhydroxylamines prepared from hydrogenated tallow fatty amines.

(g) Thiosynergists such as dilauryl thiodipropionate and distearyl thiodipropionate.

(h) Peroxide scavengers such as esters of β-thiodipropionic acid, for example the lauryl, stearyl, myristyl or tridecyl esters; mercaptobenzimidazole or the zinc salt of 2-mercaptobenzimidazole; zinc dibutyldithiocarbamate; dioctadecyl disulfide; and pentaerythritol tetrakis(β-dodecylmercapto)propionate.

(i) Polyamide stabilizers such as copper salts in combination with iodides and/or phosphorus compounds and salts of divalent manganese.

(j) Basic co-stabilizers such as melamine; polyvinylpyrrolidone; dicyandiamide; triallyl cyanurate; urea derivatives; hydrazine derivatives; amines; polyamides; polyurethanes; alkali metal salts and alkaline earth metal salts of higher fatty acids, for example calcium stearate, zinc stearate, magnesium behenate, magnesium stearate, sodium ricinoleate and potassium palmitate; antimony pyrocatecholate; and tin pyrocatecholate.

(k) Nucleating agents including inorganic substances such as talc and metal oxides (e.g. titanium oxide or magnesium oxide) and phosphates, carbonates and sulfates of, preferably, alkaline earth metals; organic compounds such as mono- or polycarboxylic acids and salts thereof, for example 4-tert-butylbenzoic acid, adipic acid, diphenylacetic acid, sodium succinate and sodium benzoate; and polymeric compounds such as ionic copolymers (e.g. ionomers).

(l) Fillers and reinforcing agents such as calcium carbonate; silicates; glass fibers; asbestos; talc; kaolin; mica; barium sulfate; metal oxides and hydroxides; carbon black; graphite; wood flour and flours or fibers from other natural products; and synthetic fibers.

(m) Other additives such as plasticizers, lubricants, emulsifiers, pigments, rheological additives, catalysts, levelling assistants, optical brighteners, flameproofing agents, antistatic agents and blowing agents.

(n) Benzofuranones and indolinones such as those disclosed in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4316611, DE-A-4316622, DE-A-4316876, EP-A-0589839 and EP-A-0591102; 3-[4-(2-acetoxy-thoxy)phenyl]-5,7-di-tert-butyl-benzofuran-2-one; 5,7-di-tert-butyl-3-[4-(2-stearoyloxyethoxy)-phenyl] benzofuran-2-one; 3,3'-bis[5,7-di-tert-butyl-3-(4-[2-hydroxyethoxy]phenyl)benzofuran-2-one]; 5,7-di-tert-butyl-3-(4-ethoxyphenyl)benzofuran-2-one; 3-(4-acetoxy-3,5-dimethylphenyl)-5,7-di-tert-butyl-benzofuran-2-one; 3-(3,5-dimethyl-4-pivaloyloxyphenyl)-5,7-di-tert-butyl-benzofuran-2-one; and 5,7-di-tert-butyl-3-(3,4-dimethylphenyl)-3H-benzofuran-2-one.

The novel triazines and pyrimidines of the invention can also be employed in multilayer systems. In such systems, a polymer composition having a relatively high content of novel stabilizer, for example, from about 0.1 to about 20% by weight and preferably about 5–15% by weight, is applied in a thin film (e.g., about 5–500 μm thick and, preferably, about 10–100 μm thick) to a shaped article made from a polymer containing little or no ultraviolet stabilizers. Such composition may be applied at the same time as the shaping of the base structure, for example by coextrusion in a manner analogous to that described in U.S. Pat. No. 4,948,666 (incorporated by reference herein for all purposes as if fully set forth). Alternatively, application can also be made to the ready-formed base structure, for example by lamination with a film or by coating with a solution. The outer layer or layers of the finished article have the function of a UV filter, which protects the interior of the article from UV light.

The outer layer typically contains about 0.1 to about 20%, preferably about 1 to about 15%, and more preferably about 2 to about 10% by weight of the outer layer composition, of at least one of the substituted pyrimidine or triazine compound of the present invention.

The polymers stabilized in this way are notable for high weathering resistance, especially for high resistance to UV light. This enables them to retain their mechanical properties, and their color surface properties such as gloss and distinctness of image, for a long time even when used outside. Moreover, due to the bondable nature of the presently claimed triazine and pyrimidine compounds, migration of these UV absorbers between the layers of the multi-layer coatings can, under the appropriate circumstances, be minimized.

In another embodiment of the present invention, the novel mixtures comprising compounds of the formulas (II)–(V) can be used as stabilizers for coatings, for example for paints such as disclosed in numerous references (see, e.g., U.S. Pat. No. 4,619,956, U.S. Pat. No. 4,740,542, U.S. Pat. No. 4,826,978, U.S. Pat. No. 4,962,142, U.S. Pat. No. 5,106,891, U.S. Pat. No. 5,198,498, U.S. Pat. No. 5,298,067, U.S. Pat. No. 5,322,868, U.S. Pat. No. 5,354,794, U.S. Pat. No. 5,369,140, U.S. Pat. No. 5,420,204, U.S. Pat. No. 5,461,151, U.S. Pat. No. 5,476,937, EP-0434608 and EP-A-0444323). Of particular interest are coatings and paints for the automobile industry. The invention therefore also relates to those compositions which are film-forming binders for coatings. "Coating" means a free flowing composition that can be applied to the surface of an article in a thin film that then hardens to form a substantially solid surface on the article. Typically, the coating provides an interface between the article and the environment.

Such novel coating compositions comprise about 0.01 to about 20%, preferably about 0.1 to about 10%, and more preferably about 0.2 to about 10% by weight of the binder of the coating composition of one or more of the novel triazines and pyrimidines of the invention.

Multilayer systems are possible here as well (such as electrocoat/basecoat/clearcoat systems), where the concentration of the novel stabilizer in one or more of the layers, and typically the outer layer such as the clearcoat, can be relatively high, for example from about 0.01 to about 20%, preferably about 0.1 to about 10%, and more preferably about 0.2 to about 5% by weight of hinder.

The use of the novel stabilizer in coatings is accompanied by the additional advantage that it prevents delamination, i.e. the flaking-off of the coating from the substrate. This advantage is particularly important in the case of metallic substrates, including multilayer systems on metallic substrates, and particularly epoxy e-coated metallic substrates.

The coatings typically include a binder that suspends pigments and other additives in the coating and allows attachment of the coating to the substrate.

The binder can in principle be any binder which is customary in industry, for example those described in Ullmann's Encyclopedia of Industrial Chemistry, 5th Edition, Vol. A18, pp. 368–426, VCH, Weinheim 1991 which is incorporated herein by reference. In general, it is a film-forming binder based on a thermoplastic or curable resin, predominantly on a curable resin. Examples of thermoplastic binders include acrylics, polyesters, polyurethanes, and PVC plastisols. Examples of curable binders include functional alkyd, acrylic, polyester, phenolic, melamine, epoxy and polyurethane resins and mixtures thereof.

Such curable binders can be an ambient curable or a thermosetting binder. Further, in some systems it may be advantageous to add a curing catalyst to such systems. Suitable catalysts which accelerate curing of the binder are described, for example, in Ullmann's Encyclopedia of Industrial Chemistry, Vol. A18, p. 469, VCH Verlagsgesellschaft, Weinheim 1991. Preferred binders include those which comprise a functional acrylate resin and a crosslinking agent.

A wide variety of binders may be employed in such coating systems. In particular, binder may comprise an alkyd, acrylic, polyester, phenolic, melamine, epoxy, polyurethane in, or blends thereof. Examples of such binders include, but are not limited to:

(a) cold- or hot-crosslinkable alkyd, acrylate, polyester, epoxy or melamine resins or mixtures of such resins;

(b) a two-component polyurethane system comprising hydroxyl-containing acrylate, polyester or polyether resins and aliphatic or aromatic isocyanates, isocyanurates or polyisocyanates;

(c) a one-component polyurethane system comprising blocked isocyanates, isocyanurates or polyisocyanates which are deblocked during baking;

(d) a two-component system comprising (poly)ketimines and aliphatic or aromatic isocyanates, isocyanurates or polyisocyanates;

(e) a two-component system comprising (poly)ketimines and an unsaturated acrylate resin or a polyacetoacetate resin or a methacrylamidoglycolate methyl ester, (f) a two-component system comprising carboxyl- or amino-containing polyacrylates and polyepoxides;

(g) a two-component system comprising acrylate resins containing anhydride groups and on a polyhydroxy or polyamino component;

(h) a two-component system comprising (poly)oxazolines and acrylate resins containing anhydride groups, or unsaturated acrylate resins, or aliphatic or aromatic isocyanates, isocyanurates or polyisocyanates;

(i) a two-component system comprising unsaturated polyacrylates and polymalonates;

(j) a thermoplastic polyacrylate system comprising thermoplastic acrylate resins or externally crosslinking acrylate resins in combination with etherified melamine resins; and (k) a system comprising siloxane-modified or fluorine-modified acrylate resins.

Such binder-containing compositions may further comprise a curing catalyst, or an organic solvent, and may be radiation-curable. In particular, such compositions may serve as coating compositions.

Examples of suitable coating compositions containing specific binders include but are not limited to:

1. paints based on ambient curable or thermosetting alkyd, acrylate, polyester, epoxy or melamine resins or mixtures of such resins, if desired with addition of a curing catalyst;

2. two-component polyurethane paints based on hydroxyl-containing acrylate, polyester or polyether resins and aliphatic or aromatic isocyanates, isocyanurates or polyisocyanates;

3. one-component polyurethane paints based on blocked isocyanates, isocyanurates or polyisocyanates which are deblocked during baking;

4. two-component paints based on (poly)ketimines and aliphatic or aromatic isocyanates, isocyanurates or polyisocyanates;

5. two-component paints based on (poly)ketimines and an unsaturated acrylate resin or a polyacetoacetate resin or a methacrylamidoglycolate methyl ester;

6. two-component paints based on carboxyl- or amino-containing polyacrylates and polyepoxides;

7. two-component paints based on acrylate resins containing anhydride groups and on a polyhydroxy or polyamino component;

8. two-component paints based on (poly)oxazolines and acrylate resins containing anhydride groups, or unsaturated acrylate resins, or aliphatic or aromatic isocyanates, isocyanurates or polyisocyanates;

9. two-component paints based on unsaturated polyacrylates and polymalonates;

10. thermoplastic polyacrylate paints based on thermoplastic acrylate resins or externally crosslinking acrylate resins in combination with etherified melamine resins;

11. paint systems based on siloxane-modified or fluorine-modified acrylate resins.

In addition to the binder and one or more triazine or pyrimidine of the invention, the coating composition according to the invention preferably further comprise one or more additional ultraviolet light absorbers including, but not limited to, those specifically listed above in section b. The additional WV absorbers may be, for example, another tris-aryl-1,3,5-triazine, a 2-hydroxyphenyl-2H-benzotriazole, a 2-hydroxybenzophenone, an ester of an unsubstituted benzoic acid, an acrylate, an oxamide (oxanilide), or any combination of the above. Preferably, the additional UV absorber is a 2-hydroxyphenyl-2H-benzotriazole and the weight ratio of benzotriazole to triazine or pyrimidine is from about 4:1 to 1:4. More preferably, the weight ratio of benzotriazole to triazine or pyrimidine is from about 2:1 to 1:2.

To achieve maximum light stability, it is of particular interest to add sterically hindered amines, examples of which are set out in the above-mentioned section b(vi). The invention therefore also relates to a coating composition which, in addition to the binder, the one or more triazine or pyrimidine of the invention, and, optionally, additional UV absorbers, comprises a light stabilizer of the sterically hindered amine type. The sterically hindered amine is employed in an amount of about 0.01 to 5% by weight based on the weight of the solid binder, preferably about 0.02 to 2% by weight.

One specific example of such a sterically hindered amine is a 2,2,6,6-tetramethyl piperazinone containing at least one group of the formula:

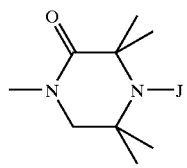

in which 3 is, for example, hydrogen, hydroxyl, alkyl (such as methyl), alkoxy (such as methoxy) or acyl.

More preferably the stabilizer is a 2,2,6,6-tetraalkylpiperidine derivative containing at least one group of the formula:

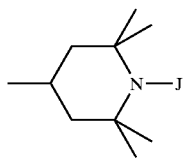

in which J is, for example, hydrogen, hydroxyl, alkyl (such as methyl), alkoxy (such as methoxy) or acyl.

Examples of tetraalkylpiperidine derivatives which can be used in combination with the present trisaryl-1,3,5-triazine compounds are given in U.S. Pat. Nos. 4,314,933, 4,344,876, 4,426,471, 4,426,472, 4,619,956, 5,004,770, 5,006,577, 5,064,883, 5,112,890, 5,124,378, 5,106,891, 5,204,473, and 5,461,151, which are incorporated by reference herein for all purposes as if fully set forth. It is particularly expedient to employ the following tetraalkylpiperidine derivatives, as well as their N-alkyl, N-acyl, N-hydroxyl and N-alkoxy analogs (where not already included in the following list): bis(2,2,6,6-tetramethylpiperid-4-yl) succinate, bis(2,2,6,6-tetramethylpiperid-4-yl) sebacate, bis(1,2,2,6,6-pentamethylpiperid-4-yl) sebacate, di(1,2,2,6,6&pentamethylpiperid-4-yl)butyl-(3,5-di-tert-butyl-4-hydroxybenzyl)malonate, bis(1-otyloxy-2,2,6,6-tetaaethylpiperid-4-yl) sebacate, tetra(2,2,6,6-tetramethylpiperid-4-yl)butane-(1,2,3,4-tetracarboxylate, tetra(1,2,2,6,6-pentamethylpiperid-4-yl)butane-1,2,3,4-tetracarboxylate, 2,2,4,4-tetramethyl-7-oxa-3,20-diaza-21-oxo-dispiro[5.1.11.2]heneicosane, and 8-acetyl-3-dodecyl-1,3,8-triaza-7,7,9,9-tetramethylspiro[4.5]decane-2,4-dione. Commercially available examples of these and other tetaalkylpipieridine derivatives include SANDUVOR® 3050, 3052, 3055, 3056, 3058, PR-31 and PR-32 (Clariant Corp.); TINUVIN® 079L, 123, 144, 292, 440L and 622LD (Ciba Specialty Chemicals); CHIMASORB® 119 and 944 (Ciba Specialty Chemicals); and CYASOR® UV-3346, UV 3529, UV-3853, UV-500 and UV-516 (Cytec Industries Inc.).

In addition, as is well known to those of ordinary skill in the art, to be suitable for coating compositions, the coating composition can also comprise further components including, but not limited to, solvents, pigments, dyes, plasticizers, stabilizers, thixotropic agents, drying catalysts and/or leveling agents, or combinations thereof. Examples of possible components are those described in Ullmann's Encyclopedia of Industrial Chemistry, 5th Edition, Vol. A18, pp. 429–471, VCH, Weinheim 1991, which is incorporated herein by reference.

Exemplary drying catalysts or curing catalysts are, for example, organometallic compounds, amines, amino-containing resins and/or phosphines. Examples of organometallic compounds are metal carboxylates, especially those of the metals Pb, Mn, Co, Zn, Zr or Cu, or metal chelates, especially those of the metal Al, Ti or Zr, or organometallic compounds such as organotin compounds, for example, and mixtures thereof.

Examples of metal carboxylates are the stearates of Pb, Mn or Zn, the octoates of Co, Zn or Cu, the naphthenates of Mn and Co or the corresponding linoleates, resinates or tallates, and mixtures thereof.

Examples of metal chelates are the aluminum, titanium, or zirconium chelates of acetyl acetone, ethyl acetylacetate, salicylaldehyde, salicylaldoxime, o-hydroxyacetophenone, or ethyl trifluoroacetylacetate, and the alkoxides of these metals, and mixtures thereof.

Examples of organotin compounds are dibutyltin oxide, dibutyltin dilaurate or dibutyltin dioctoate, and mixtures thereof.

Examples of amines are, in particular, tertiary amines, for example tributylamine, triethanolamine, N-methyldiethanolamine, N-dimethylethanolamine, N-ethylmorpholine, N-methylmorpholine or diazabicyclooctane (triethylenediamine) and salts thereof, and mixtures thereof. Further examples are quaternary ammonium salts, for example trimethylbenzylammonium chloride. Amino-containing resins are simultaneously a binder and a curing catalyst. Examples thereof are amino-containing acrylate copolymers.

The curing catalyst used can also be a phosphine, for example triphenylphosphine.

The novel coating compositions can also be radiation-curable coating compositions. In this case, the binder includes monomeric or oligomeric compounds containing ethylenically unsaturated bonds, which after application are cured by actinic radiation, i.e., converted into a crosslinked, high molecular weight form. Where the system is UV-curable, it generally contains a photoinitiator as well. Corresponding systems are described in the above-mentioned publication Ullmann's Encyclopedia of Industrial Chemistry, 5th Edition, Vol. A18, pages 451–453, which is incorporated herein by reference. In radiation-curable coating compositions, the novel stabilizers can also be employed with or without additional UV light stabilizers, including sterically hindered amines.

The coating compositions according to the invention can be applied to any desired substrates, for example to metal, wood, plastic, or ceramic materials. They are preferably used as topcoats in the finishing of automobiles. If the topcoat comprises two layers, of which the lower layer is pigmented and the upper layer is not pigmented, the novel coating composition can be used for either the upper or the lower layer or for both layers, but preferably for the upper layer.

The novel coating compositions can be applied to the substrates by any conventional methods available to those or ordinary skill in the art, for example by brushing, spraying, pouring, dipping, or electrophoresis; see also Ullmann's Encyclopedia of Industrial Chemistry, 5th Edition, Vol. A18, pp. 491–500, which is incorporated herein by reference.

Depending on the binder system, the coatings can be cured at room temperature or may require heating. The coatings are preferably cured at a temperature of from about 50° C. to 150° C., and in the case of powder coatings, even at higher temperatures.

The coatings obtained in accordance with the invention generally have excellent resistance to the damaging effects of light, oxygen, and heat. In particular, the presently claimed coatings provide good light stability and weathering resistance.

In particular, the coating can be part of a paint, which has been stabilized against the damaging effects of light, oxygen, and heat by adding a content of the compound of the formulas (II)–(V), according to the invention. The paint can be a pigmented mono-coat which comprises a film-forming binder and an organic pigment or dye, an inorganic pigment, a metallic pigment, or a mixture thereof. The paint may also be a composition which comprises a primer in adhesion to a metal or plastic substrate; a pigmented basecoat that is in adhesion to the primer and which comprises a film-forming binder and an organic pigment or dye, an inorganic pigment, a metallic pigment, or a mixture thereof, and a clear coat that is in adhesion to the base coat and which comprises a film-forming binder and optionally a transparent pigment. One especially preferred use is a paint which is a clear topcoat for automobile original equipment manufacture (OEM) and/or refinish applications.

The invention furthermore relates to a process for stabilizing a coating based on polymers against damage by light, oxygen and/or heat, which comprises mixing with the coating composition one or more triazines or pyrimidines of the invention and to the use of mixtures comprising the one or more triazines or pyrimidines of the invention in coating compositions as stabilizers against damage by light, oxygen, and/or heat.

The coating compositions can comprise an organic solvent or solvent mixture in which the binder is soluble. The coating composition can otherwise be an aqueous solution or dispersion. The vehicle can also be a mixture of organic solvent and water. The coating composition maybe a high-solids paint or can be solvent-free (e.g. a powder coating material).

The pigments can be inorganic, organic or metallic pigments. The novel coating compositions preferably contain no pigments and are used as a clearcoat.

Likewise preferred is the use of the coating composition as a topcoat for applications in the automobile industry, especially as a pigmented or unpigmented topcoat of the paint finish. Its use for underlying coats, however, is also possible.

The triazines and pyrimidines of the invention may be applied topically by polishing a surface with a composition comprising the triazines or pyrimidines and an inert carrier such as solvent, petroleum jelly, silicone oil in water emulsions, or automotive paint wax, e.g. Carnauba wax. These topical treatment compositions may be used to stabilize coating films, fabrics, leather, vinyl and other plastics and wood.

Preference is also given to the use of the novel triazines and pyrimidines compounds in photographic materials as stabilizer against damage by light, especially by UV light. The invention therefore also relates to a photographic material comprising one or more triazines or pyrimidines of the invention.

The compounds according to the invention can be used for photosensitive materials of all kinds. For example, they can be employed for color paper, color reversal paper, direct-positive color material, color negative film, color positive film, color reversal film, and other materials. They are preferably used, inter alia, for photosensitive color material which comprises a reversal substrate or which forms positives.

Furthermore, the novel compounds can be combined with other UV absorbers, especially those which are dispersible in aqueous gelatin, for example with hydroxyphenylbenzotriazoles (See, e.g., U.S. Pat. Nos. 4,853,471, 4,973,702, 4,921,966 and 4,973,701), benzophenones, oxanilides, cyanoacrylates, salicylates, or acrylonitriles, or thiazolines. In this context it is advantageous to employ these further, oil-dissolved UV absorbers in the photographic material in layers other than those comprising the novel UV absorbers.

In particular, it is possible successfully to stabilize photographic materials similar to those described in U.S. Pat. No. 4,518,686.

The invention therefore additionally relates to a photographic material comprising, on support, a blue-sensitive, a green-sensitive, and/or a red-sensitive silver-halide emulsion layer and, if desired, a protective layer, with a layer comprising a UV absorber being arranged above the uppermost silver-halide emulsion layer, wherein the UV absorber is one or more triazines or pyrimidines of the invention.

Preference is additionally given to photographic materials which have a layer comprising a compound of the formula (II)–(V) above the uppermost silver-halide emulsion layer and/or between the green- and red-sensitive silver-halide emulsion layers.

Furthermore, it may be advantageous for all or some of the layers which can comprise a UV absorber to have a UV absorber mixture and/or a further UV absorber which is dispersible in aqueous gelatin, but a compound of the formula (II)–(V) must be present at least in one layer.

The novel material preferably has gelatin interlayers between the silver-halide emulsion layers.

Preference is given to photographic materials in which the silver halide in the blue-sensitive, green-sensitive, and/or red-sensitive layer is silver chloride bromide comprising at least 90 mol % of silver chloride.

The compounds of the formula (II)–(V), which are used in accordance with the invention, can be incorporated, alone or together with the color coupler and, if used, further additives, into the color photographic materials by dissolving the compounds beforehand in high-boiling organic solvents. It is preferred to use solvents which boil at higher than 1560° C. Typical examples of such solvents are the esters of phthalic acid, phosphoric acid, citric acid, benzoic acid or of fatty acids; alkylamides; or phenols.

Preferred color couplers for use in the compositions of the invention; examples of such compounds; further additives such as color cast inhibitors, DIR couplers and further light stabilizers, such as UV absorbers, phenols, phosphorus (III) compounds, organometallic complexes, hydroquinones and hydroquinone ethers; and more precise details on the structure of various photographic materials, can be found, for example, in the publications EP-A-0531258 and EP-A-0520938 and in the literature cited therein.

The invention also relates to a process for the stabilization of polyolefin or polyolefin copolymer films for agricultural applications, especially greenhouse applications, this polyolefin or polyolefin copolymer film having improved light stability and pesticide resistance, comprises one or more triazines or pyrimidines of the invention and a metal oxide or hydroxide selected from oxides of zinc, aluminum, calcium and magnesium, and hydroxides of zinc, aluminum and calcium, into the polyolefin or polyolefin copolymer. A further subject of the invention is a greenhouse, characterized in that it is covered by a polyolefin or polyolefin copolymer film having improved light stability and pesticide resistance and stabilized with one or more triazines or pyrimidines of the invention and a metal oxide or hydroxide selected from oxides of zinc, aluminum, calcium and magnesium, and hydroxides of zinc, aluminum and calcium; and a process for stabilizing a polyolefin or polyolefin copolymer greenhouse film against detrimental effects of pesticides and light, oxygen and/or heat, which process comprises incorporating one or more triazines or pyrimidines of the invention and a metal oxide or hydroxide selected from oxides of zinc, aluminum, calcium and magnesium, and hydroxides of zinc, aluminum and calcium, into said greenhouse film.

To form a film, a quantity of the said melted composition is forced through a film die, such as a flat film die or a circular blown film die, and forming a film therefrom. In the case where the composition is used to form a film therefrom, it is contemplated that the films may be unoriented, or may be subjected to a conventional operation to impart a degree of orientation on the film. Such a film may be oriented in one direction, such as in the "machine direction" and/or the "transverse direction," or may be oriented in both directions, or "biaxially" oriented.

The present invention is also suitable for sheet applications.

The triazines and pyrimidines of the formula (II)–(V) are suitable for the photochemical stabilization of undyed, dyed, or printed fiber materials comprising for example, silk, leather, wool, polyamide, or polyurethanes and especially cellulose-containing fiber materials of all kinds. Examples of such fiber materials are the natural cellulose fibers, such as cotton, linen, jute, and hemp and also viscose staple fiber and regenerated cellulose. Preferred textile fiber materials are those of cotton. The triazine and pyrimidine compounds of the present invention are also suitable for the photochemical stabilization of hydroxyl-containing fibers in blend fabrics, for example blends of cotton with polyester fibers or polyamide fibers. A further preferred area of application relates to the blocking or reduction of the UV radiation which passes through the above-mentioned textile materials (UV cutting) and the heightened sun protection that textile materials finished with the novel compounds of the invention offer to the human skin.

To this end, one or a number of different compounds of the formula (II)–(V) are applied to the textile fiber material by one of the customary dyeing methods, advantageously in a quantity of 0.1 to 5% by weight, preferably 0.1 to 3% by weight and, in particular, from 0.25 to 2% by weight, based on the weight of the fiber material.

The triazine and pyrimidine compounds can be applied to the fiber material in various ways and fixed on the fiber, especially in the form of aqueous dispersions or printing pastes.

The textile fiber materials finished with the novel compounds of the formula (II)–(V) possess improved protection against photochemical breakdown of the fiber and yellowing phenomena and, in the case of dyed fibre material, are of enhanced (hot) light fastness. Particular emphasis should be drawn to the greatly improved photoprotective effect of the treated textile fiber material and, in particular, the good protective effect with respect to short-wave UV-B rays. This is manifested by the fact that the textile fiber material finished with the novel triazine or pyrimidine compounds of the invention have, relative to untreated fabric, a greatly increased sun protection factor (SPF).

The sun protection factor is defined as the quotient of the dose of UV radiation which damages protected skin to that which damages unprotected skin. Accordingly, a sun protection factor is also a measure of the extent to which untreated fiber materials and fiber materials treated with novel compounds of the formulas (II)–(V) are permeable to UV radiation. The determination of the sun protection factor of textile fiber materials is explained, for example, in WO94/04515 or in J. Soc. Cosmet. Chem. 40, 127–133 (1989) and can be carried out analogously thereto.

Yet another use of the UV absorbers according to the invention is in the stabilization of intra-ocular and contact lenses.

The inventive UV absorbers are also suitable as photoprotective agents in cosmetic preparations. The invention additionally relates, therefore, to a cosmetic preparation comprising at least one triazine or pyrimidine compound of the invention and cosmetically acceptable carriers or auxiliaries.

The novel cosmetic composition contains from 0.1 to 15% by weight, preferably from 0.5 to 10% by weight, based on the overall weight of the composition, of at least one triazine or pyrimidine UV absorber of the invention and a cosmetically acceptable auxiliary.

The cosmetic composition can be prepared by physically mixing the novel UV absorber with the auxiliary by means of customary methods, for example by simply stirring together the two materials.

The cosmetic preparation according to the invention can be formulated as a water-in-oil or oil-in-water emulsion, as an oil-in-oil alcohol lotion, as a vesicular dispersion of an ionic or nonionic amphiphilic lipid, as a gel, solid stick, or as an aerosol formulation.

As a water-in-oil or oil-in-water emulsion, the cosmetically acceptable auxiliary preferably contains from 5 to 50% of an oily phase, from 5 to 20% of an emulsifier, and from 30 to 90% water. The oil phase can comprise any oil which is suitable for cosmetic formulations, e.g., one or more hydrocarbon oils, a wax, a natural oil, a silicone oil, a fatty acid ester, or a fatty alcohol. Preferred mono- or polyols are ethanol, isopropanol, propylene glycol, hexylene glycol, glycerol, and sorbitol.

For these cosmetic formulations, it is possible to use any conventionally employed emulsifier, e.g., one or more ethoxylated esters of naturally occurring derivatives, i.e., polyethoxylated esters of hydrogenated castor oil; or a silicone oil emulsifier such as silicone polyol; an unmodified or ethoxylated fatty acid soap; an ethoxylated fatty alcohol; an unmodified or ethoxylated sorbitan ester; an ethoxylated fatty acid; or an ethoxylated glyceride.

The cosmetic formulation can also comprise further components, for example emollients, emulsion stabilizers, skin moisteners, tanning accelerators, thickeners such as xanthan, moisture retention agents such as glycerol, preservatives, fragrances, and colorants.

The novel cosmetic formulations are notable for good protection of human skin against the damaging effect of sunlight while at the same time providing for reliable tanning of the skin.

The invention will now be illustrated by the following examples. The examples are not intended to be limiting of the scope of the present invention. In conjunction with the general and detailed descriptions above, the examples provide further understanding of the present invention.

EXAMPLES

Examples and reaction schemes for producing specific examples of novel triazines of the invention in accordance with the invention are provided below. While the following examples illustrate preparations with one or more triazines of the invention compounds, one of ordinary skill will understand that these reactions may also be carried out with any of a variety of other phenyl compounds having hydrocarbyl groups ortho to each other where, when necessary, reactive substituents on such other phenyl compounds having hydrocarbyl groups ortho to each other are protected in accordance with procedures and reagents well known and understood by those of ordinary skill in the art.

Example 1

Synthesis of 2-(2,4-dihydroxphenyl)-4,6-(3,4-dimethylphenyl)-1,3,5-triazine from Cyanuric Chloride in Chlorobenzene Solvent

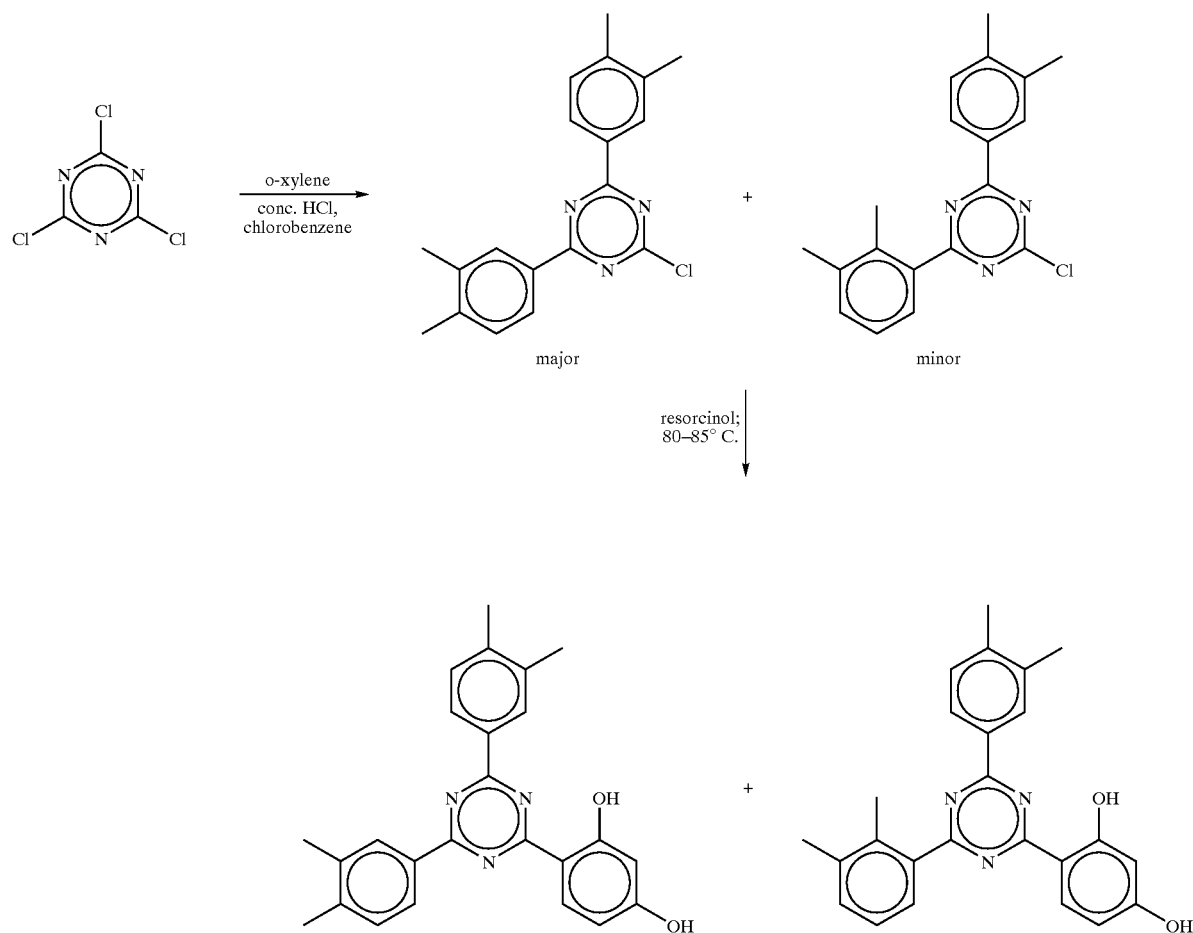

In a 3 neck round bottom flask equipped with a mechanical stirrer, a refluxing condenser, a nitrogen inlet, and a thermocouple, was added 55.3 g cyanuric chloride and 750 ml chlorobenzene. The reaction flask was then cooled in an ice-bath to about 0° C., and then 120.0 g of AlCl₃ was slowly added with stirring. After about 5 minutes, 6.0 g of concentrated hydrochloric acid was added. The reaction mixture was stirred for about 30 minutes at 0° C., further cooled to about −5° C., and 60.5 g of o-xylene was then added over a period of about 35–40 minutes. The reaction mixture was stirred at 0° C. for about 1 hour and then stirred at room temperature for 6 hours. Resorcinol (36.3 g) was then added to the reaction mixture and the resulting mixture allowed to stir for about 12 hours. The reaction mixture was then heated to about 85–90° C. for 3 hours. HPLC analysis at this stage indicated completion of the reaction. The reaction mixture was then cooled to about 50° C., and quenched with dilute HCl solution. The chlorobenze solvent was removed by azeotropic distillation. The precipitated material was separated by filtration, washed with water, and dried to give 96 g of the product analyzed to consist mainly of the 2-(2,4-dihydroxphenyl)-4,6-(3,4-dimethylphenyl)-1,3,5-triazine along with a small amount of its isomer.

Example 2

Preparation of 2-(2-hydroxy-4-octyloxyphenyl-4,6-(3,4-dimethylphenyl)-1,3,5-triazine

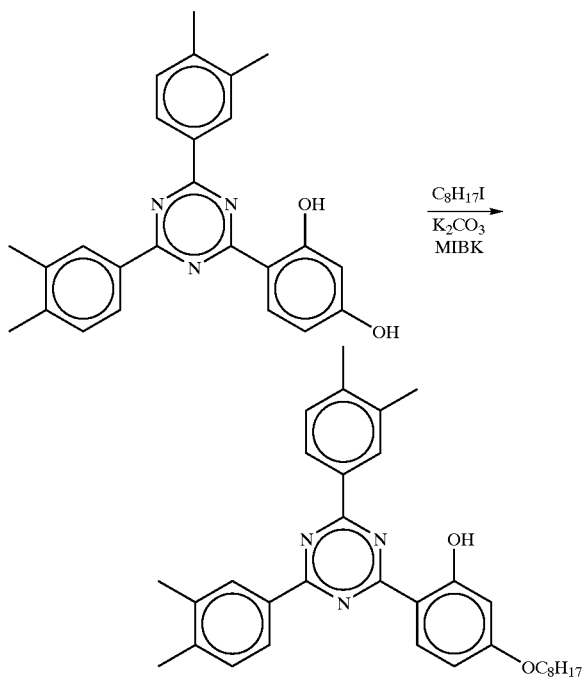

To a reaction flask equipped with a mechanical stirrer, a refluxing condenser, nitrogen inlet, and a thermocouple was added 90 gm of 2-(2,4-dihydroxphenyl)-4,6-(3,4-dimethylphenyl)-1,3,5-triazine (as made in Example 1), 124.4 g of potassium carbonate, 59.4 g of iodooctane, 2 g Alliquat-336, and 750 ml of methyl isobutyl ketone (MIBK). The reaction mixture was heated to reflux for 7 hrs. HPLC data showed the formation of a new product and disappearance of the 2-(2,4-dihydroxphenyl)-4,6-(3,4-dimethylphenyl)-1,3,5-triazine. The reaction mixture was cooled to room temperature, diluted with methylene chloride, filtered, and the filtrate concentrated under reduced pressure. The resulting residue was dissolved in methylene chloride, washed with water, dried, and concentrated to give 111 gm of crude product. The crude product was refluxed with acetone, and the solid filtered after cooling to room temperature, washed with acetone, and dried to give 75 gm of pure 2-(2-hydroxy-4-octyloxyphenyl-4,6-(3,4-dimethylphenyl)-1,3,5-triazine, melting point 140° C.

Example 3

Synthesis of 2-(2,4-dihydroxyphenyl)-4,6-(3,4-dimethylphenyl)-1,3,5-triazine from cyanuric chloride in o-dichlorobenzene solvent.

In a 3 neck, glass round bottom flask equipped with a mechanical stirrer, a refluxing condenser with nitrogen inlet and a thermocouple was added 50 g cyanuric chloride and 191 ml o-dichlorobenzene (ODCB). AlCl$_3$ (108.4 g) was then slowly added to the flask at room temperature. After few minutes, the reaction mixture was cooled in an ice-bath, and 6.5 g of HCl was added to the reaction mixture. The reaction mixture was allowed to warm to room temperature, stirred for 2 hours, 54.7 g of o-xylene added over a 3 hour period, and the reaction mixture stirred overnight at room temperature. The reaction mixture was heated to about 63° C., and 34 g of resorcinol was added in four equal parts in 10 minute intervals. The mixture was heated at 75–80° C. for 3 hours. The reaction mixture was then cooled to room temperature and quenched with water. The o-dichlorobenzene was distilled off as an azeotrope. The precipitated solid was filtered off, washed with water, and dried to give 96 gm of crude -(2,4-dihydroxyphenyl)-4,6-(3,4-dimethylphenyl)-1,3,5-triazine.

Example 4

Preparation of 2-chloro-4,6-bis(3,4-dimethylphenyl-1,3,5-triazine

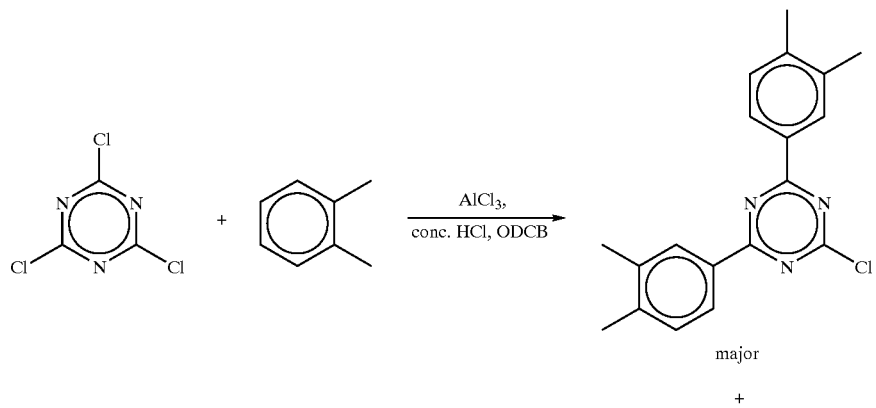

major

+

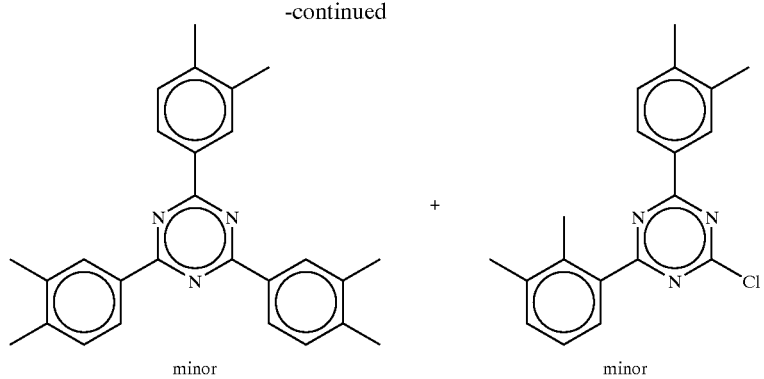

minor     +     minor

To a 3-neck round bottom glass reaction flask equipped with reflux condenser, a stirrer, and a nitrogen inlet was added 3.69 g of cyanuric chloride and 50 ml o-dichlorobenzene (ODCB). AlCl$_3$ (8.0 g) was then added to the reaction mixture at room temperature. The mixture was cooled to about 5° C. using an ice bath and 0.5 g of concentrated HCl was added and the reaction mixture stirred at room temperature for 3–4 hours. The reaction mixture was cooled to about 5–10° C., 4.0g of o-xylene was added with stirring, and the reaction mixture allowed to stir at room temperature for about 20 hours. The reaction mixture was then quenched by adding water, and the o-dichlorobenzene was removed by azeotropic distillation. The resulting solid material was filtered and was dried overnight to give about 5.5 g of a crude product. The major product was confirmed by HPLC analysis to be 2-chloro-4,6-bis(3,4-dimethylphenyl)-1,3,5-triazine.

Example 5

Reaction of 2-(2,4-dihydroxphenyl)-4,6-bis(3,4-dimethylphenyl)-1,3,5-triazine with Ethyl Chloroacetate in the Presence of a Base To a reaction flask equipped with a reflux condenser, a stirrer, and a nitrogen inlet was added 2.0 g of 2-(2,4-dihydroxyphenyl)-4,6-bis(3,4-dimethylphenyl)-1,3,5-triazine, 3.5 g potassium carbonate, 0.1 g potassium iodide, and 20 ml acetone followed by 1.1 mole eq. of ethyl chloroacetate. The reaction mixture was then heated to reflux, and held at reflux for 6 hours. HPLC analysis of the reaction mixture showed the formation of a new product with almost complete conversion of the starting material. The heating was discontinued, the reaction mixture was cooled to room temperature, and filtered to provide a residue. The residue was treated with water and then extracted with methylene chloride. The filtrate and the methylene chloride extract were combined and concentrated to give about 1.0 g of a product identified to be 2-[2-hydroxy-4-ethoxycarbonylmethoxyphenyl]-4,6-bis-[3,4-dimrthylphenyl]-1,3,5-triazine.

Example 6

Reaction of 2-(2,4-dihydroxyphenyl)-4,6-bis(3,4-dimethylphenyl)-1,3,5-triazine with Iodobutane in the Presence of a Base

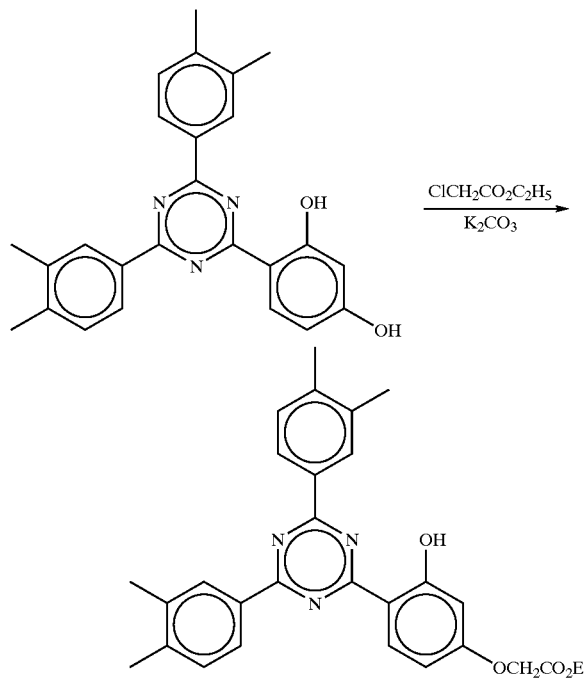

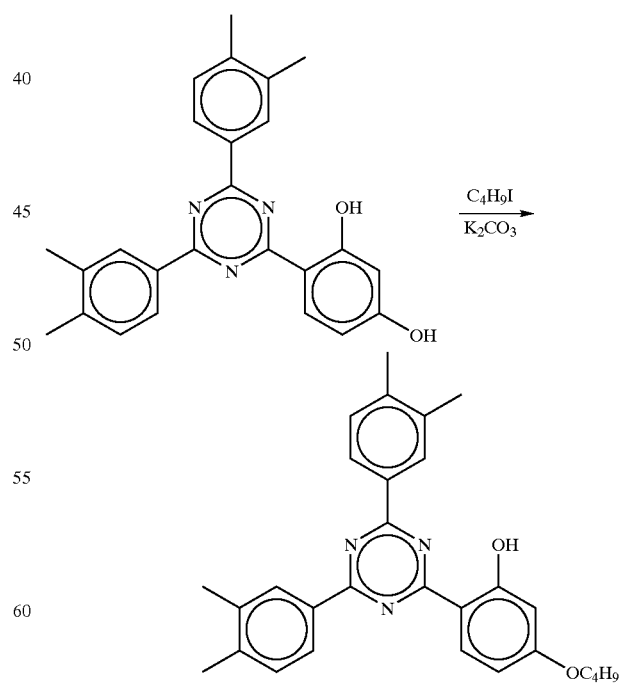

To a reaction flask equipped with a reflux condenser, a stirrer and a nitrogen inlet was added 1.0 g of 2-(2,4-dihydroxyphenyl)-4,6-bis(3,4-dimethylphenyl)-1,3,5- triazine, 3.5 g potassium carbonate, 0.1 g of Aliquat 336, and 20 ml acetone followed by 1.1 mole eq. of iodobutane. The reaction mixture was then heated to reflux, and held at relfux for 6 hours. HPLC analysis of the reaction mixture showed the formation of a new product with almost complete conversion of the starting material. The heating was discontinued, and the reaction mixture was cooled to room temperature. The reaction mixture was diluted with water and extracted with methylene chloride. The methylene chloride extract was washed with water, dried, and concentrated to give 2.0 g of a product identified to be 4-butyl ether derivative of 2-(2,4-dihydroxyphenyl)-4,6-bis(3,4-dimethylphenyl)-1,3,5-triazine.

Example 7

Reaction of 2-(2,4-dihydroxyphenyl)-4,6-bis(3,4-dimethylphenyl)-1,3,5-triazine with Benzenesulfonyl Chloride in the Presence of a Base

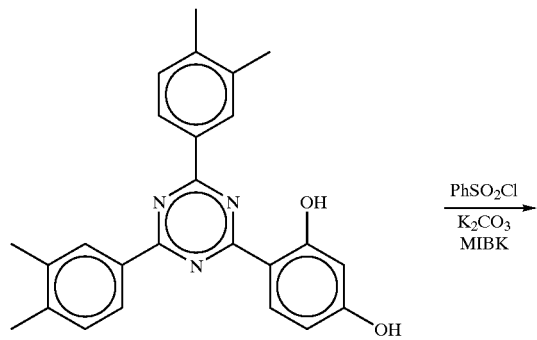

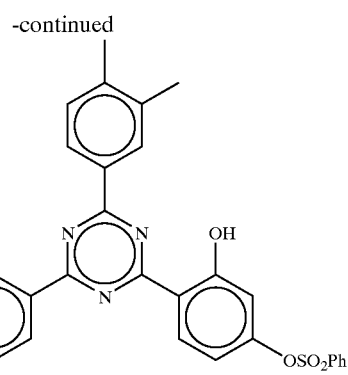

To a reaction flask equipped with a reflux condenser, a stirrer, and a nitrogen inlet was added 3.97 g of 2-(2,4-dihydroxyphenyl)-4,6-bis(3,4-dimethylphenyl)-1,3,5-triazine, 4.14 g potassium carbonate, and 30 ml of methyl isobutyl ketone (MIBK) followed by 1.8 g of benzenesulfonyl chloride. The reaction mixture was then heated to reflux, and held at reflux for 10 hours. HPLC analysis of the reaction mixture showed the formation of a new product with almost complete conversion of the starting material. The heating was discontinued, and the reaction mixture was cooled to room temperature. The reaction mixture was then diluted with methylene chloride, filtered, and the filtrate concentrated under reduced pressure. The resulting residue was treated with a mixture of 1:1 methylene chloride:hexane and the resulting precipitated material collected by filtration and dried to give the 4-benzenesulfonate derivative that was characterized by NMR and mass spectral analysis.

Example 8

Reaction of 2-(2,4-dihydroxyphenyl)-4,6-bis(3,4-dimethylphenyl)-1,3,5-tri azine, with benzenesulfonyl chloride in the presence of aluminum chloride without isolation of the 2-(2,4-dihydroxyphenyl)-4,6-bis(3,4-dimethylphenyl)-1,3,5-triazine

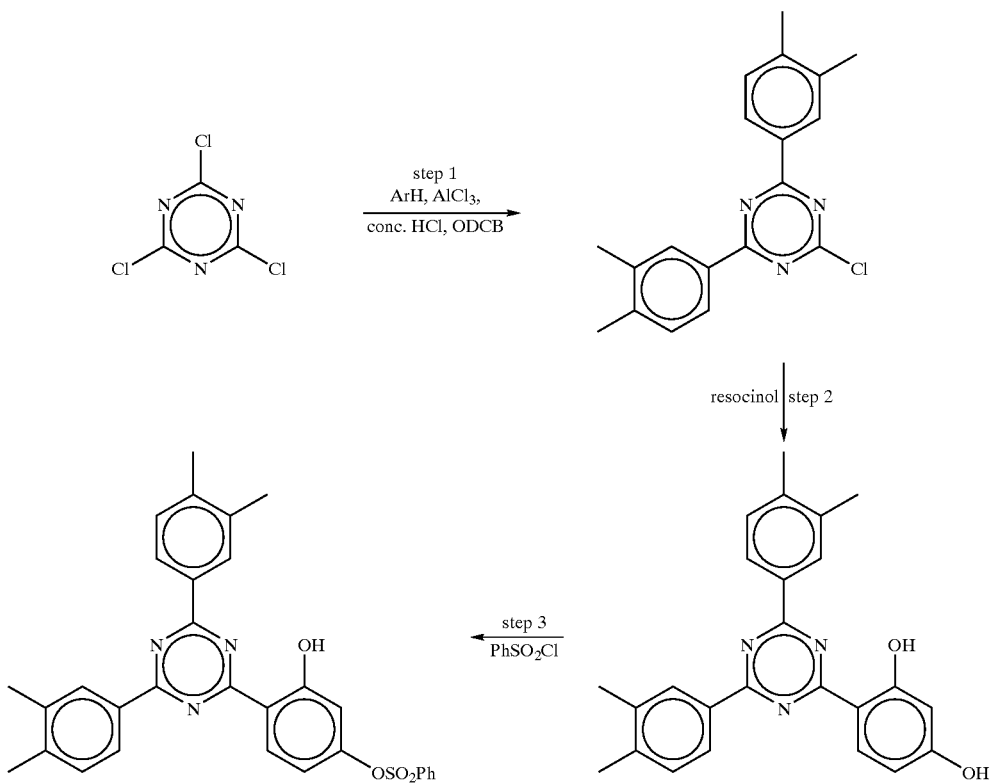

To a reaction flask equipped with a reflux condenser, a stirrer, and a nitrogen inlet was added 3.7 g of cyanuric chloride, 50 mL of o-dichlorobenzene, and 8.0 g of aluminum chloride. The reaction mixture was cooled to 5° C. in an ice-bath, and 0.5 g of concentrated HCl was slowly added. The ice-bath was then removed, the mixture was stirred at room temperature for 3 hours, 4 g of o-xylene was added to the reaction mixture over a period of 10 min. at room temperature, and the reaction mixture was stirred at room temperature for about 16 hours. Resorcinol (2.4 g) was then added to the reaction mixture and the reaction mixture was heated to 85–90° C., and held at this temperature for 2 hours. The reaction mixture was then cooled to room temperature and 3.9 g of benzene sulfonyl chloride slowly added. The reaction mixture was heated again to 85–90° C. for 5 hours, and then allowed to sit at room temperature for about 12 hours. The reaction mixture was then quenched with water, extracted with methylene chloride, and the organic extract concentrated under reduced pressure. HPLC analysis of the residue showed that the major product was identical to the 4-benzene sulfonate derivative prepared above in Example 7. This one pot process, wherein intermediates are not isolated is a novel method to make this class of compounds.

Example 9

Reaction of 2-(2,4-dihydroxyphenyl)-4,6-bis(3,4-dimethylphenyl)-1,3,5-triazine with Benzoyl Chloride in the Presence of a Base

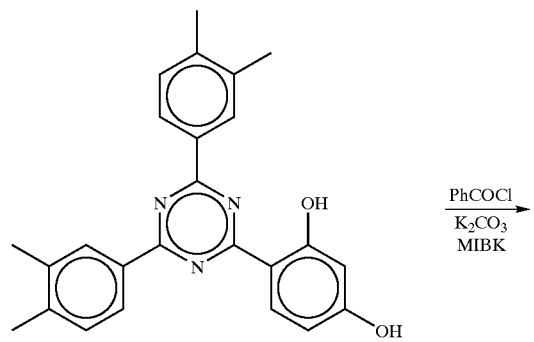

-continued

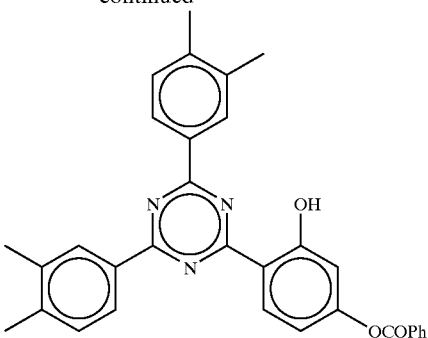

To a reaction flask equipped with a reflux condenser, a stirrer, and a nitrogen inlet was added 3.97 g of 2-(2,4-dihydroxyphenyl)-4,6-bis(3,4-dimethylphenyl)-1,3,5-triazine, 4.14 g potassium carbonate, and 30 ml of methyl isobutyl ketone (MIBK) followed by 1.4 g of benzoyl chloride. The reaction mixture was then heated to reflux, and held at reflux for 10 hours. HPLC analysis of the reaction mixture showed the formation of a new product and unreacted starting material. An additional 0.5 g of benzoyl chloride was added to the reaction mixture and the reaction mixture refluxed for an additional 10 hours. The heating was discontinued, and the reaction mixture was cooled to room temperature. The reaction mixture was then diluted with methylene chloride, filtered, and the filtrate concentrated under reduced pressure. The resulting residue was further purified by column chromatography over silica gel using a 75:25 methylene chloride:hexane mixture as the eluant. About 2.0 g of a product characterized to be the 4-benzoate derivative was recovered.

Example 10

Reaction of 2-(2,4-dihydroxyphenyl)-4,6-bis(3,4-dimethylphenyl)-1,3,5-triazine with Benzoly Chloride in the Presence of Aluminum Chloride Without Isolation of the 2-(2,4-dihydroxphenyl)-4,6-bis(3,4-dimethylphenyl)-1,3,5-triazine

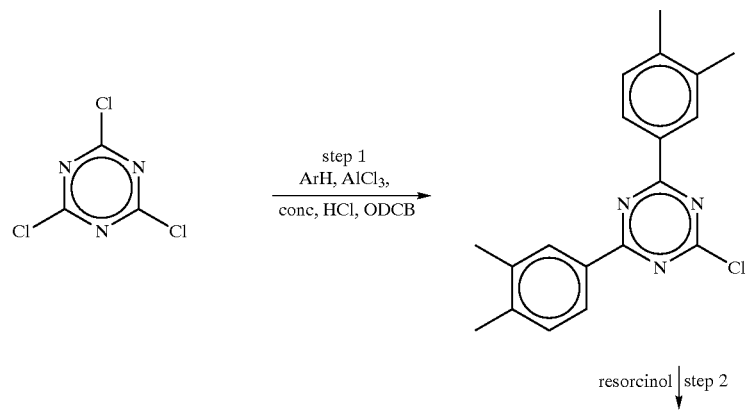

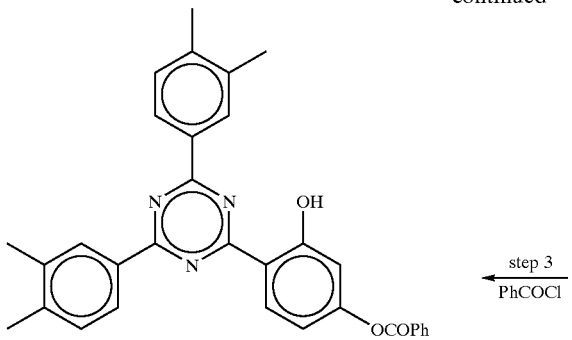

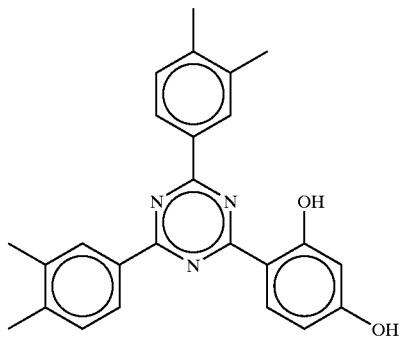

To a reaction flask equipped with a reflux condenser, a stirrer, and a nitrogen inlet was added 3.7 g of cyanuric chloride, 50 mL of o-dichlorobenzene (ODCB), and 8.0 g of aluminum chloride. The reaction mixture was cooled to 5° C. in an ice-bath, and 0.5 g of concentrated HCl was slowly added. The ice-bath was then removed, the mixture was stirred at room temperature for 3 hours, and 4 g of o-xylene was then added over a period of 10 min. at room temperature. The reaction mixture was stirred at room temperature for about 6 hours, 2.4 g of resorcinol was added to the reaction mixture, and the reaction mixture was heated to 85–90° C., and held at this temperature for 2 hours. The reaction mixture was cooled to room temperature, 3.1 g of benzoyl chloride was added, the reaction mixture was heated again to 85–90° C. for 5 hours, and allowed to sit at room temperature for about 12 hours. The reaction mixture was then quenched with water, extracted with methylene chloride, and the organic extract concentrated under reduced pressure. HPLC analysis of the residue showed a mixture of products including the 4-benzoate ester of 2-(2,4-dihydroxyphenyl)-4,6-bis(3,4-dimethylphenyl)-1,3,5-triazine. This one pot process, wherein intermediates are not isolated is a novel method to make this class of compounds.

Example 11

Reaction of 2-(2,4-dihydroxyphenyl)-4,6-bis(3,4-dimethylphenyl)-1,3,5-triazine with 2-t-butyl-5-chloromethyl-4-6-dimethylphenol in the Presence of a Base

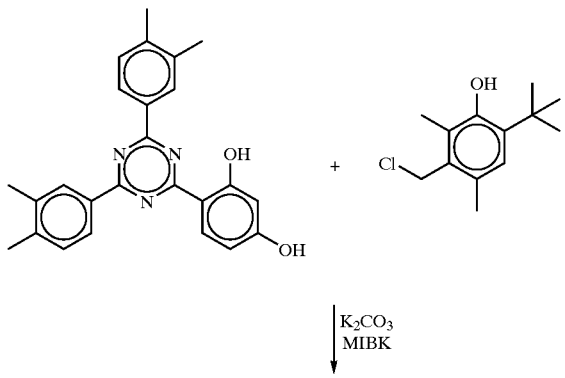

-continued

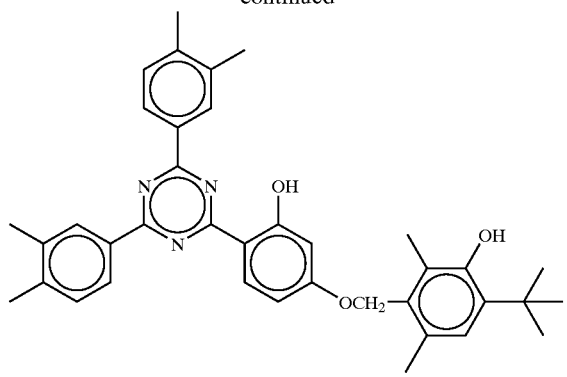

To a reaction flask equipped with a reflux condenser, a stirrer, and a nitrogen inlet was added 3.97 g of 2-(2,4-dihydroxyphenyl)-4,6-bis(3,4-dimethylphenyl)-1,3,5-triazine, 4.14 g potassium carbonate, 0.25 g Aliquat 336, and 30 ml of methyl isobutyl ketone (MIBK) followed by 2.1 g of 2-t-butyl-5-chloromethyl-4-6-dimethylphenol. The reaction mixture was then heated to reflux, and held at reflux for 10 hours. HPLC analysis of the reaction mixture showed the formation of a new product. Heating was discontinued, and the reaction mixture was cooled to room temperature. The reaction mixture was diluted with methylene chloride, filtered, and the filtrate concentrated under reduced pressure. The resulting residue was purified by column chromatography over silicia gel using a mixture of 75:25 methylene chloride:hexane as the eluant. The recovered product, 2-[2-hydroxy-4-[2,6-dimethyl-3-hydroxy-4-t-butylphenyl] methoxyphenyl]-4,6-bis[3,4-dimethylphenyl]-1,3,5-triazine, was characterized on the basis of NMR and mass spectral product.

Performance of the Triazine Light Stabilizers of the Invention

Example 12

Performance of 2-(2-hydroxy-4-octyoxylphenyl)-4,6-bis(3,4-dimethylphenyl-1,3,5-triazine (Compound A) in Polycarbonate Plaques Compound A at a loading level of 0.35%, 0.2%, or 0.1% by weight and 0.05% phosphite (Ultranox 641, commercially available from General Electric Specialty Chemicals of) Morgantown, W.Va. was dry blended into a Lexan101-1111 polycarbonate pellets (containing 0.5% phosphite) or Lexan 100 virgin polycarbonate flakes (both commercially available from General Electric Specialty Chemicals of Morgantown, W.Va.). The blended material was melt mixed in a Brabender PL-2000 torque rheometer (commercially available from Pasedena Hydraulics of The City of Industry, Calif.) equipped with a single mixing screw extruder, 5-zone, single pass at 50–60 rpm with the temperature of zones 1–5 at 246° C., 260° C., 265° C., 295° C., and 300° C., respectively. The extrudate was cooled dried and pelitized. The pellets were injection molded into sample plaques (2 inches×2.5 inches×125 mils) using an Arburg Allrounder 320-210-750 injection molding machine (commercially available from Arbury GmbH & Co. of Lossburg, Germany) with the nozzle at 295° C., nozzle side at 300° C., middle at 285° C., feed at 275° C., and mold at 105° C. Control plaques, without Compound A, were prepared in an identical manner.

Plaques were tested for hydrolytic stability by measuring the melt flow index of the polycarbobate plaques as g per 10 minutes, using a CSI Melt Flow Indexer 2 (commercially available from Custom Scientific Instruments, a Division of Atlas Electric Devices Co. of Cedar Knolls, N.J.) following ASTM D1238 method B, before and after being exposed to high temperature and pressure. Samples were exposed to high temperature and pressure in an All-American Electric Pressure Sterilizer Model No. 25X (commercially available from PCI Scientific Supply Inc., of Faitfield, N.J.). The autoclave was pressurized with water at 120° C. for 6 hours. Sample plaques exposed to high temperature and pressure were dried over a desiccant in an oven for between 4 and 8 hours before measuring the flow index. The results of hydrolytic testing are provided in Table 1.

TABLE 1

Hydrolytic Stability, Effect on Melt Flow Index.

| Additive | Melt Flow Index (g/10 min) | |
| --- | --- | --- |
| | Before | After |
| Compound A (0.35% loading + 0.1% phosphite) | 6.1 | 6.8 |
| Control | 6.2 | 8 |

The results in Table 1 show that the Compound A had no significant effect on the stability of the polycarbonate plaques, as measured by the melt flow index. Control plaques without compound A appeared to show a distinct increase in the melt flow index after being subjected to high temperature and pressure.

Sample plaques were also subjected to xenon-arc accelerated weathering, QUV accelerated weathering, and oven aging at 130° C. Xenon-arc accelerated weathering was carried out by exposing the sample plaques in a xenon-arc weatherometer as determined by the ASTM G-26 Standard using Test Method B. QUV (UVB-313) accelerated weathering was carried out on plaques according to the ASTM G-53 test method with a QUV Accelerated Weather Tester device (commercially available from Q Panel Laboratory Products of Cleveland, Ohio). Oven aging was carried out according to the ASTM 794 test method. Color as measured by yellowing index (YI) and ΔE was measured as a function of weathering time. Color was determined with a Macbeth Color Eye Colorimeter under laboratory conditions with illuminate C, 2° observer, specular component excluded, and UV component included.

Tables 2 to 4 show the effect of xenon-arc accelerated weathering, oven aging, and QUV (UVB-313) accelerated weathering, respectively, as measured by YI values, for polycarbonate plaques containing 0.35% by weight of Compound A and for control polycarbonate plaques. Table 5 show the effect on YI, ΔE, and ΔYI (YI at time t less YI at time 0) on polycarbonate plaques including 0.35% by weight of Compound A compared to a control polycarbonate plaques that were subjected to oven aging.

TABLE 2

Xenon-arc Accelerated Weathering of a Polycarbonate Plaque Stabilized with Compound A, Effect on YI.

| Additive | Exposure (hours) | | | |
| --- | --- | --- | --- | --- |
| | 0 | 400 | 800 | 1200 |
| Compound A (0.35% loading + 0.1% phosphite) | 6.4 | 13.2 | 15.8 | 17.1 |
| Control | 3.1 | 20.9 | 24.3 | 29.9 |

TABLE 3

Oven Aging at 130° of a Polycarbonate Plaque Stabilized with Compound A, Effect on YI.

| Additive | Exposure (hours) | | | |
| --- | --- | --- | --- | --- |
| | 0 | 400 | 540 | 800 |
| Compound A (0.35% loading + 0.05% phosphite) | 12.6 | 11.2 | 15.3 | 20.7 |
| Control | 8.4 | 21.9 | 30.8 | 37.6 |

TABLE 4

QUV (UVB-313) Accelerated Weathering of a Polycarbonate Plaque Stabilized with Compound A, Effect on YI.

| Additive | Exposure (hours) | | | | | | |
| --- | --- | --- | --- | --- | --- | --- | --- |
| | 0 | 20 | 40 | 60 | 80 | 100 | 120 |
| Compound A (0.35% loading + 0.05% phosphite) | 8.7 | 10.1 | 11.5 | 13.4 | 14.9 | 16.5 | 18.3 |
| Control | 7 | 13.5 | 17.9 | 21.9 | 24.8 | 28.3 | 29.8 |

TABLE 5

Oven Aging at 130° C. of a Polycarbonate Plaque Stabilized with Compound A, Effect on YI, ΔE, and ΔYI.

YI Values

| Additive | Exposure (hours) | | | | | |
| --- | --- | --- | --- | --- | --- | --- |
| | 0 | 50 | 100 | 150 | 200 | 250 |
| Compound A (0.35% loading + 0.05% phosphite) | 8.5 | 9.7 | 10.2 | 10.4 | 11.5 | 12.4 |
| Control | 6.4 | 7.9 | 9 | 10.1 | 12.3 | 14.5 |

| | Exposure (hours) | | | | |
| --- | --- | --- | --- | --- | --- |
| | 50 | 100 | 150 | 200 | 250 |
| ΔE Values | | | | | |
| Compound A (0.35% loading + 0.05% phosphite) | 0.7 | 0.9 | 1 | 1.6 | 2.1 |
| Control | 0.8 | 1.4 | 2 | 3.2 | 4.4 |
| ΔYI Values | | | | | |
| Compound A (0.35% loading + 0.05% phosphite) | 1.2 | 1.7 | 1.9 | 3.0 | 3.9 |
| Control | 1.5 | 2.6 | 3.7 | 5.9 | 8 |

The results in Tables 2–5 clearly shows that the polycarbonate plaques stabilized with Compound A showed superior performance compared to the polycarbonate plaque containing no stabilizer, as measured by YI, ΔYI, and ΔE, when subjected to xenon-arc accelerated weathering, QUV (UVB-313) accelerated weathering, or oven aging. An increase in YI, ΔYI or ΔE indicates an unfavorable discoloration of the polycarbonate.

Performance of the Triazine Light Stabilizers of the Invention Compared to Conventional Triazine Light Stabilizers Example 13

Comparison of the Performance of 2-(2-hydroxy-4-octylozyphenyl)-4,6-bis(3,4-dimethylphenyl-1,3,5-triazine (Compound A) Against 2-(2-hydroxy-4-octyloxyphenyl)-4,6-(bis(2,4-dimethylphenyl-1,3,5-triazine (UV-1164) in Polycarbonate Plaques Polycarbonate sample plaques were prepared as described in Example 12 containing 0.35%, 0.2%, or 0.1% by weight of Compound A or UV-1164 (commercially available from Cytec Industries of West Paterson, N.J.). The sample plaques were tested for hydrolytic stability and subjected to xenon-arc accelerated weathering, QUV accelerated weathering, and oven aging at 130° C. according to the procedures described in Example 12. The results of hydrolytic testing are provided in Table 6.

TABLE 6

Hydrolytic Stability, Effect on Melt Flow Index.

| Additive | Melt Flow Index (g/10 min) | |
| --- | --- | --- |
| | Before | After |
| Compound A (0.35% loading + 0.1% phosphite) | 6.1 | 6.8 |
| UV-1164 (0.35% loading + 0.1% phosphite) | 6.8 | 9.8 |

The results in Table 6 show that Compound A had no significant effect on the stability of the polycarbonate plaques. Plaques containing UV-1164 appeared to show a significant increase in the melt flow index after being subjected to high temperature and pressure.

Tables 7 shows a comparison of the effect of oven aging on YI values in polycarbonate plaques including 0.35% by weight of Compound A or UV-1164. Table 8 shows the effect of oven aging on YI, ΔE, and ΔYI values in polycarbonate plaques including 0.35 and 0.1 by weight of Compound A or UV-1164.

TABLE 7

Oven Aging at 130° C. of a Polycarbonate Plaque Stabilized with Compound A or UV-1164, Effect on YI.

| Additive | Exposure (hours) | | | | | |
| --- | --- | --- | --- | --- | --- | --- |
| | 0 | 100 | 200 | 440 | 540 | 600 |
| Compound A (0.35% loading + 0.05% phosphite) | 6.3 | 7.4 | 7.8 | 8.4 | 8.8 | 9 |
| UV-1164 (0.35% loading + 0.05% phosphite) | 10.4 | 14.9 | 16.3 | 17.9 | 18.2 | 18.6 |

TABLE 8

Oven Aging at 130° C. of a Polycarbonate Plaque Stabilized with Compound A or UV-1164, Effect on YI, ΔE, and ΔYI.

YI Values

| Additive | Exposure (hours) | | | | | |
| --- | --- | --- | --- | --- | --- | --- |
| | 0 | 50 | 100 | 150 | 200 | 250 |
| Compound A (0.35% loading + 0.05% phosphite) | 8.5 | 9.7 | 10.2 | 10.4 | 11.5 | 12.4 |
| UV-1164 (0.35% loading + 0.65% phosphite) | 11.2 | 12.9 | 13.7 | 14.3 | 16.4 | 18.3 |
| Compound A (0.1% loading + 0.05% phosphite) | 6.7 | 8.1 | 8.8 | 9.8 | 11.2 | 12.7 |
| UV-1164 (0.1% loading + 0.05% phosphite) | 11.6 | 13.4 | 14.7 | 16.7 | 18.8 | 21.1 |

| | Exposure (hours) | | | | |
| --- | --- | --- | --- | --- | --- |
| | 50 | 100 | 150 | 200 | 250 |

ΔE Values

| Compound A (0.35% loading + 0.05% phosphite) | 0.7 | 0.9 | 1 | 1.6 | 2.1 |
| --- | --- | --- | --- | --- | --- |
| UV-1164 (0.35% loading + 0.05% phosphite) | 0.9 | 1.4 | 1.8 | 2.9 | 4 |
| Compound A (0.1% loading + 0.05% phosphite) | 0.8 | 1.2 | 1.8 | 2.4 | 3.3 |
| UV-1164 (0.1% loading + 0.05% phosphite) | 1.1 | 1.8 | 2.8 | 3.9 | 5.1 |

ΔYI Values

| Compound A (0.35% loading + 0.05% phosphite) | 1.2 | 1.7 | 1.9 | 3.0 | 3.9 |
| --- | --- | --- | --- | --- | --- |
| UV-1164 (0.35% loading + 0.05% phosphite) | 1.7 | 2.5 | 3.1 | 5.2 | 7.1 |
| Compound A (0.1% loading + 0.05% phosphite) | 1.4 | 2.1 | 3.1 | 4.5 | 6 |
| UV-1164 (0.1% loading + 0.05% phosphite) | 1.8 | 3.1 | 5.1 | 7.2 | 9.5 |

The results in Table 7, demonstrate that the stability of polycarbonate plaques containing 0.35% of Compound A is similar to polycarbonate plaques containing 0.35% UV-1164, as measured by YI values, when the plaques are subjected to oven aging at 130° C. Similarly, Table 8 demonstrates that the stability of polycarbonate plaques containing 0.35% or 0.1% of Compound A was considerably superior to the stability of polycarbonate plaques containing 0.35% or 0.1% of UV-1164, as measured by YI, ΔE, and ΔYI values, when the plaques are subjected to oven aging at 130° C.

Table 9 shows the effect of QUV accelerated weathering on YI, ΔE, and ΔYI values in polycarbonate plaques including 0.35, 0.2% and 0.1 by weight of Compound A or UV-1164.

TABLE 9

QUV (UVB-313) Accelerated Weathering of a Polycarbonate Plaque Stabilized with Compound A or UV-1164, Effect on YI, and ΔE.

| Additive | Exposure (hours) | | | | | | |
| --- | --- | --- | --- | --- | --- | --- | --- |
| | 0 | 20 | 40 | 60 | 80 | 100 | 120 |

YI Values

| Compound A (0.35% loading + 0.05% phosphite) | 8.7 | 10.1 | 11.5 | 13.4 | 14.9 | 16.5 | 18.3 |
| --- | --- | --- | --- | --- | --- | --- | --- |

TABLE 9-continued

QUV (UVB-313) Accelerated Weathering of a Polycarbonate Plaque
Stabilized with Compound A or UV-1164, Effect on YI, and ΔE.

| Additive | Exposure (hours) | | | | | | |
|---|---|---|---|---|---|---|---|
| | 0 | 20 | 40 | 60 | 80 | 100 | 120 |
| UV-1164 (0.35% loading + 0.05% phosphite) | 11.1 | 12.3 | 13.7 | 15.2 | 17 | 19.3 | 20.9 |
| ΔE Values | | | | | | | |
| Compound A (0.35% loading + 0.05% phosphite) | | 0.8 | 1.7 | 2.8 | 3.7 | 4.7 | |
| UV-1164 (0.35% loading + 0.05% phosphite) | | 0.8 | 1.6 | 2.5 | 3.6 | 4.9 | |

The results in Table 9 demonstrates that the stability of polycarbonate plaques containing 0.35% of Compound A was superior to or similar to the stability of polycarbonate plaques containing 0.35% of UV-1164, as measured by YI and ΔE values, when the plaques are subjected to QUV accelerated weathering.

Table 10 shows the effect of xenon-arc accelerated weathering on YI values in polycarbonate plaques including 0.35%, 0.2%, and 0.1% by weight of Compound A or UV-1164. Table 11 shows the effect of xenon-arc accelerated weathering on YI, ΔE, and ΔYI values in polycarbonate plaques including 0.2% and 0.1% by weight of Compound A or UV-1164

TABLE 10

Xenon-arc Accelerated Weathering of a Polycarbonate Plaque Stabilized
with Compound A or UV-1164, Effect on YI.

| Additive | Exposure (hours) | | |
|---|---|---|---|
| | 0 | 400 | 800 |
| Compound A (0.35% loading + 0.05% phosphite) | 8.5 | 9 | 12.6 |
| UV-1164 (0.35% loading + 0.05% phosphite) | 14.5 | 10.2 | 14.2 |
| Compound A (0.2% loading + 0.05% phosphite) | 7.3 | 8.9 | 14.7 |
| UV-1164 (0.2% loading + 0.05% phosphite) | 14.6 | 12.6 | 20.3 |
| Compound A (0.1% loading + 0.05% phosphite) | 6.3 | 8.8 | 15.2 |
| UV-1164 (0.1% loading + 0.05% phosphite) | 12.1 | 11.6 | 20.1 |

TABLE 11

Xenon-arc Accelerated Weathering of a Polycarbonate Plaque Stabilized
with Compound A or UV-1164, Effect on ΔE, and ΔYI.

| Additive | Exposure (hours) | |
|---|---|---|
| | 400 | 800 |
| ΔE Values | | |
| Compound A (0.2% loading + 0.05% phosphite) | 1 | 4.3 |
| UV-1164 (0.2% loading + 0.05% phosphite) | 1 | 3.3 |
| Compound A (0.1% loading + 0.05% phosphite) | 1.5 | 5.2 |

TABLE 11-continued

Xenon-arc Accelerated Weathering of a Polycarbonate Plaque Stabilized
with Compound A or UV-1164, Effect on ΔE, and ΔYI.

| Additive | Exposure (hours) | |
|---|---|---|
| | 400 | 800 |
| UV-1164 (0.1% loading + 0.05% phosphite) | 0.3 | 4.6 |
| ΔYI Values | | |
| Compound A (0.2% loading + 0.05% phosphite) | 1.6 | 7.4 |
| UV-1164 (0.2% loading + 0.05% phosphite) | −2 | 5.7 |
| Compound A (0.1% loading + 0.05% phosphite) | 2.5 | 8.9 |
| UV-1164 (0.1% loading + 0.05% phosphite) | −0.5 | 8 |

The results in Tables 10 and 11 demonstrates that the stability of polycarbonate plaques containing 0.35%, 0.2%, or 0.1% of Compound A was superior to or similar to the stability of polycarbonate plaques containing 0.35%, 0.2%, or 0.1% of UV-164, as measured by YI, ΔE, and ΔYI values, when the plaques are subjected to xenon-arc accelerated weathering.

Table 12 shows the effect on YI values of exposing the polycarbonate pellets to severe conditions during the injection molding process used to manufacture the plaques. As noted above, plaques are typically processed with the nozzle side at 300° C. Under the severe conditions the plaques are processed at a temperature of 340° C. with the compound filling the length of the injection molder barrel for either 40 seconds (severe 40 seconds) or for 5 minutes (severe 5 minutes).

TABLE 12

Effect of severe injection molding conditions on YI values.

| Additive | Normal | Severe (40 seconds) | Severe (5 minutes) |
|---|---|---|---|
| Compound A (0.35% loading + 0.05% phosphite) | 6.4 | 6.9 | 8.2 |
| UV-1164 (0.35% loading + 0.05% phosphite) | 8.9 | 19.5 | 40 |

The results in Table 12 demonstrates that the stability of polycarbonate plaques containing 0.35% of Compound A was distinctly superior to the stability of polycarbonate plaques containing 0.35% of UV-1164, as measured by YI values, when the plaques are subjected to severe processing conditions.

Example 14

Comparison of the Performance of 2-(2-hydroxy-4-octyloxyphenyl)-4,6-bis(3,4-dimethylphenyl-1,3,5-triazine (Compound A) Against 2-(2-hydroxy-4-hexyloxyphenyl)-4,6-diphenyl-1,3,5-triazine (Tinuvin-1577) in Polycarbonate Plagues Polycarbonate sample plaques were prepared as described in Example 13 containing 0.35%, 0.2%, or 0.1% by weight of Compound A or Tinuvin-1577 (commercially available from Ciba Specialty Chemicals, Inc. of Hawthorne, N.Y.). The sample plaques were tested for hydrolytic stability and subjected to xenon-arc accelerated weathering, QUV accelerated weathering, and oven aging at 130° C. according to the procedures described in Example 13. The results of hydrolytic testing are provided in Table 13.

TABLE 13

Hydrolytic Stability, Effect on Melt Flow Index.

| | Melt Flow Index (MFI) (g/10 min) | | |
|---|---|---|---|
| Additive | Before | After | ΔMFI |
| Compound A (0.35% loading + 0.1% phosphite) | 6.1 | 6.8 | 0.7 |
| Tinuvin 1577 (0.35% loading + 0.1% phosphite) | 7.1 | 9.5 | 2.4 |

The results in Table 13 show that Compound A had no significant effect on the hydrolytic stability of the polycarbonate plaques. Plaques containing Tinuvin-1577, however, appeared to show a definite increase in the melt flow index after being subjected to high temperature and pressure.

Table 14 shows a comparison of the effect of oven aging on YT values in polycarbonate plaques including 0.1% by weight of Compound A or 0.35% by weight of Tinuvin-1577.

TABLE 14

Oven Aging at 130° C. of a Polycarbonate Plaque Stabilized with Compound A (0.1% loading) or Tinuvin-1577 (0.35% loading), Effect on YI.

| | Exposure (hours) | | | | | |
|---|---|---|---|---|---|---|
| Additive | 0 | 50 | 100 | 150 | 200 | 250 |
| Compound A (0.1% loading + 0.05% phosphite) | 6.7 | 8.1 | 8.8 | 9.8 | 11.2 | 12.7 |
| Tinuvin 1577 (0.35% loading + 0.05% phosphite) | 9.9 | 11.3 | 12.2 | 12.9 | 14.4 | 15.8 |

The results in Table 14 demonstrates that the stability of polycarbonate plaques containing 0.1% of Compound A was consistently superior to the stability of polycarbonate plaques containing 0.35% of Tinuvin-1577, as measured by YI values, when the plaques are subjected to oven aging at 130° C. The results demonstrate that Compound A is equally effective at stabilizing the polycarbonate plaque when Compound A is present in a much lower loading than Tinuvin-1577.

Table 15 shows a comparison of the effect of QUV accelerated weathering on YI values in polycarbonate plaques including 0.35% by weight of Compound A or Tinuvin-1577.

TABLE 15

QUV (UVB-313) Accelerated Weathering of a Polycarbonate Plaque Stabilized with Compound A or Tinuvin-1577, Effect on YI.
YI Values

| | Exposure (hours) | | | | | | |
|---|---|---|---|---|---|---|---|
| Additive | 0 | 20 | 40 | 60 | 80 | 100 | 120 |
| Compound A (0.35% loading + 0.05% phosphite) | 8.7 | 10.1 | 11.5 | 13.4 | 14.9 | 16.5 | 18.3 |
| Tinuvin 1577 (0.35% loading + 0.05% phosphite) | 9.8 | 11.1 | 12.5 | 14.2 | 15.8 | 18 | 20.1 |

The results in Table 15 demonstrates that the stability of polycarbonate plaques containing 0.35% of Compound A was superior to the stability of polycarbonate plaques containing 0.35% of Tinuvin-1577, as measured by YI values, when the plaques are subjected to QUV accelerated weathering.

Table 16 shows the effect of severe conditions during the injection molding process used to manufacture the plaques on YI values. Severe conditions are defined as in Example 12.

TABLE 16

Effect of severe injection molding conditions on YI values.

| Additive | Normal | Severe (40 seconds) | Severe (5 minutes) |
|---|---|---|---|
| Compound A (0.35% loading + 0.1% phosphite) | 6.4 | 6.9 | 8.2 |
| Tinuvin 1577 (0.35% loading + 0.1% phosphite) | 8.3 | 7.6 | 8.5 |

The results in Table 16 demonstrates that the stability of polycarbonate plaques containing 0.35% of Compound A was significantly better than the stability of polycarbonate plaques containing 0.35% of Tinuvin-1577, as measured by YI values, when the plaques are subjected to severe processing conditions.

Table 17 shows the effect of oven aging at 130° C. on YI values in polycarbonate plaques including 0.35, 0.2%, and 0.1% by weight of Compound A or Tinuvin-1577.

TABLE 17

Oven Aging at 130° C. of a Polycarbonate Plaque Stabilized with Compound A or Tinuvin-1577, Effect on YI.
YI Values

| | Exposure (hours) | | | | | |
|---|---|---|---|---|---|---|
| Additive | 0 | 50 | 100 | 150 | 200 | 250 |
| Compound A (0.35% loading + 0.05% phosphite) | 8.5 | 9.7 | 10.2 | 10.4 | 11.5 | 12.4 |
| Tinuvin 1577 (0.35% loading + 0.05% phosphite) | 9.9 | 11.3 | 12.2 | 12.9 | 14.4 | 15.8 |
| Compound A (0.2% loading + 0.05% phosphite) | 7.3 | 8.7 | 9.4 | 10.5 | 11.7 | 13.1 |
| Tinuvin 1577 (0.2% loading + 0.05% phosphite) | 8.4 | 11 | 13 | 15.8 | 19.1 | 22.5 |
| Compound A (0.1% loading + 0.05% phosphite) | 6.7 | 8.1 | 8.8 | 9.8 | 11.2 | 12.7 |
| Tinuvin 1577 (0.1% loading + 0.05% phosphite) | 7.7 | 9.7 | 10.7 | 12 | 13.3 | 14.9 |

The results in Tables 17 demonstrates that the stability of polycarbonate plaques containing 0.35%, 0.2%, or 0.1% of Compound A was significantly better than the stability of polycarbonate plaques containing 0.35%, 0.2%, or 0.1% of Tinuvin-1577, as measured by YI values, when the plaques are subjected to oven aging at 130° C.

Table 18 shows the effect of xenon-arc accelerated weathering on YI values in polycarbonate plaques including 0.35, 0.2% and 0.1% by weight of Compound A or Tinuvin-1577.

TABLE 18

Xenon-arc Accelerated Weathering of a Polycarbonate Plaque Stabilized with Compound A or Tinuvin-1577, Effect on YI.

| Additive | Exposure (hours) | | |
|---|---|---|---|
|  | 0 | 400 | 800 |
| Compound A (0.35% loading + 0.05% phosphite) | 8.5 | 9 | 12.6 |
| Tinuvin 1577 (0.35% loading + 0.05% phosphite) | 9.6 | 10.2 | 13.5 |

The results in Tables 18 demonstrates that the stability of polycarbonate plaques containing 0.35% of Compound A was superior to the stability of polycarbonate plaques containing 0.35% of Tinuvin-1577, as measured by YI values, when the plaques are subjected to xenon-arc accelerated weathering.

Overall the results show that Compound A is effective at stabilizing polymeric compounds, such as polycarbonate, against discoloration. Moreover, the results demonstrate that Compound A is superior to conventional triazine light stabilizers such as UV-1164 and Tinuvin-1577.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A compound of formula II

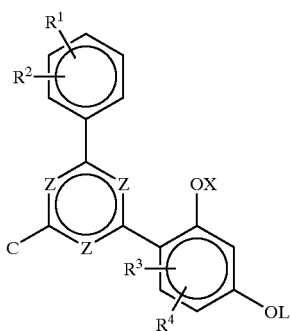

(II)

wherein each Z is nitrogen;

X is hydrogen or a blocking group selected from —$COR^a$, —$SO_2R^b$, $SiR^cR^dR^e$, —$PR^fR^g$, —$POR^fR^g$, and —$CONHR^h$, wherein $R^a$ is a $C_1$–$C_8$ alkyl, halogen-substituted $C_1$–$C_8$ alkyl, $C_5$–$C_{12}$ cycloalkyl, $C_2$–$C_8$ alkenyl, —$CH_2$—CO—$CH_3$, $C_1$–$C_{12}$ alkoxy, and phenyl or phenoxy which is unsubstituted or substituted by $C_1$–$C_{12}$ alkyl, $C_1$–$C_4$ alkoxy, halogen or benzyl;

$R^b$ is a $C_1$–$C_{12}$ alkyl, $C_6$–$C_{10}$ aryl and $C_7$–$C_{18}$ alkylaryl;

$R^c$, $R^d$, and $R^e$ is independently selected from $C_1$–$C_8$ alkyl, cyclohexyl, phenyl or C—$C_8$ alkoxy, $R^f$, and $R^g$ is independently selected from $C_1$–$C_{12}$ alkoxy, $C_1$–$C_{12}$ alkyl, $C_5$–$C_{12}$ cycloalkyl, and phenyl or phenoxy which is unsubstituted or substituted by $C_1$–$C_{12}$ alkyl, $C_1$–$C_4$ alkoxy, halogen or benzyl; and $R^h$ is a $C_1$–$C_8$ alkyl, $C_5$–$C_{12}$ cycloalkyl, $C_2$–$C_8$ alkenyl, —$CH_2$—CO—$CH_3$, or phenyl which is unsubstituted or substituted by $C_1$–$C_{12}$ alkyl, $C_2$–$C_8$ alkenyl, $C_1$–$C_4$ alkoxy, halogen or benzyl;

C is either

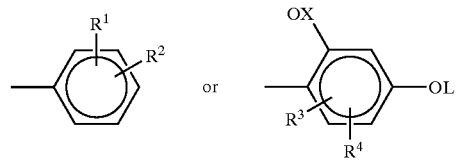

L is a straight alkyl, branched alkyl or cycloalkyl of between 1 and 20 carbons optionally interrupted by one or more oxygen atoms, having one or more of the hydrogens in the alkyl chain substituted for by a hydroxyl group, or terminating with a carbonyl functionality of general structure —CO—M, wherein M is a $OR^x$, $NR^xR^y$ wherein $R^x$ and $R^y$ are independently hydrogen or an alkyl group of between 1 and 8 carbons that optionally have one or more of the hydrogens substituted for by a hydroxyl group;

each of $R^3$ and $R^4$ are independently a hydrogen, hydrocarbyl, halogen, hydroxyl, cyano, —O(hydrocarbyl), —O(functional hydrocarbyl), —N(hydrocarbyl)(hydrocarbyl), —N(hydrocarbyl)(functional hydrocarbyl), —N(functional hydrocarbyl)(functional hydrocarbyl), —S(hydrocarbyl), —S(functional hydrocarbyl), —$SO_2$(hydrocarbyl), —$SO_3$(hydrocarbyl), —$SO_2$(functional hydrocarbyl), —$SO_3$(functional hydrocarbyl), —COO(hydrocarbyl), COO(functional hydrocarbyl), —CO(hydrocarbyl), —CO(functional hydrocarbyl), —OCO(hydrocarbyl), —OCO(functional hydrocarbyl), —$CONH_2$, —CONH(hydrocarbyl), —CONH(functional hydrocarbyl), —CON(hydrocarbyl)(hydrocarbyl), —CON(functional hydrocarbyl)(hydrocarbyl), —CON(functional hydrocarbyl)(functional hydrocarbyl), or a hydrocarbyl group substituted by any of the above groups; and each $R^1$ and $R^2$ is identical or different and is independently a hydrocarbyl group of between 1 and 20 carbons, wherein $R^1$ and $R^2$ are attached to an aromatic benzene ring so that they are ortho to each other.

2. The compound of claim 1, wherein $R^3$ and $R^4$ is independently selected from hydrogen, and an alkyl of 1 to 8 carbons wherein one or more of the hydrogens in the alkyl chain may optionally be substituted with the nitrogen of an amine.

3. The compound of claim 1, wherein each $R^1$ and $R^2$ is individually a $C_1$ to $C_{10}$ straight chain alkyl, branched alkyl, or cycloalkyl.

4. The compound of claim 3, wherein $R^1$ and $R^2$ are attached to the aromatic benzene ring at the 3 and 4 position relative to the point of attachment of the triazine ring.

5. The compound of claim 3, wherein $R^1$ and $R^2$ are attached to the aromatic benzene ring at the 2 and 3 position relative to the point of attachment of the triazine ring.

6. The compound of claim 4, wherein C is

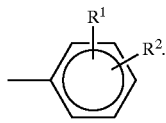

7. The compound of claim 6, wherein each $R^1$ and $R^2$ are methyl groups.

8. A compound of formula (III):

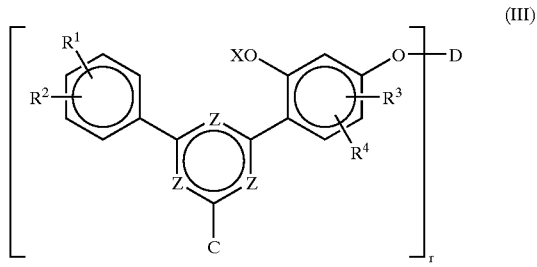

wherein each Z is nitrogen;

X is hydrogen or a blocking group selected from —$COR^a$, —$SO_2R^b$, —$SiR^cR^dR^e$, —$PR^fR^g$, —$POR^fR^g$, and —$CONHR^h$, wherein $R^a$ is $C_1$–$C_8$ alkyl, halogen-substituted $C_1$–$C_8$ alkyl, $C_5$–$C_{12}$ cycloalkyl, $C_2$–$C_8$ alkenyl, —$CH_2$—CO—$CH_3$, $C_1$–$C_{12}$ alkoxy, and phenyl or phenoxy which is unsubstituted or substituted by $C_1$–$C_{12}$ alkyl, $C_1$–$C_4$ alkoxy, halogen or benzyl;

$R^b$ is $C_1$–$C_{12}$ alkyl, $C_6$–$C_{10}$ aryl and $C_7$–$C_{18}$ alkylaryl;

$R^c$, $R^d$, and $R^e$ is independently selected from $C_1$–$C_8$ alkyl, cyclohexyl, phenyl or $C_1$–$C_8$ alkoxy, $R^f$, and $R^g$ is independently selected from $C_1$–$C_{12}$ alkoxy, $C_1$–$C_{12}$ alkyl, $C_5$–$C_{12}$ cycloalkyl, and phenyl or phenoxy which is unsubstituted or substituted by $C_1$–$C_{12}$ alkyl, $C_1$–$C_4$ alkoxy, halogen or benzyl; and $R^h$ is a $C_1$–$C_8$ alkyl, $C_5$–$C_{12}$ cycloalkyl, $C_2$–$C_8$ alkenyl, —$CH_2$—CO—$CH_3$, or phenyl which is unsubstituted or substituted by $C_1$–$C_{12}$ alkyl, $C_2$–$C_8$ alkenyl, $C_1$–$C_4$ alkoxy, halogen or benzyl;

C is either

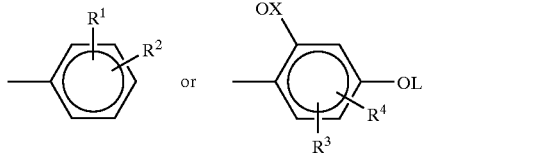

r is an integer between 2 and 4;

each of L is independently a
hydrogen, hydrocarbyl, —$SO_2$(hydrocarbyl), —$SO_3$(hydrocarbyl), —$SO_2$(functional hydrocarbyl), —$SO_3$(functional hydrocarbyl), —COO(hydrocarbyl), —COO(functional hydrocarbyl), —CO(hydrocarbyl), —CO(functional hydrocarbyl), —OCO(hydrocarbyl), —OCO(functional hydrocarbyl), —$CONH_2$, —CONH(hydrocarbyl), —CONH(functional hydrocarbyl), —CON (hydrocarbyl)(hydrocarbyl), —CON (functional hydrocarbyl)(hydrocarbyl), —CON (functional hydrocarbyl)(functional hydrocarbyl), or a hydrocarbyl group substituted by any of the above groups;

each of $R^3$ and $R^4$ are independently a
hydrogen, hydrocarbyl, halogen, hydroxyl, cyano, O(hydrocarbyl), —O(functional hydrocarbyl), —N(hydrocarbyl)(hydrocarbyl), —N(hydrocarbyl)(functional hydrocarbyl), N(functional hydrocarbyl)(functional hydrocarbyl), —S(hydrocarbyl), —S(functional hydrocarbyl), —$SO_2$(hydrocarbyl), —$SO_3$(hydrocarbyl), —$SO_2$(functional hydrocarbyl), —$SO_3$(functional hydrocarbyl), —COO(hydrocarbyl), —COO(functional hydrocarbyl), —CO(hydrocarbyl), —CO(functional hydrocarbyl), —OCO(hydrocarbyl), —OCO(functional hydrocarbyl), —$CONH_2$, —CONH(hydrocarbyl), —CONH(functional hydrocarbyl), —CON (hydrocarbyl)(hydrocarbyl), —CON (functional hydrocarbyl)(hydrocarbyl), —CON (functional hydrocarbyl)(functional hydrocarbyl), or a hydrocarbyl group substituted by any of the above groups;

each $R^1$ and $R^2$ is identical or different and is independently a hydrocarbyl group of between 1 and 20 carbons, wherein $R^1$ and $R^2$ are attached to an aromatic benzene ring so that they are ortho to each other;

D, when r is 2, is selected from the group consisting of $C_1$–$C_{16}$ alkylene, $C_4$–$C_{12}$ alkenylene, xylylene, $C_4$–$C_{20}$ alkylene which is interrupted by one or more oxygen atoms, hydroxy-substituted $C_3$ $C_{20}$ alkyl which is interrupted by one or more oxygen atoms, —$CH_2CH(OH)CH_2O$—$R^{15}CH_2CH(OH)CH_2$—, —CO—$R^{16}$—CO—, —O—NH—$R^{17}$—NH—C—, —$(CH_2)_s$—COO—$R^{18}$—OCO—$(CH_2)_s$— a polyoxyalkylene bridge member of the formula XX

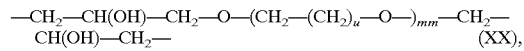

a polyoxyalkylene bridge member of the formula XXI

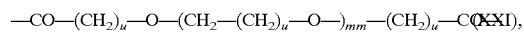

a polyoxyalkylene bridge member of the formula XXII

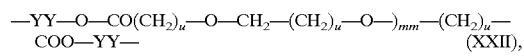

a polyoxyalkylene bridge member of the formula XXIII

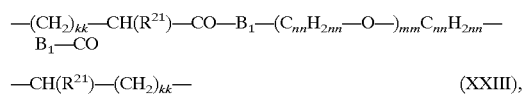

a polyoxyalkylene bridge member of the formula XXIV

a polyoxyalkylene bridge member of the formula XXV

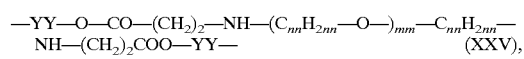

a polyoxyalkylene bridge member of the formula XXVI

and a polyoxyalkylene bridge member of the formula XXVII

—CH(CH₃)—CH₂—(O—CH(CH₃)—CH₂)ₐ—(O CH₂—CH₂)ᵦ—(O—CH₂—CH(CH₃))ᵧ— (XXVII), wherein a+c=2.5 and b=8.5 to 40.5 or a+c=2 to 33 and b=0, $R^{15}$ is $C_2$–$C_{10}$ alkylene, $C_2$–$C_{10}$ oxaalkylene or $C_2$–$C_{10}$ dithiaalkylene, phenylene, naphthylene, diphenylene, or $C_2$–$C_6$ alkenylene, or phenylene-XX-phenylene wherein XX is —O—, —S—, —SO₂—, —CH₂—, or —C(CH₃)₂—;

$R^{16}$ is $C_2$–$C_{10}$ alkylene, $C_2$–$C_{10}$ oxaalkylene or $C_2$–$C_{10}$ dithiaalkylene, phenylene, naphthylene, diphenylene, or $C_2$–$C_6$ alkenylene provided that when r is 3 the alkenylene has at least 3 carbons;

$R^{17}$ is $C_2$–$C_{10}$ alkylene, phenylene, naphthylene, diphenylene, or $C_2$–$C_6$ alkenylene, methylenediphenylene, or $C_4$–$C_{15}$ alkylphenylene; and $R^{18}$ is $C_2$–$C_{10}$ alkylene, or $C_4$–$C_{20}$ alkylene interrupted by one or more oxygen atoms;

$R^{21}$ is hydrogen or $C_1$–$C_{16}$ alkyl;

YY is unsubstituted or substituted $C_2$–$C_{20}$ alkyl;

B, is NH or O;

kk is zero or an integer from 1–16;

mm is an integer from 2 to 60;

nn is an integer from 2 to 6;

s is 1–6;

u is an integer from 1 to 4;

when r is 3, D is

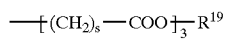

and when r is 4, D is

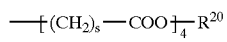

wherein $R^{19}$ is $C_3$–$C_{10}$ alkanetriyl and $R^{20}$ is $C_4$–$C_{10}$ alkanetetryl.

9. The compound of claim 8, wherein r is 2 and D is an alkyl chain of between 1 and 10 carbons or —CO—P—CO—, wherein P is an alkyl chain of between 1 and 10 carbons or a benzene ring wherein the carbonyl groups are metal or para to each other.

10. The compound of claim 9, wherein $R^3$ and $R^4$ is independently selected from hydrogen, and an alkyl of 1 to 8 carbons wherein one or more of the hydrogens in the alkyl chain may optionally be substituted with the nitrogen of an amine.

11. The compound of claim 9, wherein $R^1$ and $R^2$ is individually a $C_1$ to $C_{10}$ straight chain alkyl, branched alkyl, or cycloalkyl.

12. The compound of claim 11, wherein $R^1$ and $R^2$ are attached to the aromatic benzene ring at the 3 and 4 position relative to the point of attachment of the triazine ring.

13. The compound of claim 11, wherein $R^1$ and $R^2$ are attached to the aromatic benzene ring at the 2 and 3 position relative to the point of attachment of the triazine ring.

14. The compound of claim 9, wherein C is

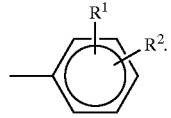

15. The compound of claim 14, wherein each $R^1$ and $R^2$ are methyl groups.

16. The compound of claim 13, wherein X is hydrogen; C is

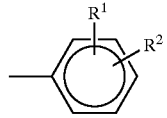

each $R_1$ and $R_2$ is individually a $C_1$ to $C_{10}$ straight chain alkyl, branched alkyl, or cycloalkyl; and $R^3$ and $R^4$ are each hydrogen.

17. A compound of formula (IV):

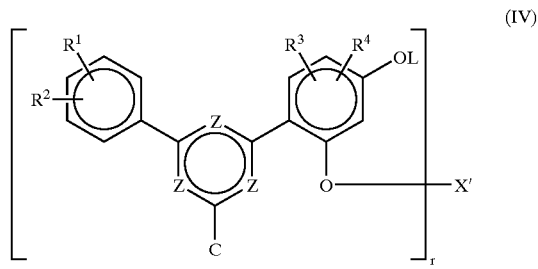

wherein each Z is nitrogen;

C is either

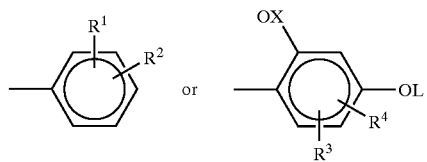

wherein X is hydrogen or a blocking group selected from —COR$^a$, —SO₂R$^b$, —SiR$^c$R$^d$R$^e$, —PR$^f$R$^g$, —POR$^f$R$^g$, and —CONHR$^h$, wherein R$^a$ is a $C_1$–$C_8$ alkyl, halogen-substituted $C_1$–$C_8$ alkyl, $C_5$–$C_{12}$ cycloalkyl, $C_2$–$C_8$ alkenyl, —CH₂—CO—CH₃, $C_1$–$C_{12}$ alkoxy, and phenyl or phenoxy which is unsubstituted or substituted by $C_1$–$C_{12}$ alkyl, $C_1$–$C_4$ alkoxy, halogen or benzyl;

R$^b$ is a $C_1$–$C_{12}$ alkyl, $C_6$–$C_{10}$ aryl and $C_7$–$C_8$ alkylaryl;

R$^c$, R$^d$, and R$^e$ is independently selected from $C_1$–$C_8$ alkyl, cyclohexyl, phenyl or $C_1$–$C_8$ alkoxy, R$^f$, and R$^g$ is independently selected from $C_1$–$C_{12}$ alkoxy, $C_1$–$C_{12}$ alkyl, $C_5$–$C_{12}$ cycloalkyl, and phenyl or phenoxy which is unsubstituted or substituted by $C_1$–$C_{12}$ alkyl, $C_1$–$C_4$ alkoxy, halogen or benzyl; and R$^h$ is a $C_1$–$C_8$ alkyl, $C_5$–$C_{12}$ cycloalkyl, $C_2$–$C_8$ alkenyl, —CH₂—CO—CH₃, or phenyl which is unsubstituted or substituted by $C_1$–$C_{12}$ alkyl, $C_2$–$C_8$ alkenyl, $C_1$–$C_4$ alkoxy, halogen or benzyl;

r is an integer between 2 and 4;

each of L is independently a hydrogen, hydrocarbyl, —SO₂(hydrocarbyl), —SO₃(hydrocarbyl), —SO₂(functional hydrocarbyl), —SO₃(functional hydrocarbyl), —COO(hydrocarbyl), —COO(functional hydrocarbyl), —CO(hydrocarbyl), —CO(functional hydrocarbyl), —OCO(hydrocarbyl), —OCO(functional hydrocarbyl), —CONH₂, —CONH(hydrocarbyl), —CONH(functional hydrocarbyl), —CON (hydrocarbyl)(hydrocarbyl), —CON (functional hydrocarbyl)(hydrocarbyl), —CON (functional hydrocarbyl)(functional hydrocarbyl), or a hydrocarbyl group substituted by any of the above groups;

each of $R^3$ and $R^4$ are independently a hydrogen, hydrocarbyl, halogen, hydroxyl, cyano, —O(hydrocarbyl), —O(functional hydrocarbyl), —N(hydrocarbyl)(hydrocarbyl), —N(hydrocarbyl) (functional hydrocarbyl), —N(functional hydrocarbyl) (functional hydrocarbyl), —S(hydrocarbyl), —S(functional hydrocarbyl), —SO$_2$(hydrocarbyl), —SO$_3$(hydrocarbyl), —SO$_2$(functional hydrocarbyl), —SO$_3$(functional hydrocarbyl), —COO(hydrocarbyl), —COO(functional hydrocarbyl), —CO(hydrocarbyl), —CO(functional hydrocarbyl), —OCO(hydrocarbyl), —OCO(functional hydrocarbyl), —CONH$_2$, —CONH(hydrocarbyl), —CONH(functional hydrocarbyl), —CON(hydrocarbyl)(hydrocarbyl), —CON(functional hydrocarbyl)(hydrocarbyl), —CON(functional hydrocarbyl)(functional hydrocarbyl), or a hydrocarbyl group substituted by any of the above groups;

each $R^1$ and $R^2$ is identical or different and is independently a hydrocarbyl group of between 1 and 20 carbons, wherein $R^1$ and $R^2$ are attached to an aromatic benzene ring so that they are ortho to each other;

X' when r is 2, is selected from the group consisting of $C_1$–$C_{16}$ alkylene, $C_4$–$C_{12}$ alkenylene, xylylene, $C_4$–$C_{20}$ alkylene which is interrupted by one or more oxygen atoms, hydroxy-substituted $C_3$ $C_{20}$ alkyl which is interrupted by one or more oxygen atoms, —CH$_2$CH(OH)CH$_2$—R$^{15}$—OCH$_2$CH(OH)CH$_2$—, —COR$^{16}$—CO—, O—NH—R$^{17}$—NH—C—, —CH$_2$), —COO—R$^{18}$—OCO—(CH$_2$)$_s$— a polyoxyalkylene bridge member of the formula XX

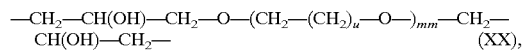

—CH$_2$—CH(OH)—CH$_2$—O—(CH$_2$—(CH$_2$)$_u$—O—)$_{mm}$—CH$_2$—CH(OH)—CH$_2$— (XX), a polyoxyalkylene bridge member of the formula XXI —CO—(CH$_2$)$_u$—O—(CH$_2$—(CH$_2$)$_u$—O—)$_{mm}$—(CH$_2$)$_u$—CO— (XXI), a polyoxyalkylene bridge member of the formula XXII —YY—O—CO(CH$_2$)$_u$—O—(CH$_2$—(CH$_2$)$_u$—O—)$_{mm}$—(CH$_2$)$_u$—COO—YY— (XXII), a polyoxyalkylene bridge member of the formula XXIII —(CH$_2$)$_{kk}$—CH(R$^{21}$)—CO—B$_1$—(C$_{nn}$H$_{2nn}$—O—)$_{mm}$C$_{nn}$H$_{2nn}$—B$_1$—CO—CH(R$^{21}$)—

(CH$_2$)$_{kk}$— (XXIII), a polyoxyalkylene bridge member of the formula XXIV

—COCH(R$^{21}$)CH$_2$NH(C$_{nn}$H$_{2nn}$O)$_{mm}$C$_{nn}$H$_{2nn}$—NHCH$_2$—CH(R$^{21}$)CO— (XXIV), a polyoxyalkylene bridge member of the formula XXV (CH$_2$)$_2$COO—YY— (XXV), a polyoxyalkylene bridge member of the formula XXVI —(C$_{nn}$H$_{2nn}$—O—)$_{mm}$—C$_{nn}$H$_{2nn}$— (XXVI), and a polyoxyalkylene bridge member of the formula XXVII —CH(CH$_3$)—CH$_2$—O—CH(CH$_3$)—CH$_2$)$_a$—
(O—CH$_2$—CH$_2$)$_b$—(O—CH$_2$—CH(CH$_3$)$_c$— (XXVII), wherein a+c=2.5 and b=8.5 to 40.5 or a+c=2 to 33 and b=0, $R^{15}$ is $C_2$–$C_{10}$ alkylene, $C_2$–$C_{10}$ oxaalkylene or $C_2$–$C_{10}$ dithiaalkylene, phenylene, naphthylene, diphenylene, or $C_2$–$C_6$ alkenylene, or phenylene-XX-phenylene wherein XX is —O—, —S—, —SO$_2$—, —CH$_2$—, or —C(CH$_3$)$_2$—;

$R^{16}$ is $C_2$–$C_{10}$ alkylene, $C_2$–$C_{10}$ oxaalkylene or $C_2$–$C_{10}$ dithiaalkylene, phenylene, naphthylene, diphenylene, or $C_2$–$C_6$ alkenylene provided that when r is 3 the alkenylene has at least 3 carbons;

$R^{17}$ is $C_2$–$C_{10}$ alkylene, phenylene, naphthylene, diphenylene, or $C_2$–$C_6$ alkenylene, methylenediphenylene, or $C_4$–$C_{15}$ alkylphenylene; and $R^{18}$ is $C_2$–$C_{10}$ alkylene, or $C_4$–$C_{20}$ alkylene interrupted by one or more oxygen atoms;

$R^{21}$ is hydrogen or $C_1$–$C_{16}$ alkyl;

YY is unsubstituted or substituted $C_2$–$C_{20}$ alkyl;

$B_1$ is NH or O;

kk is zero or an integer from 1–16;

mm is an integer from 2 to 60;

nn is an integer from 2 to 6;

s is 1–6;

u is an integer from 1 to 4;

when r is 3, X' is

—[(CH$_2$)$_s$—COO]$_3$—R$^{19}$ and when r is 4, X' is

—[(CH$_2$)$_s$—COO]$_4$—R$^{20}$ wherein $R^{19}$ is $C_3$ $C_{10}$ alkanetriyl and $R^{20}$ is $C_4$ $C_{10}$ alkanetetryl.

18. The compound of claim 17, wherein r is 2 and X' is an alkyl chain of between 1 and 10 carbons or —CO—P—CO—, wherein P is an alkyl chain of between 1 and 10 carbons or a benzene ring wherein the carbonyl groups are meta or para to each other.

19. The compound of claim 18, wherein $R^3$ and $R^4$ is independently selected from hydrogen, and an alkyl of 1 to 8 carbons wherein one or more of the hydrogens in the alkyl chain may optionally be substituted with the nitrogen of an amine.

20. The compound of claim 18, wherein L is alkyl chain of between 1 and 20 carbons, wherein the alkyl chain is optionally interrupted by one or more oxygen atoms, has one or more of the hydrogens in the alkyl chain substituted for by a hydroxyl group, or terminates with a carbonyl functionality of general structure —CO—M, wherein M is a OR$^x$ or NR$^x$R$^y$, wherein R$^x$ and R$^y$ are independently hydrogen or an alkyl group of between 1 and 8 carbons that optionally may have one or more of the hydrogens substituted for by a hydroxyl group.

21. The compound of claim 18, wherein $R^1$ and $R^2$ is individually a $C_1$ to $C_{10}$ straight chain alkyl, branched alkyl, or cycloalkyl.

22. The compound of claim 21, wherein $R^1$ and $R^2$ are attached to the aromatic benzene ring at the 3 and 4 position relative to the point of attachment of the triazine ring.

23. The compound of claim 21, wherein $R^1$ and $R^2$ are attached to the aromatic benzene ring at the 2 and 3 position relative to the point of attachment of the triazine ring.

24. The compound of claim 22, wherein C is

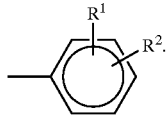

25. The compound of claim 24, wherein each $R^1$ and $R^2$ are methyl groups.

26. The compound of claim 18, wherein X is hydrogen; C is

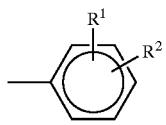

each $R_1$ and $R_2$ is individually a $C_1$ to $C_{10}$ straight chain alkyl, branched alkyl, or cycloalkyl; and $R^3$ and $R^4$ are each hydrogen.

27. A compound of formula (V):

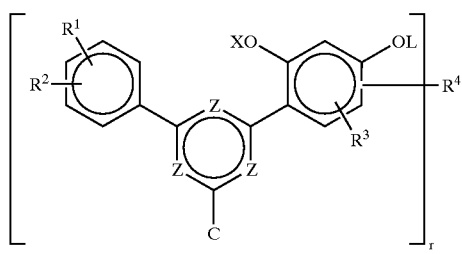

(V)

wherein each Z is nitrogen;

X is hydrogen or a blocking group selected from —COR$^a$, —SO$_2$R$^b$, —SiR$^c$R$^d$R$^e$, —PR$^f$R$^g$, —POR$^f$R$^g$, and —CONHR$^h$, wherein R$^a$ is a $C_1$–$C_8$ alkyl, halogen-substituted $C_1$–$C_8$ alkyl, $C_5$–$C_{12}$ cycloalkyl, $C_2$–$C_8$ alkenyl, —CH$_2$—CO—CH$_3$, $C_1$–$C_{12}$ alkoxy, and phenyl or phenoxy which is unsubstituted or substituted by $C_1$–$C_{12}$ alkyl, $C_1$–$C_4$ alkoxy, halogen or benzyl;

R$^b$ is a $C_1$–$C_{12}$ alkyl, $C_6$–$C_{10}$ aryl and $C_7$–$C_{18}$ alkylaryl;

R$^c$, R$^d$, and R$^e$ is independently selected from $C_1$–$C_8$ alkyl, cyclohexyl, phenyl or $C_1$–$C_8$ alkoxy, R$^f$, and R$^g$ is independently selected from $C_1$–$C_{12}$ alkoxy, $C_1$–$C_{12}$ alkyl, $C_5$–$C_{12}$ cycloalkyl, and phenyl or phenoxy which is unsubstituted or substituted by $C_1$–$C_{12}$ alkyl, $C_1$–$C_4$ alkoxy, halogen or benzyl; and R$^h$ is a $C_1$–$C_8$ alkyl, $C_5$–$C_{12}$ cycloalkyl, $C_1$–$C_8$ alkenyl, —CH$_2$—CO—CH$_3$, or phenyl which is unsubstituted or substituted by $C_1$–$C_{12}$ alkyl $C_2$–$C_8$ alkenyl, $C_1$–$C_4$ alkoxy, halogen or benzyl;

C is

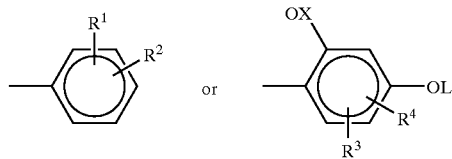

r is 2;

each of L is independently a
hydrogen, hydrocarbyl, —SO$_2$(hydrocarbyl), —SO$_3$(hydrocarbyl), —SO$_2$(functional hydrocarbyl), —SO$_3$(functional hydrocarbyl), —COO(hydrocarbyl), —COO(functional hydrocarbyl), —CO(hydrocarbyl), —CO(functional hydrocarbyl), —OCO(hydrocarbyl), OCO(functional hydrocarbyl), —CONH$_2$, —CONH(hydrocarbyl), —CONH(functional hydrocarbyl), —CON (hydrocarbyl)(hydrocarbyl), —CON (functional hydrocarbyl)(hydrocarbyl), —CON (functional hydrocarbyl)(functional hydrocarbyl), or a hydrocarbyl group substituted by any of the above groups;

each of $R^3$ is independently a
hydrogen, hydrocarbyl, halogen, hydroxyl, cyano, —O(hydrocarbyl), —O(functional hydrocarbyl), —N(hydrocarbyl)(hydrocarbyl), —N(hydrocarbyl)(functional hydrocarbyl), —N(functional hydrocarbyl)(functional hydrocarbyl), —S(hydrocarbyl), —S(functional hydrocarbyl), —SO$_2$(hydrocarbyl), —SO$_3$(hydrocarbyl), —SO$_2$(functional hydrocarbyl), —SO$_3$(functional hydrocarbyl), —COO(hydrocarbyl), —COO(functional hydrocarbyl), —CO(hydrocarbyl), —CO(functional hydrocarbyl), —OCO(hydrocarbyl), —OCO(functional hydrocarbyl), —CONH$_2$, —CONH(hydrocarbyl), —CONH(functional hydrocarbyl), —CON (hydrocarbyl)(hydrocarbyl), —CON (functional hydrocarbyl)(hydrocarbyl), —CON (functional hydrocarbyl)(functional hydrocarbyl), or a hydrocarbyl group substituted by any of the above groups;

each $R^1$ and $R^2$ is identical or different and is independently a hydrocarbyl group of between 1 and 20 carbons, wherein $R^1$ and $R^2$ are attached to an aromatic benzene ring so that they are ortho to each other; and $R^4$ is selected from the group consisting of straight chain alkyl of 1 to 12 carbon atoms, branched chain alkyl of 1 to 12 carbon atoms, cycloalkyl of 5 to 12 carbon atoms, alkyl substituted by cyclohexyl, alkyl interrupted by cyclohexyl, alkyl substituted by phenylene, alkyl interrupted by phenylene, benzylidene, —S—, —S—S—, —S—E—S—, —SO—, —SO$_2$—, —SO—E—SO—, —SO$_2$—E—SO$_2$—, —CH—NH—E—NH—CH$_2$—, and

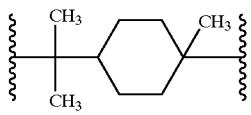

wherein E is selected from the group consisting of alkyl of 2 to 12 carbon atoms, cycloalkyl of 5 to 12 carbon atoms, alkyl interrupted by cyclohexyl of 8 to 12 carbon atoms, and alkyl terminated by cyclohexyl of 8 to 12 carbon atoms.

28. The compound of claim 27, wherein $R^4$ is —$CH_2$—.

29. The compound of claim 27, wherein $R^3$ is selected from hydrogen, and an alkyl of 1 to 8 carbons wherein one or more of the hydrogens in the alkyl chain may optionally be substituted with a nitrogen of an amine.

30. The compound of claim 27, wherein L is alkyl chain of between 1 and 20 carbons, wherein the alkyl chain is optionally interrupted by one or more oxygen atoms, has one or more of the hydrogens in the alkyl chain substituted for by a hydroxyl group, or terminates with a carbonyl functionality of general structure —CO—M, wherein M is a $OR^x$ or $NR^xR^y$, wherein $R^x$ and $R^y$ are independently hydrogen or an alkyl group of between 1 and 8 carbons that optionally may have one or more of the hydrogens substituted for by a hydroxyl group.

31. The compound of claim 27, wherein $R^1$ and $R^2$ is individually a $C_1$ to $C_{10}$ straight chain alkyl, branched alkyl, or cycloalkyl.

32. The compound of claim 31, wherein $R^1$ and $R^2$ are attached to the aromatic benzene ring at the 3 and 4 position relative to the point of attachment of the triazine ring.

33. The compound of claim 31, wherein $R^1$ and $R^2$ are attached to the aromatic benzene ring at the 2 and 3 position relative to the point of attachment of the triazine ring.

34. The compound of claim 28, wherein; X is hydrogen; C is

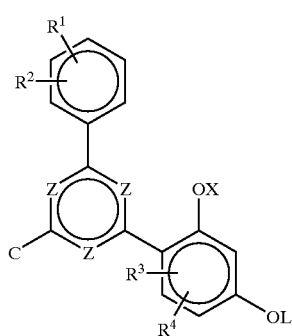

each $R_1$ and $R_2$ is individually a $C_1$ to $C_{10}$ straight chain alkyl, branched alkyl, or cycloalkyl; and $R^3$ is a hydrogen.

35. A polymeric article comprising at least one polymeric material and a sufficient amount of a stabilizing composition to inhibit at least one of photo or thermal degradation, wherein the stabilizer composition comprises one or more compounds of structure (II)–(V), wherein compound (II) has the structure:

(II)

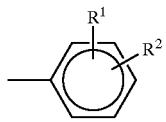

wherein each Z is nitrogen;

X is hydrogen or a blocking group selected from —$COR^a$, —$SO_2R^b$, —$SiR^cR^dR^e$, —$PR^fR^g$, —$POR^fR^g$, and —$CONHR^h$, wherein $R^a$ is a $C_1$–$C_8$ alkyl, halogen-substituted $C_1$–$C_8$ alkyl $C_5$–$C_{12}$ cycloalkyl, $C_2$–$C_8$ alkenyl, —$CH_2$—CO—$CH_3$, $C_1$–$C_{12}$ alkoxy, and phenyl or phenoxy which is unsubstituted or substituted by $C_1$–$C_{12}$ alkyl, $C_1$–$C_4$ alkoxy, halogen or benzyl;

$R^b$ is a $C_1$–$C_{12}$ alkyl, $C_6$–$C_{10}$ aryl and $C_7$–$C_{18}$ alkylaryl:

$R^c$, $R^d$, and $R^e$ is independently selected from $C_1$–$C_8$ alkyl, cyclohexyl, phenyl or $C_1$–$C_8$ alkoxy, $R^f$, and $R^g$ is independently selected from $C_1$–$C_{12}$ alkoxy, $C_1$–$C_{12}$ alkyl, $C_5$–$C_{12}$ cycloalkyl, and phenyl or phenoxy which is unsubstituted or substituted by $C_1$–$C_{12}$ alkyl, $C_1$–$C_4$ alkoxy, halogen or benzyl; and $R^h$ is a $C_1$–$C_8$ alkyl, $C_5$–$C_{12}$ cycloalkyl, $C_2$–$C_8$ alkenyl, —$CH_2$—CO—$CH_3$, or phenyl which is unsubstituted or substituted by $C_1$–$C_{12}$ alkyl, $C_2$–$C_8$ alkenyl, $C_1$–$C_4$ alkoxy, halogen or benzyl;

C is

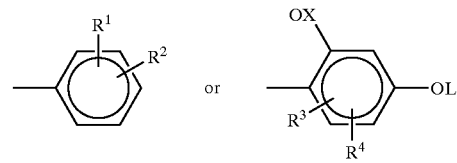

L is an alkyl chain of between 1 and 20 carbons, wherein the alkyl chain is optionally interrupted by one or more oxygen atoms, has one or more of hydrogens in the alkyl chain substituted for by a hydroxyl group, or terminates with a carbonyl functionality of general structure —CO—M, wherein M is a $OR^x$, $NR^xR^y$ and $R^x$ and $R^y$ are independently hydrogen or an alkyl group of between 1 and 8 carbons that optionally may have one or more of the hydrogens substituted for by a hydroxyl group;

$R^3$ and $R^4$ is independently selected from hydrogen, and an alkyl of 1 to 8 carbons wherein one or more of the hydrogens in the alkyl chain may optionally be substituted with a nitrogen of an amine; and each $R^1$ and $R^2$ is individually a $C_1$ to $C_{10}$ straight chain alkyl, branched alkyl, or cycloalkyl and $R^1$ and $R^2$ are attached to an aromatic benzene ring so that they are ortho to each other;

compound (III) has the structure:

(III)

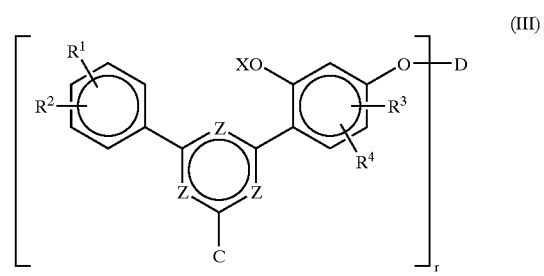

wherein each Z is nitrogen;

X is defied above;

C is

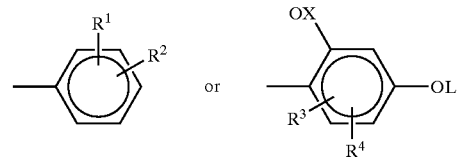

r is 2 and D is an alkyl chain of between 1 and 10 carbons or —CO—P—CO—, wherein P is an alkyl chain of between 1 and 10 carbons or a benzene ring wherein the carbonyl groups are meta or para to each other;

$R^3$ and $R^4$ is independently selected from hydrogen, and an alkyl of 1 to 8 carbons wherein one or more of the hydrogens in the alkyl chain may optionally be substituted with a nitrogen of an amine; and $R^1$ and $R^2$ is individually a $C_1$ to $C_{10}$ straight chain alkyl, branched alkyl, or cycloalkyl and $R^1$ and $R^2$ are attached to an aromatic benzene ring so that they are ortho to each other;

Compound (IV) has the structure:

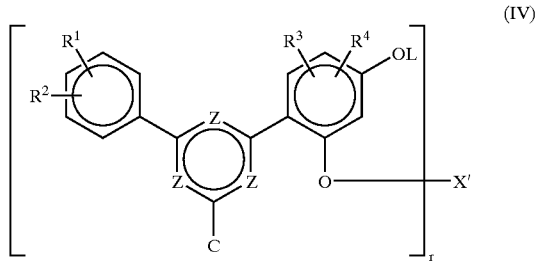

(IV)

wherein each Z is nitrogen;

C is

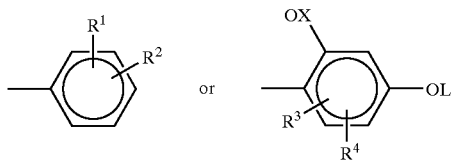

wherein r is 2 and X' is an alkyl chain of between 1 and 10 carbons or —CO—P—CO—, wherein P is an alkyl chain of between 1 and 10 carbons or a benzene ring wherein the carbonyl groups are meta or para to each other;

$R^3$ and $R^4$ is independently selected from hydrogen, and an alkyl of 1 to 8 carbons wherein one or more of the hydrogens in the alkyl chain may optionally be substituted with a nitrogen of an amine;

L is alkyl chain of between 1 and 20 carbons, wherein the alkyl chain is optionally interrupted by one or more oxygen atoms, has one or more of hydrogens in the alkyl chain substituted for by a hydroxyl group, or terminates with a carbonyl functionality of general structure —CO—M, wherein M is a $OR^x$, $NR^xR^y$ and $R^x$ and $R^y$ are independently hydrogen or an alkyl group of between 1 and 8 carbons that optionally may have one or more of the hydrogens substituted for by a hydroxyl group;

$R^1$ and $R^2$ is individually a $C_1$ to $C_{10}$ straight chain alkyl, branched alkyl, or cycloalkyl and $R^1$ and $R^2$ are attached to an aromatic benzene ring so that they are ortho to each other, and compound (V) has the structure:

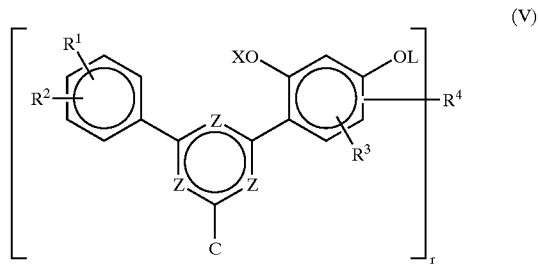

(V)

wherein each Z is nitrogen

X is defined above;

C is

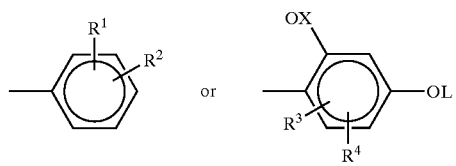

r is 2;

$R^4$ is —$CH_2$—;

$R^3$ is selected from hydrogen, and an alkyl of 1 to 8 carbons wherein one or more of the hydrogens in the alkyl chain may optionally be substituted with a nitrogen of an amine;

L is alkyl chain of between 1 and 20 carbons, wherein the alkyl chain is optionally interrupted by one or more oxygen atoms, has one or more of hydrogens in the alkyl chain substituted for by a hydroxyl group, or terminates with a carbonyl functionality of general structure —CO—M, wherein M is a $OR^x$, $NR^xR^y$ and $R^x$ and $R^y$ are independently hydrogen or an alkyl group of between 1 and 8 carbons that optionally may have one or more of the hydrogens substituted for by a hydroxyl group; and $R^1$ and $R^2$ is individually a $C_1$ to $C_{10}$ straight chain alkyl, branched alkyl, or cycloalkyl and $R^1$ and $R^2$ are attached to an aromatic benzene ring so that they are ortho to each other.

36. The polymeric article of claim 35, wherein the amount of stabilizer composition is from about 0.01 to about 20 percent by weight of the polymeric material.

37. The polymeric article of claim 35, wherein the polymeric material is selected from the group consisting of polyolefins; polyesters; polyethers; polyketones; polyamides; natural and synthetic rubbers; polystyrenes; high-impact polystyrenes; polyacrylates; polymethacrylates; polyacetals; polyacrylonitriles; polybutadienes; polystyrenes; ABS; SAN (styrene acrylonitrile); ASA (acrylate styrene acrylonitrile); cellulosic acetate butyrate; cellulosic polymers; polyimides; polyamideimides; polyetherimides; polyphenylsulfides; PPO; polysulfones; polyethersulfones; polyvinylchlorides; polycarbonates; polyketones; aliphatic polyketones; thermoplastic TPO's; aminoresin crosslinked polyacrylates and polyesters; polyisocyanate crosslinked polyesters and polyacrylates; phenol/formaldehyde, urea/formaldehyde, and melamine/formaldehyde resins; drying and non-drying alkyd resins; alkyd resins; polyester resins; acrylate resins cross-linked with melamine resins, urea resins, isocyanates, isocyanurates, and epoxy resins; cross-linked epoxy resins derived from aliphatic, cycloaliphatic, heterocyclic and aromatic glycidyl compounds which are cross-linked with anhydrides or amines; polysiloxanes; Michael addition polymers of amines or blocked amines with activated unsaturated and methylene compounds, ketimines with activated unsaturated and methylene compounds, polyketimines in combination with unsaturated acrylic polyacetoacetate resins, and polyketimines in combination with unsaturated acrylic resins; radiation curable compositions; epoxymelamine resins; organic dyes; cosmetic products; cellulose-based paper formulations; photographic film paper; ink; and blends thereof.

38. The polymeric article of claim 35, wherein the one or more compounds is chemical bonded to the polymer.

39. The polymeric article of claim 35, wherein the stabilizer composition further comprises one or more hindered amine light stabilizers.

40. The polymeric article of claim 35, wherein the stabilizer composition further comprises one or more additional UV light absorbers selected from the group consisting of a benzotriazole, a triazine, a benzophenone, and mixtures thereof.

41. The polymeric article of claim 35, wherein the stabilizer composition further comprises at least one additional additive.

42. The polymeric article of claim 35, wherein the additive is selected from the group consisting of: antioxidants, ultraviolet light absorbers, ultraviolet light stabilizers, metal deactivators, phosphites, phosphonites, hydroxylamines, nitrones, thiosynergists, peroxide scavengers, polyamide stabilizers, nucleating agents, fillers, reinforcing agents, plasticizers, lubricants, emulsifiers, pigments, rheological additives, flameproofing agents, antistatic agents, blowing agents, benzofuranones and indolinones.

43. A multilayer polymeric article comprising a polymeric article having at least one surface and a thin film of polymer composition applied to the at least one surface that comprises a sufficient amount of at least one compound of formula (II)–(V) to inhibit at least one of photo or thermal degradation, wherein compound (II) has the structure:

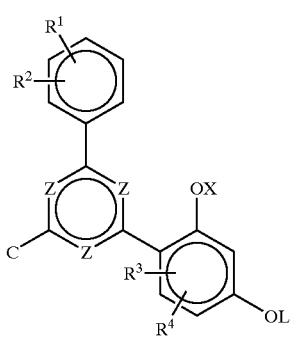

(II)

wherein each Z is nitrogen;

X is hydrogen or a blocking group selected from —COR$^a$, —SO$_2$R$^b$, —SiR$^c$R$^d$R$^e$, —PR$^f$R$^g$, —POR$^f$R$^g$, and —CONHR$^h$, wherein R$^a$ is a C$_1$–C$_8$ alkyl, halogen-substituted C$_1$–C$_8$ alkyl, C$_5$–C$_{12}$ cycloalkyl, C$_2$–C$_8$ alkenyl, —CH$_2$—CO—CH$_3$, C$_1$–C$_{12}$ alkoxy, and phenyl or phenoxy which is unsubstituted or substituted by C$_1$–C$_{12}$ alkyl, C$_1$–C$_4$ alkoxy, halogen or benzyl;

R$^b$ is a C$_1$–C$_{12}$ alkyl, C$_6$–C$_{10}$ aryl and C$_7$–C$_{18}$ alkylaryl;

R$^c$, R$^d$, and R$^e$ is independently selected from C$_1$–C$_8$ alkyl, cyclohexyl, phenyl or C$_1$–C$_8$ alkoxy, R$^f$, and R$^g$ is independently selected from C$_1$–C$_{12}$ alkoxy, C$_1$–C$_{12}$ alkyl, C$_5$–C$_{12}$ cycloalkyl, and phenyl or phenoxy which is unsubstituted or substituted by C$_1$–C$_{12}$ alkyl, C$_1$–C$_4$ alkoxy, halogen or benzyl; and R$^h$ is a C$_1$–C$_8$ alkyl, C$_5$–C$_{12}$ cycloalkyl, C$_2$–C$_8$ alkenyl, —CH$_2$—CO—CH$_3$, or phenyl which is unsubstituted or substituted by C$_1$–C$_{12}$ alkyl, C$_2$–C$_8$ alkenyl, C$_1$–C$_4$ alkoxy, halogen or benzyl;

C is

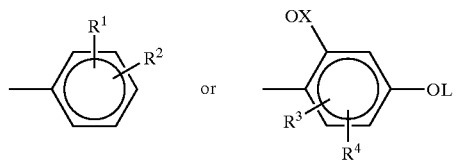

L is an alkyl chain between 1 and 20 carbons, wherein the alkyl chain is optionally interrupted by one or more oxygen atoms, has one or more of hydrogens in the alkyl chain substituted for by a hydroxyl group, or terminates with a carbonyl functionality of general structure CO—M, wherein M is a OR$^x$, NR$^x$R$^y$ and R$^x$ and R$^y$ are independently hydrogen or an alkyl group of between 1 and 8 carbons that optionally may have one or more of the hydrogens substituted for by a hydroxyl group;

R$^3$ and R$^4$ is independently selected from hydrogen, and an alkyl of 1 to 8 carbons wherein one or more of the hydrogens in the alkyl chain may optionally be substituted with a nitrogen of an amine; and each R$^1$ and R$^2$ is individually a C$_1$ to C$_{10}$ straight chain alkyl, branched alkyl, or cycloalkyl and R$^1$ and R$^2$ are attached to an aromatic benzene ring so that they are ortho to each other;

compound (III) has the structure:

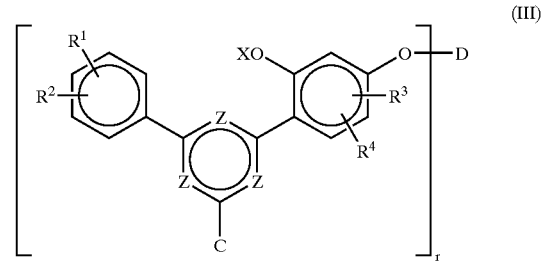

(III)

wherein each Z is nitrogen;
X is defined above;
C is

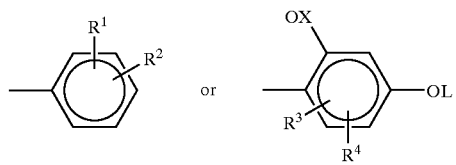

r is 2 and D is an alkyl chain of between 1 and 10 carbons or —CO—P—CO—, wherein P is an alkyl chain of between 1 and 10 carbons or a benzene ring wherein the carbonyl groups are meta or para to each other;

$R^3$ and $R^4$ is independently selected from hydrogen, and an alkyl of 1 to 8 carbons wherein one or more of the hydrogens in the alkyl chain may optionally be substituted with a nitrogen of an amine; and $R^1$ and $R^2$ is individually a $C_1$ to $C_{10}$ straight chain alkyl, branched alkyl, or cycloalkyl and $R^1$ and $R^2$ are attached to an aromatic benzene ring so that they are ortho to each other;

compound (IV) has the structure:

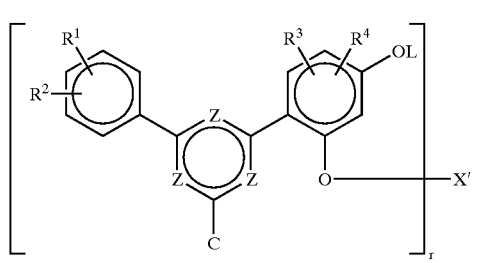

(IV)

wherein each Z is nitrogen;

C is

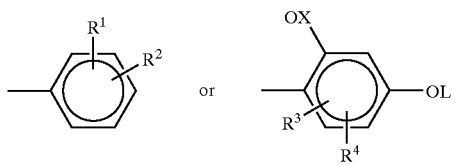

wherein r is 2 and X' is an alkyl chain of between 1 and 10 carbons or —CO—P—CO—, wherein P is an alkyl chain of between 1 and 10 carbons or a benzene ring wherein the carbonyl groups are meta or para to each other;

$R^3$ and $R^4$ is independently selected from hydrogen, and an alkyl of 1 to 8 carbons wherein one or more of the hydrogens in the alkyl chain may optionally be substituted with a nitrogen of an amine;

L is alkyl chain of between 1 and 20 carbons, wherein the alkyl chain is optionally interrupted by one or more oxygen atoms, has one or more of hydrogens in the alkyl chain substituted for by a hydroxyl group, or terminates with a carbonyl functionality of general structure —CO—M, wherein M is a $OR^x$, $NR^xR^y$ and $R^x$ and $R^y$ are independently hydrogen or an alkyl group of between 1 and 8 carbons that optionally may have one or more of the hydrogens substituted for by a hydroxyl group;

$R^1$ and $R^2$ is individually a $C_1$ to $C_{10}$ straight chain alkyl, branched alkyl, or cycloalkyl and $R^1$ and $R^2$ are attached to an aromatic benzene ring so that they are ortho to each other;

and compound (V) has the structure:

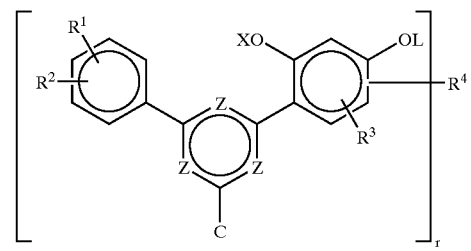

(V)

wherein each Z is nitrogen;
X is defined above;
C is

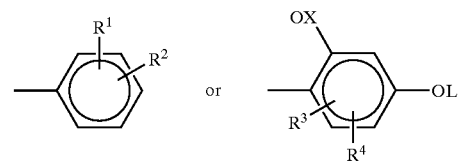

r is 2;
$R^4$ is —$CH_2$—;
$R^3$ is selected from hydrogen, and an alkyl of 1 to 8 carbons wherein one or more of the hydrogens in the alkyl chain may optionally be substituted with a nitrogen of an amine;

L is alkyl chain of between 1 and 20 carbons, wherein the alkyl chain is optionally interrupted by one or more oxygen atoms, has one or more of hydrogens in the alkyl chain substituted for by a hydroxyl group, or terminates with a carbonyl functionality of general structure —CO—M, wherein M is a $OR^x$, $NR^xR^y$ and $R^x$ and $R^y$ are independently hydrogen or an alkyl group of between 1 and 8 carbons that optionally may have one or more of the hydrogens substituted for by a hydroxyl group; and $R^1$ and $R^2$ is individually a $C_1$ to $C_{10}$ straight chain alkyl, branched alkyl, or cycloalkyl and $R^1$ and $R^2$ are attached to an aromatic benzene ring so that they are ortho to each other.

44. The multilayer polymeric article of claim 43, wherein the thin film is applied to each surface of the polymeric article.

45. The multilayer polymeric article of claim 43, wherein the amount of the compound is from about 0.1 to 20 percent by weight of the thin film.

46. The multilayer polymeric article of claim 43, wherein the thin film is from about 5 to 500 µm in thickness.

47. A coating comprising a sufficient amount of at least one compound of formula (II)–(V) to inhibit at least one of photo or thermal degradation, wherein compound (II) has the structure:

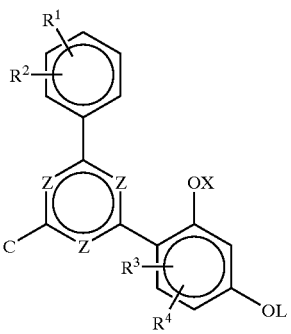

(II)

wherein each Z is nitrogen;

X is hydrogen or a blocking group selected from —COR$^a$, —SO$_2$R$^b$, —SiR$^c$R$^d$R$^e$, —PR$^f$R$^g$, —POR$^f$R$^g$, and —CONHR$^h$, wherein R$^a$ is a C$_1$–C$_8$ alkyl, halogen-substituted C$_1$–C$_8$ alkyl, C$_5$–C$_{12}$ cycloalkyl, C$_2$–C$_8$ alkenyl, —CH—CO—CH$_3$, C$_1$–C$_{12}$ alkoxy, and phenyl or phenoxy which is unsubstituted or substituted by C$_1$–C$_{12}$ alkyl, C$_1$–C$_4$ alkoxy, halogen or benzyl;

R$^b$ is a C$_1$–C$_{12}$ alkyl, C$_6$–C$_{10}$ aryl and C$_7$–C$_{18}$ alkylaryl;

R$^c$, R$^d$, and R$^e$ is independently selected from C$_1$–C$_8$ alkyl, cyclohexyl, phenyl or C$_1$–C$_8$ alkoxy, R$^f$, and R$^g$ is independently selected from C$_1$–C$_{12}$ alkoxy, C$_1$–C$_{12}$ alkyl, C$_5$–C$_{12}$ cycloalkyl, and phenyl or phenoxy which is unsubstituted or substituted by C$_1$–C$_{12}$ alkyl, C$_1$–C$_4$ alkoxy, halogen or benzyl; and R$^h$ is a C$_1$–C$_8$ alkyl, C$_5$–C$_{12}$ cycloalkyl, C$_2$–C$_8$ alkenyl, —CH$_2$—CO—CH$_3$, or phenyl which is unsubstituted or substituted by C$_1$–C$_{12}$ alkyl, C$_2$–C$_8$ alkenyl, C$_1$–C$_4$ alkoxy, halogen or benzyl;

C is

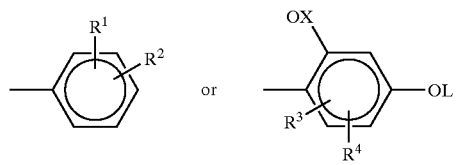

L is an alkyl chain of between 1 and 20 carbons, wherein the alkyl chain is optionally interrupted by one or more oxygen atoms, has one or more of hydrogens in the alkyl chain substituted for by a hydroxyl group, or terminates with a carbonyl functionality of general structure —CO—M, wherein M is a OR$^x$, NR$^x$R$^y$ and R$^x$ and R$^y$ are independently hydrogen or an alkyl group of between 1 and 8 carbons that optionally may have one or more of the hydrogens substituted for by a hydroxyl group;

R$^3$ and R$^4$ is independently selected from hydrogen, and an alkyl of 1 to 8 carbons wherein one or more of the hydrogens in the alkyl chain may optionally be substituted with a nitrogen of an amine; and each R$^1$ and R$^2$ is individually a C$_1$ to C$_{10}$ straight chain alkyl, branched alkyl, or cycloalkyl and R$^1$ and R$^2$ are attached to an aromatic benzene ring so that they are ortho to each other;

compound (III) has the structure:

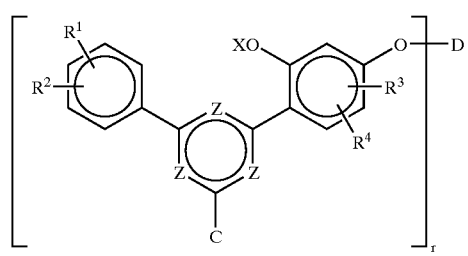

(III)

wherein each Z is nitrogen;

X is defined above;

C is

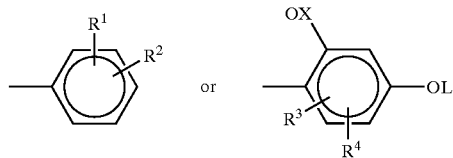

r is 2 and D is an alkyl chain of between 1 and 10 carbons or —CO—P—CO—, wherein P is an alkyl chain of between 1 and 10 carbons or a benzene ring wherein the carbonyl groups are meta or para to each other;

R$^3$ and R$^4$ is independently selected from hydrogen, and an alkyl of 1 to 8 carbons wherein one or more of the hydrogens in the alkyl chain may optionally be substituted with a nitrogen of an amine; and R$^1$ and R$^2$ is individually a C$_1$ to C$_{10}$ straight chain alkyl, branched alkyl, or cycloalkyl and R$^1$ and R$^2$ are attached to an aromatic benzene ring so that they are ortho to each other;

compound (IV) has the structure:

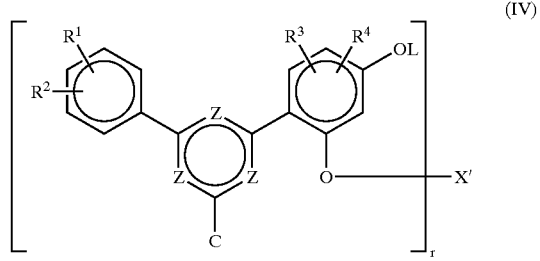

(IV)

wherein each Z is nitrogen;

C is

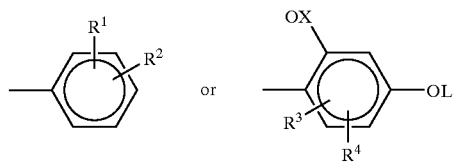

wherein r is 2 and X' is an alkyl chain of between 1 and 10 carbons or —CO—P—CO—, wherein P is an alkyl chain of between 1 and 10 carbons or a benzene ring wherein the carbonyl groups are meta or para to each other;

R$^3$ and R$^4$ is independently selected from hydrogen, and an alkyl of 1 to 8 carbons wherein one or more of the hydrogens in the alkyl chain may optionally be substituted with a nitrogen of an amine;

L is alkyl chain of between 1 and 20 carbons, wherein the alkyl chain is optionally interrupted by one or more oxygen atoms, has one or more of hydrogens in the alkyl chain substituted for by a hydroxyl group, or terminates with a carbonyl functionality of general structure —CO—M, wherein M is a OR$^x$, NR$^x$R$^y$ and R$^x$ and R$^y$ are independently hydrogen or an alkyl group of between 1 and 8 carbons that optionally may have one or more of the hydrogens substituted for by a hydroxyl group;

$R^1$ and $R^2$ is individually a $C_1$ to $C_{10}$ straight chain alkyl, branched alkyl, or cycloalkyl and $R^1$ and $R^2$ are attached to an aromatic benzene ring so that they are ortho to each other;

and compound (V) has the structure:

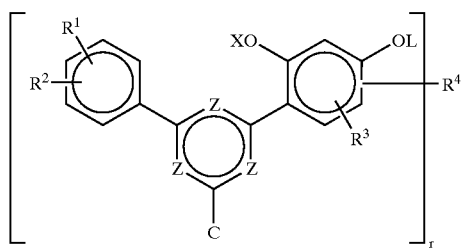
(V)

wherein each Z is nitrogen;

X is defined above;

C is

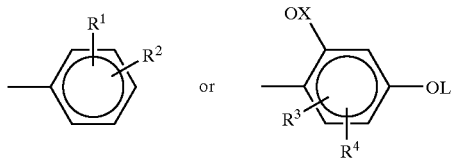

r is 2;

$R^4$ is —$CH_2$—;

$R^3$ is selected from hydrogen, and an alkyl of 1 to 8 carbons wherein one or more of the hydrogens in the alkyl chain may optionally be substituted with a nitrogen of an amine;

L is alkyl chain of between 1 and 20 carbons, wherein the alkyl chain is optionally interrupted by one or more oxygen atoms, has one or more of hydrogens in the alkyl chain substituted for by a hydroxyl group, or terminates with a carbonyl functionality of general structure —CO—M, wherein M is a $OR^x$, $NR^xR^y$ and $R^x$ and $R^y$ are independently hydrogen or an alkyl group of between 1 and 8 carbons that optionally may have one or more of the hydrogens substituted for by a hydroxyl group; and $R^1$ and $R^2$ is individually a $C_1$ to $C_{10}$ straight chain alkyl, branched alkyl, or cycloalkyl and $R^1$ and $R^2$ are attached to an aromatic benzene ring so that they are ortho to each other.

48. The coating of claim 47, wherein the amount of the at least one compound is from about 0.01 to 20 percent by weight of the coating.

49. A concentrate comprising a polymeric resin and from about 2.5 to about 25 percent of at least one compound of formula (II)–(V), wherein compound (II) has the structure:

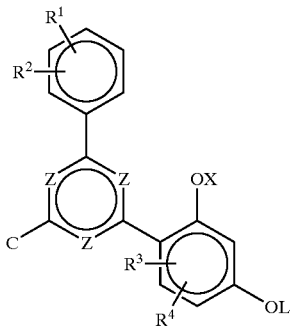
(II)

wherein each Z is nitrogen;

X is hydrogen or a blocking group selected from —$COR^a$, —$SO_2R^b$, —$SiR^cR^dR^e$, —$PR^fR^g$, —$POR^fR^g$, and —$CONHR^h$, wherein $R^a$ is a $C_1$–$C_8$ alkyl, halogen-substituted $C_1$–$C_8$ alkyl, $C_5$–$C_{12}$ cycloalkyl, $C_2$–$C_8$ alkenyl, —CH—CO—$CH_3$, $C_1$–$C_{12}$ alkoxy, and phenyl or phenoxy which is unsubstituted or substituted by $C_1$–$C_{12}$ alkyl, $C_1$–$C_4$ alkoxy, halogen or benzyl;

$R^b$ is a $C_1$–$C_{12}$ alkyl, $C_6$–$C_{10}$ aryl and $C_7$–$C_{18}$ alkylaryl;

$R^c$, $R^d$, and $R^e$ is independently selected from $C_1$–$C_8$ alkyl, cyclohexyl, phenyl or $C_1$–$C_8$ alkoxy, $R^f$, and $R^g$ is independently selected from $C_1$–$C_{12}$ alkoxy, $C_1$–$C_{12}$ alkyl, $C_5$–$C_{12}$ cycloalkyl, and phenyl or phenoxy which is unsubstituted or substituted by $C_1$–$C_{12}$ alkyl, $C_1$–$C_4$ alkoxy, halogen or benzyl; and $R^h$ is a $C_1$–$C_8$ alkyl, $C_5$–$C_{12}$ cycloalkyl, $C_2$–$C_8$ alkenyl, —$CH_2$—CO—$CH_3$, or phenyl which is unsubstituted or substituted by $C_1$–$C_{12}$ alkyl, $C_2$–$C_8$ alkenyl, $C_1$–$C_4$ alkoxy, halogen or benzyl;

C is

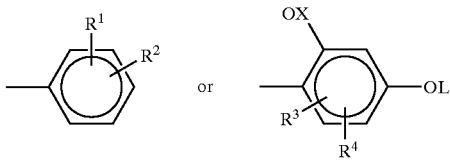

L is an alkyl chain of between 1 and 20 carbons, wherein the alkyl chain is optionally interrupted by one or more oxygen atoms, has one or more of hydrogens in the alkyl chain substituted for by a hydroxyl group, or terminates with a carbonyl functionality of general structure —CO—M, wherein M is a $OR^x$, $NR^xR^y$ and $R^x$ and $R^y$ are independently hydrogen or an alkyl group of between 1 and 8 carbons that optionally may have one or more of the hydrogens substituted for by a hydroxyl group;

$R^3$ and $R^4$ is independently selected from hydrogen, and an alkyl of 1 to 8 carbons wherein one or more of the hydrogens in the alkyl chain may optionally be substituted with a nitrogen of an amine; and each $R^1$ and $R^2$ is individually a $C_1$ to $C_{10}$ straight chain alkyl, branched alkyl, or cycloalkyl and $R^1$ and $R^2$ are attached to an aromatic benzene ring so that they are ortho to each other;

compound (III) has the structure:

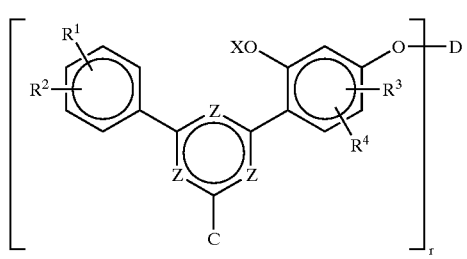
(III)

wherein each Z is nitrogen;
X is defined above;
C is

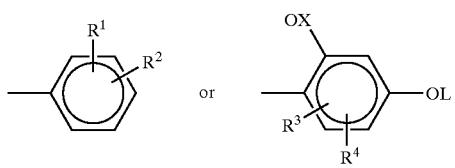

r is 2 and D is an alkyl chain of between 1 and 10 carbons or —CO—P—CO—, wherein P is an alkyl chain of between 1 and 10 carbons or a benzene ring wherein the carbonyl groups are meta or para to each other;

$R^3$ and $R^4$ is independently selected from hydrogen, and an alkyl of 1 to 8 carbons wherein one or more of the hydrogens in the alkyl chain may optionally be substituted with a nitrogen of an amine; and $R^1$ and $R^2$ is individually a $C_1$ to $C_{10}$ straight chain alkyl, branched alkyl, or cycloalkyl and $R^1$ and $R^2$ are attached to an aromatic benzene ring so that they are ortho to each other;

compound (IV) has the structure:

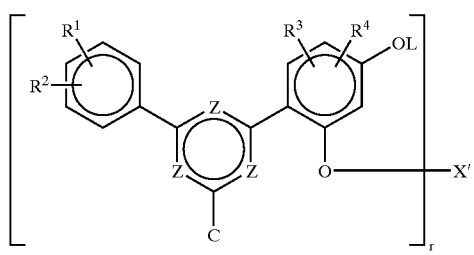
(IV)

wherein each Z is nitrogen;
C is

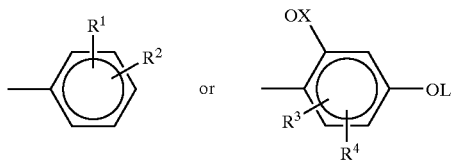

wherein r is 2 and X' is an alkyl chain of between 1 and 10 carbons or —CO—P—CO—, wherein P is an alkyl chain of between 1 and 10 carbons or a benzene ring wherein the carbonyl groups are meta or para to each other;

$R^3$ and $R^4$ is independently selected from hydrogen, and an alkyl of 1 to 8 carbons wherein one or more of the hydrogens in the alkyl chain may optionally be substituted with a nitrogen of an amine;

L is alkyl chain of between 1 and 20 carbons, wherein the alkyl chain is optionally interrupted by one or more oxygen atoms, has one or more of hydrogens in the alkyl chain substituted for by a hydroxyl group, or terminates with a carbonyl functionality of general structure —CO—M, wherein M is a $OR^x$, $NR^xR^y$ and $R^x$ and $R^y$ are independently hydrogen or an alkyl group of between 1 and 8 carbons that optionally may have one or more of the hydrogens substituted for by a hydroxyl group;

$R^1$ and $R^2$ is individually a $C_1$ to $C_{10}$ straight chain alkyl, branched alkyl, or cycloalkyl and $R^1$ and $R^2$ are attached to an aromatic benzene ring so that they are ortho to each other;

and compound (V) has the structure:

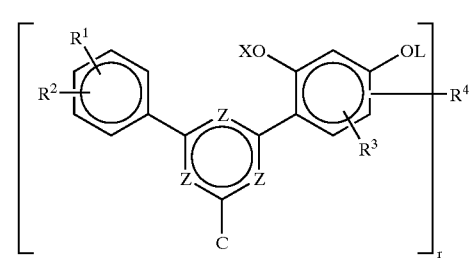
(V)

wherein each Z is nitrogen;
X is defined above;
C is

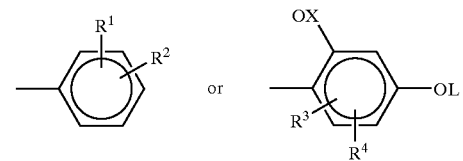

r is 2;
$R^4$ is —$CH_2$—;
$R^3$ is selected from hydrogen, and an alkyl of 1 to 8 carbons wherein one or more of the hydrogens in the alkyl chain may optionally be substituted with a nitrogen of an amine;

L is alkyl chain of between 1 and 20 carbons, wherein the alkyl chain is optionally interrupted by one or more oxygen atoms, has one or more of hydrogens in the alkyl chain substituted for by a hydroxyl group, or terminates with a carbonyl functionality of general structure —CO—M, wherein M is a $OR^x$, $NR^xR^y$ and $R^x$ and $R^y$ are independently hydrogen or an alkyl group of between 1 and 8 carbons that optionally may have one or more of the hydrogens substituted for by a hydroxyl group; and $R^1$ and $R^2$ is individually a $C_1$ to $C_{10}$ straight chain alkyl, branched alkyl, or cycloalkyl and $R^1$ and $R^2$ are attached to an aromatic benzene ring so that they are ortho to each other.

50. A cosmetic composition comprising a sufficient amount of at least one compound of formula (II)–(V), wherein compound (II) has the structure:

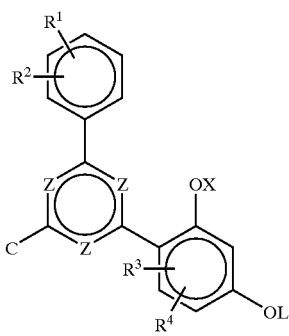

wherein each Z is nitrogen;

X is as defined in claim hydrogen or a blocking group selected from —COR$^a$, —SO$_2$R$^b$, —SiR$^c$R$^d$R$^e$, —PR$^f$R$^g$, —POR$^f$R$^g$, and —CONHR$^h$, wherein R$^a$ is a C$_1$–C$_8$ alkyl halogen-substituted C$_1$–C$_8$ alkyl, C$_5$–C$_{12}$ cycloalkyl, C$_2$–C$_8$ alkenyl, —CH$_2$—CO—CH$_3$, C$_1$–C$_{12}$ alkoxy, and phenyl or phenoxy which is unsubstituted or substituted by C$_1$–C$_{12}$ alkyl, C$_1$–C$_4$ alkoxy, halogen or benzyl;

R$^b$ is a C$_1$–C$_{12}$ alkyl, C$_6$–C$_{10}$ aryl and C$_7$–C$_{18}$ alkylaryl;

R$^c$, R$^d$, and R$^e$ is independently selected from C$_1$–C$_8$ alkyl, cyclohexyl, phenyl or C$_1$–C$_8$ alkoxy, R$^f$, and R$^g$ is independently selected from C$_1$–C$_{12}$ alkoxy, C$_1$–C$_{12}$ alkyl, C$_5$–C$_{12}$ cycloalkyl, and phenyl or phenoxy which is unsubstituted or substituted by C$_1$–C$_{12}$ alkyl, C$_1$–C$_4$ alkoxy, halogen or benzyl; and R$^h$ is a C$_1$–C$_8$ alkyl, C$_5$–C$_{12}$ cycloalkyl, C$_2$–C$_8$ alkenyl, —CH$_2$—CO—CH$_3$, or phenyl which is unsubstituted or substituted by C$_1$–C$_{12}$ alkyl, C$_2$–C$_8$ alkenyl, C$_1$–C$_4$ alkoxy, halogen or benzyl;

C is

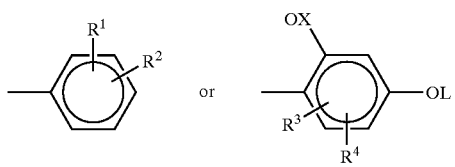

L is an alkyl chain of between 1 and 20 carbons, wherein the alkyl chain is optionally interrupted by one or more oxygen atoms, has one or more of hydrogens in the alkyl chain substituted for by a hydroxyl group, or terminates with a carbonyl functionality of general structure —CO—M, wherein M is a OR$^x$, NR$^x$R$^y$ and R$^x$ and R$^y$ are independently hydrogen or an alkyl group of between 1 and 8 carbons that optionally may have one or more of the hydrogens substituted for by a hydroxyl group;

R$^3$ and R$^4$ is independently selected from hydrogen, and an alkyl of 1 to 8 carbons wherein one or more of the hydrogens in the alkyl chain may optionally be substituted with a nitrogen of an amine; and each R$^3$ and R$^2$ is individually a C$_1$ to C$_{10}$ straight chain alkyl, branched alkyl, or cycloalkyl and R$^x$ and R$^2$ are attached to an aromatic benzene ring so that they are ortho to each other;

compound (III) has the structure:

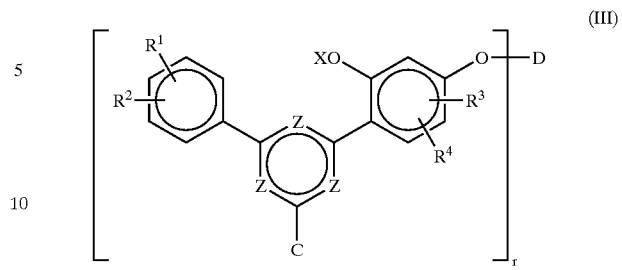

wherein each Z is nitrogen;
X is defined above;
C is

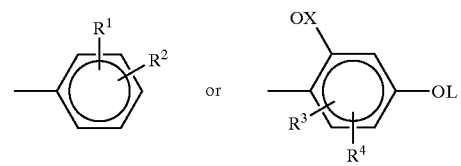

r is 2 and D is an alkyl chain of between 1 and 10 carbons or —CO—P—CO—, wherein P is an alkyl chain of between 1 and 10 carbons or a benzene ring wherein the carbonyl groups are meta or para to each other;

R$^3$ and R$^4$ is independently selected from hydrogen, and an alkyl of 1 to 8 carbons wherein one or more of the hydrogens in the alkyl chain may optionally be substituted with a nitrogen of an amine; and R$^1$ and R$^2$ is individually a C$_1$ to C$_{10}$ straight chain alkyl, branched alkyl, or cycloalkyl and R$^1$ and R$^2$ are attached to an aromatic benzene ring so that they are ortho to each other;

compound (IV) has the structure:

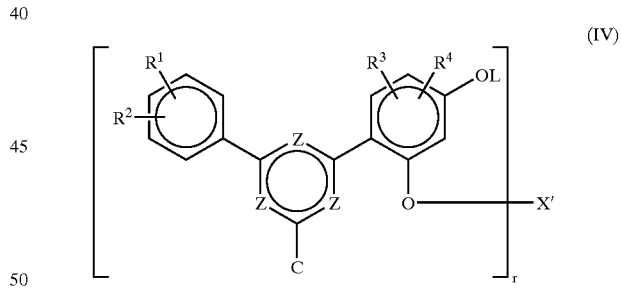

wherein each Z is nitrogen;
C is

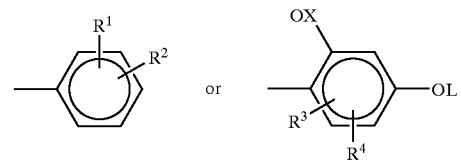

wherein r is 2 and X' is an alkyl chain of between 1 and 10 carbons or —CO—P—CO—, wherein P is an alkyl chain of between 1 and 10 carbons or a benzene ring wherein the carbonyl groups are meta or para to each other;

$R^3$ and $R^4$ is independently selected from hydrogen, and an alkyl of 1 to 8 carbons wherein one or more of the hydrogens in the alkyl chain may optionally be substituted with a nitrogen of an amine;

L is alkyl chain of between 1 and 20 carbons, wherein the alkyl chain is optionally interrupted by one or more oxygen atoms, has one or more of hydrogens in the alkyl chain substituted for by a hydroxyl group, or terminates with a carbonyl functionality of general structure —CO—M, wherein M is a $OR^x$, $NR^xR^y$ and $R^x$ and $R^y$ are independently hydrogen or an alkyl group of between 1 and 8 carbons that optionally may have one or more of the hydrogens substituted for by a hydroxyl group;

$R^1$ and $R^2$ is individually a $C_1$ to $C_{10}$ straight chain alkyl, branched alkyl, or cycloalkyl and $R^1$ and $R^2$ are attached to an aromatic benzene ring so that they are ortho to each other;

and compound (V) has the structure:

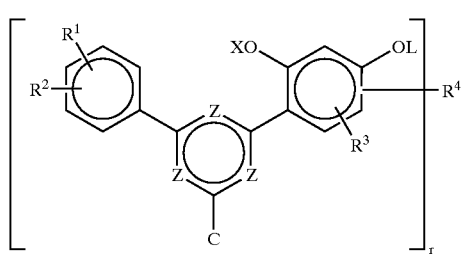

(V)

wherein each Z is nitrogen;
X is defined above;
C is

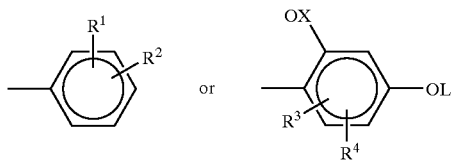

or r is 2;
$R^4$ is —CH$_2$—;
$R^3$ is selected from hydrogen, and an alkyl of 1 to 8 carbons wherein one or more of the hydrogens in the alkyl chain may optionally be substituted with a nitrogen of an amine;

L is alkyl chain of between 1 and 20 carbons, wherein the alkyl chain is optionally interrupted by one or more oxygen atoms, has one or more of hydrogens in the alkyl chain substituted for by a hydroxyl group, or terminates with a carbonyl functionality of general structure —CO—M, wherein M is a $OR^x$, $NR^xR^y$ and $R^x$ and $R^y$ are independently hydrogen or an alkyl group of between 1 and 8 carbons that optionally may have one or more of the hydrogens substituted for by a hydroxyl group; and $R^1$ and $R^2$ is individually a $C_1$ to $C_{10}$ straight chain alkyl, branched alkyl, or cycloalkyl and $R^1$ and $R^2$ are attached to an aromatic benzene ring so that they are ortho to each other.

51. A method of stabilizing a material that is subject to at least one of photo or thermal degradation by incorporating into or onto the material an amount of one or more stabilizer compositions in an amount effective to stabilize the material against at least one of photo or thermal degradation, wherein the stabilizer composition comprises one or more compounds of structure (II)–(V), wherein compound (II) has the structure:

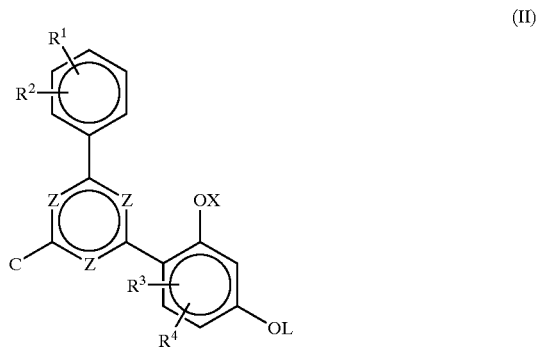

(II)

wherein each Z is nitrogen;
X is hydrogen or a blocking group selected from —COR$^a$, —SO$_2$R$^b$, —SiR$^c$R$^d$R$^e$, —PR$^f$R$^g$, —POR$^f$R$^g$ and —CONHR$^h$, wherein R$^a$ is a $C_1$–$C_8$ alkyl halogen-substituted $C_1$–$C_8$ alkyl, $C_5$–$C_{12}$ cycloalkyl, $C_2$–$C_8$ alkenyl, —CH$_2$—CO—CH$_3$, $C_1$–$C_{12}$ alkoxy, and phenyl or phenoxy which is unsubstituted or substituted by $C_1$–$C_{12}$ alkyl, $C_1$–$C_4$ alkoxy, halogen or benzyl;

R$^b$ is a $C_1$–$C_{12}$ alkyl, $C_6$–$C_{10}$ aryl and $C_7$–$C_{18}$ alkylaryl;

R$^c$, R$^d$, and R$^e$ is independently selected from $C_1$–$C_8$ alkyl, cyclohexyl, phenyl or $C_1$–$C_8$ alkoxy, R$^f$, and R$^g$ is independently selected from $C_1$–$C_{12}$ alkoxy, $C_1$–$C_{12}$ alkyl, $C_5$–$C_{12}$ cycloalkyl, and phenyl or phenoxy which is unsubstituted or substituted by $C_1$–$C_{12}$ alkyl, $C_1$–$C_4$ alkoxy, halogen or benzyl; and R$^h$ is a $C_1$–$C_8$ alkyl, $C_5$–$C_{12}$ cycloalkyl, $C_2$–$C_8$ alkenyl, —CH$_2$—CO—CH$_3$, or phenyl which is unsubstituted or substituted by $C_1$–$C_{12}$ alkyl, $C_2$–$C_8$ alkenyl, $C_1$–$C_4$ alkoxy, halogen or benzyl;

C is

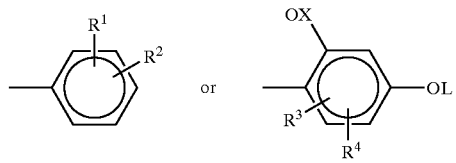

or

L is an alkyl chain of between 1 and 20 carbons, wherein the alkyl chain is optionally interrupted by one or more oxygen atoms, has one or more of hydrogens in the alkyl chain substituted for by a hydroxyl group, or terminates with a carbonyl functionality of general structure CO—M, wherein M is a $OR^x$, $NR^xR^y$ and $R^x$ and $R^y$ are independently hydrogen or an alkyl group of between 1 and 8 carbons that optionally may have one or more of the hydrogens substituted for by a hydroxyl group;

$R^3$ and $R^4$ is independently selected from hydrogen, and an alkyl of 1 to 8 carbons wherein one or more of the hydrogens in the alkyl chain may optionally be substituted with a nitrogen of an amine; and each $R^1$ and $R^2$ is individually a $C_1$ to $C_{10}$ straight chain alkyl, branched alkyl, or cycloalkyl and $R^1$ and $R^2$ are attached to an aromatic benzene ring so that they are ortho to each other;

compound (III) has the structure:

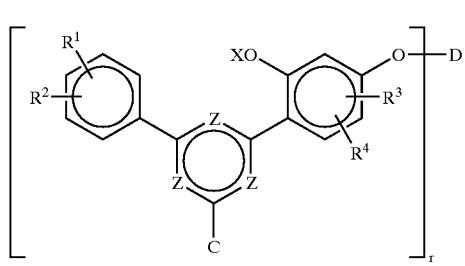

(III)

wherein each Z is nitrogen;
X is defined above;
C is

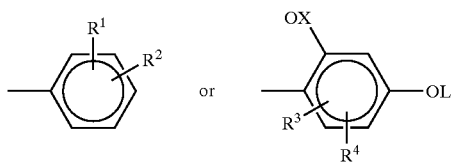

r is 2 and D is an alkyl chain of between 1 and 10 carbons or —CO—P—CO—, wherein P is an alkyl chain of between 1 and 10 carbons or a benzene ring wherein the carbonyl groups are meta or para to each other;

$R^3$ and $R^4$ is independently selected from hydrogen, and an alkyl of 1 to 8 carbons wherein one or more of the hydrogens in the alkyl chain may optionally be substituted with a nitrogen of an amine; and $R^1$ and $R^2$ is individually a $C_1$ to $C_{10}$ straight chain alkyl, branched alkyl, or cycloalkyl and $R^1$ and $R^2$ are attached to an aromatic benzene ring so that they are ortho to each other;

compound (IV) has the structure:

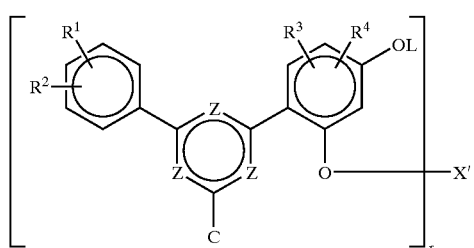

(IV)

wherein each Z is nitrogen;
C is

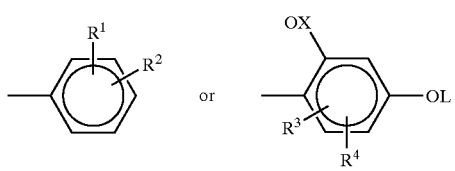

wherein r is 2 and X' is an alkyl chain of between 1 and 10 carbons or —CO—P—CO—, wherein P is an alkyl chain of between 1 and 10 carbons or a benzene ring wherein the carbonyl groups are meta or para to each other;

$R^3$ and $R^4$ is independently selected from hydrogen, and an alkyl of 1 to 8 carbons wherein one or more of the hydrogens in the alkyl chain may optionally be substituted with a nitrogen of an amine;

L is alkyl chain of between 1 and 20 carbons, wherein the alkyl chain is optionally interrupted by one or more oxygen atoms, has one or more of hydrogens in the alkyl chain substituted for by a hydroxyl group, or terminates with a carbonyl functionality of general structure —CO—M, wherein M is a $OR^x$, $NR^xR^y$ and $R^x$ and $R^y$ are independently hydrogen or an alkyl group of between 1 and 8 carbons that optionally may have one or more of the hydrogens substituted for by a hydroxyl group;

$R^1$ and $R^2$ is individually a $C_1$ to $C_{10}$ straight chain alkyl, branched alkyl, or cycloalkyl and $R^1$ and $R^2$ are attached to an aromatic benzene ring so that they are ortho to each other;

and compound (V) has the structure:

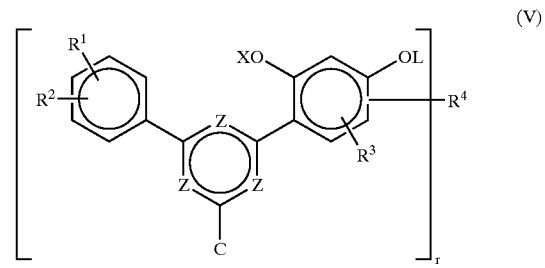

(V)

wherein each Z is nitrogen;
X is defined above;
C is

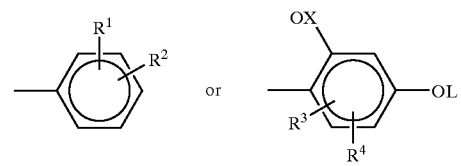

r is 2;
$R^4$ is —$CH_2$—;
$R^3$ is selected from hydrogen, and an alkyl of 1 to 8 carbons wherein one or more of the hydrogens in the alkyl chain may optionally be substituted with a nitrogen of an amine;

L is alkyl chain of between 1 and 20 carbons, wherein the alkyl chain is optionally interrupted by one or more oxygen atoms, has one or more of hydrogens in the alkyl chain substituted for by a hydroxyl group, or terminates with a carbonyl functionality of general structure —CO—M, wherein M is a $OR^x$, $NR^xR^y$ and $R^x$ and $R^y$ are independently hydrogen or an alkyl group of between 1 and 8 carbons that optionally may have one or more of the hydrogens substituted for by a hydroxyl group; and $R^1$ and $R^2$ is individually a $C_1$ to $C_{10}$ straight chain alkyl, branched alkyl, or cycloalkyl and $R^1$ and $R^2$ are attached to an aromatic benzene ring so that they are ortho to each other.

52. The method of claim 51, wherein the stabilizer composition is incorporated in an amount of from about 0.01 to about 20 percent by weight of the material to be stabilized.

53. The method of claim 51, wherein the material to be stabilized is polymeric.

54. The method of claim 53, wherein the polymeric material is selected from the group consisting of polyolefins; polyesters; polyethers; polyketones; polyamides; natural and synthetic rubbers; polyurethanes; polystyrenes; high-impact polystyrenes; polyacrylates; polymethacrylates; polyacetals; polyacrylonitriles; polybutadienes; polystyrenes; ABS; SAN (styrene acrylonitrile); ASA (acrylate styrene acrylonitrile); cellulosic acetate butyrate; cellulosic polymers; polyimides; polyamideimides; polyetherimides; polyphenylsulfides; PPO; polysulfones; polyethersulfones; polyvinylchlorides; polycarbonates; polyketones; aliphatic polyketones; thermoplastic TPO's; aminoresin crosslinked polyacrylates and polyesters; polyisocyanate crosslinked polyesters and polyacrylates; phenol/formaldehyde, urea/formaldehyde, and melamine/formaldehyde resins; drying and non-drying alkyd resins; alkyd resins; polyester resins; acrylate resins cross-linked with melamine resins, urea resins, isocyanates, isocyanurates, carbamates, and epoxy resins; cross-linked epoxy resins derived from aliphatic, cycloaliphatic, heterocyclic and aromatic glycidyl compounds which are cross-linked with anhydrides or amines; polysiloxanes; Michael addition polymers of amines or blocked amines with activated unsaturated and methylene compounds, ketimines with activated unsaturated and methylene compounds, polyketimines in combination with unsaturated acrylic polyacetoacetate resins, and polyketimines in combination with unsaturated acrylic resins; radiation curable compositions; epoxymelamine resins; organic dyes; cosmetic products; cellulose-based paper formulations; photographic film paper; ink; and blends thereof.

55. The method of claim 51, wherein the one or more compounds is incorporated into the polymer by chemical bonding during and/or subsequent to the preparation of the polymer.

56. The method of claim 51, wherein the material has one or more surfaces and the stabilizer composition is applied to at least one surface of the material.

57. The method of claim 56, wherein the stabilizer composition is part of a coating that is applied to the at least one surface of the material.

58. The method of claim 56, wherein the material is metallic, wood, ceramic, polymeric, or a fiber material.

59. The method of claim 51, further comprising chemically bonding the one or more compounds to the material.

60. The method of claim 59, further comprising forming the material into a fiber.

61. The method of claim 59, wherein the material is selected from the group consisting of silk, leather, wool, polyamide, polyurethane, cellulose-containing fibers, and blends thereof.

62. The method of claim 51, wherein the material is a photographic material.

63. The method of claim 51, wherein the material is a cosmetic composition.

* * * * *